US010036021B2

(12) United States Patent
Hartmann et al.

(10) Patent No.: US 10,036,021 B2
(45) Date of Patent: Jul. 31, 2018

(54) 5' TRIPHOSPHATE OLIGONUCLEOTIDE WITH BLUNT END AND USES THEREOF

(71) Applicant: Rheinische Friedrich-Wilhelms-Universität Bonn, Bonn (DE)

(72) Inventors: Gunther Hartmann, Bonn (DE); Martin Schlee, Bonn-Bad Godesberg (DE)

(73) Assignee: Rheinische Friedrich-Wilhelms-Universität Bonn, Bonn (DE)

( * ) Notice: Subject to any disclaimer, the term of this patent is extended or adjusted under 35 U.S.C. 154(b) by 0 days.

(21) Appl. No.: 15/151,057

(22) Filed: May 10, 2016

(65) Prior Publication Data

US 2016/0333347 A1 Nov. 17, 2016

Related U.S. Application Data

(63) Continuation of application No. 12/993,420, filed as application No. PCT/EP2009/003621 on May 20, 2009, now Pat. No. 9,738,680.

(60) Provisional application No. 61/076,986, filed on Jun. 30, 2008, provisional application No. 61/082,431, filed on Jul. 21, 2008, provisional application No. 61/092,825, filed on Aug. 29, 2008, provisional application No. 61/100,594, filed on Sep. 26, 2008.

(30) Foreign Application Priority Data

May 21, 2008 (EP) .................... 08009406
Aug. 29, 2008 (EP) .................... 08015261
Oct. 17, 2008 (EP) .................... 08018243

(51) Int. Cl.
*C12N 15/117* (2010.01)
*A61K 45/06* (2006.01)
*A61K 39/00* (2006.01)
*C12N 15/113* (2010.01)
*A61K 31/7088* (2006.01)
*C07H 21/00* (2006.01)
*A61K 31/713* (2006.01)

(52) U.S. Cl.
CPC ...... *C12N 15/1135* (2013.01); *A61K 31/7088* (2013.01); *A61K 31/713* (2013.01); *A61K 45/06* (2013.01); *C07H 21/00* (2013.01); *C12N 15/113* (2013.01); *C12N 15/117* (2013.01); *C12N 15/1131* (2013.01); *C12N 2310/14* (2013.01); *C12N 2310/17* (2013.01); *C12N 2310/315* (2013.01); *C12N 2310/321* (2013.01); *C12N 2310/531* (2013.01); *C12N 2320/31* (2013.01)

(58) Field of Classification Search
USPC .......... 435/6.1, 6.11, 91.1, 91.31, 455, 375; 514/1, 2, 44; 536/23.1, 24.5; 424/184.1
See application file for complete search history.

(56) References Cited

U.S. PATENT DOCUMENTS

| 3,534,017 | A | 10/1970 | Fujimoto et al. |
| 4,210,746 | A | 7/1980 | Kerr et al. |
| 4,522,811 | A | 6/1985 | Eppstein et al. |
| 5,166,195 | A | 11/1992 | Ecker |
| 5,194,428 | A | 3/1993 | Agrawal et al. |
| 5,264,423 | A | 11/1993 | Cohen et al. |
| 5,271,941 | A | 12/1993 | Cho-Chung |
| 5,292,875 | A | 3/1994 | Stec et al. |
| 5,366,878 | A | 11/1994 | Pederson et al. |
| 5,606,049 | A | 2/1997 | Vaghefi |
| 5,635,377 | A | 6/1997 | Pederson et al. |
| 5,644,048 | A | 7/1997 | Yau |
| 5,646,267 | A | 7/1997 | Stec et al. |
| 5,652,355 | A | 7/1997 | Metelev et al. |
| 5,736,294 | A | 4/1998 | Ecker et al. |
| 5,770,713 | A | 6/1998 | Imbach et al. |
| 6,143,881 | A | 11/2000 | Metelev et al. |
| 6,344,323 | B1 | 2/2002 | Seifert |

(Continued)

FOREIGN PATENT DOCUMENTS

| CA | 2589406 | 6/2006 |
| CN | 1434054 A | 8/2003 |

(Continued)

OTHER PUBLICATIONS

Sioud, M., Advanced Drug Delivery Reviews, vol. 59, pp. 153-163 (2007).*
Schlee et al, Molecular Therapy, vol. 14, No. 4, pp. 463-470 (2006).*
EP 1 920 775.
Absher, et al., *Nature* 223:715-717 (Aug. 16, 1969).
Adam, et al., *Blood*, 106(1):338-344 (2005).
Adelfinskaya, et al., *Angew. Chem. Int. Ed.*, 46:4356-4358 (2007).
Adelfinskaya, et al., *Nucleic Acids Research*, 35(15):5060-5072 (2007).

(Continued)

*Primary Examiner* — Jane Zara
(74) *Attorney, Agent, or Firm* — Leydig, Voit & Mayer, Ltd.

(57) ABSTRACT

The present invention provides an oligonucleotide which is capable of activating RIG-I and inducing an anti-viral, in particular, an IFN, response in cells expressing RIG-I. The present invention further provides an oligonucleotide which is capable of activating RIG-I and which has target gene-silencing activity. The oligonucleotide of the present invention has a double-stranded section of at least 19, preferably at least 21 bp, at least one 5' triphosphate, and at least one blunt end which bears a 5' triphosphate. The present invention further provides the use said oligonucleotide for inducing an anti-viral, in particular, an IFN, response in vitro and in vivo. The present invention additionally provides the use of said oligonucleotide for preventing and/or treating diseases or conditions such as infections, tumors/cancers, and immune disorders.

20 Claims, 35 Drawing Sheets

(56) References Cited

U.S. PATENT DOCUMENTS

| | | |
|---|---|---|
| 6,346,614 B1 | 2/2002 | Metelev et al. |
| 6,369,209 B1 | 4/2002 | Manoharan et al. |
| 6,737,520 B2 | 5/2004 | Manoharan et al. |
| 6,900,308 B2 | 5/2005 | Wyrzykiewicz et al. |
| 7,119,184 B2 | 10/2006 | Manoharan et al. |
| 7,217,807 B2 | 5/2007 | Bentwich |
| 7,285,658 B2 | 10/2007 | Cook et al. |
| 7,371,735 B2 | 5/2008 | Harel-Bellan et al. |
| 7,598,230 B2 | 10/2009 | Cook et al. |
| 7,696,334 B1 | 4/2010 | Bentwich |
| 7,696,342 B1 | 4/2010 | Bentwich |
| 7,759,478 B1 | 7/2010 | Bentwich |
| 7,790,867 B2 | 9/2010 | Bentwich |
| 7,807,653 B2 | 10/2010 | Cook et al. |
| 7,862,816 B2 | 1/2011 | Krasnoperov et al. |
| 8,563,709 B2 | 10/2013 | Iba et al. |
| 8,912,158 B2 | 12/2014 | Dimmeler et al. |
| 2008/0664786 | 6/1996 | Agrawal |
| 2003/0129615 A1 | 7/2003 | Wyrzykiewicz et al. |
| 2003/0171570 A1 | 9/2003 | Schweitzer |
| 2003/0203868 A1 | 10/2003 | Bushman |
| 2004/0059104 A1 | 3/2004 | Cook et al. |
| 2004/0234999 A1 | 11/2004 | Farrar et al. |
| 2004/0261149 A1 | 12/2004 | Fauquet et al. |
| 2005/0026861 A1 | 2/2005 | Kandimalla et al. |
| 2005/0182005 A1 | 8/2005 | Tuschl et al. |
| 2005/0222060 A1 | 10/2005 | Bot et al. |
| 2005/0249736 A1 | 11/2005 | Krasnoperov et al. |
| 2006/0035815 A1 | 2/2006 | Chen et al. |
| 2006/0178334 A1* | 8/2006 | Rossi .................... C12N 15/111 514/44 A |
| 2007/0066521 A1 | 3/2007 | Fauquet |
| 2007/0259832 A1 | 11/2007 | Cook et al. |
| 2007/0265220 A1 | 11/2007 | Rossi et al. |
| 2007/0265224 A1 | 11/2007 | Cook et al. |
| 2007/0287681 A1 | 12/2007 | Jeong et al. |
| 2008/0171712 A1 | 7/2008 | Kandimalla et al. |
| 2008/0188428 A1 | 8/2008 | Bentwich |
| 2008/0250532 A1* | 10/2008 | Abdullah ............. C12Q 1/6897 800/281 |
| 2009/0143327 A1 | 6/2009 | Smolke et al. |
| 2009/0203121 A1 | 8/2009 | Hochberg et al. |
| 2009/0203131 A1* | 8/2009 | Reineke ............... C12N 15/113 435/375 |
| 2009/0203894 A1 | 8/2009 | Liu et al. |
| 2010/0178272 A1 | 7/2010 | Hartmann |
| 2010/0260788 A1* | 10/2010 | Debelak ................ C07H 21/02 424/184.1 |
| 2010/0303859 A1 | 12/2010 | Williams |
| 2011/0130738 A1 | 6/2011 | Schmidt |
| 2011/0165133 A1 | 7/2011 | Rabinovich et al. |
| 2011/0245481 A1 | 10/2011 | Iba et al. |
| 2011/0247091 A1 | 10/2011 | Magor et al. |
| 2012/0225924 A1 | 9/2012 | Lin et al. |
| 2013/0121989 A1 | 5/2013 | Gaertig et al. |
| 2013/0189367 A1 | 7/2013 | Zhang et al. |
| 2013/0302252 A1 | 11/2013 | Zhang et al. |
| 2014/0171368 A1 | 6/2014 | Goepferich et al. |
| 2015/0018407 A1 | 1/2015 | Dimmeler et al. |
| 2016/0369280 A1* | 12/2016 | Rossi .................... C12N 15/111 |

FOREIGN PATENT DOCUMENTS

| | | |
|---|---|---|
| CN | 101088565 A | 12/2007 |
| CN | 101190944 A | 6/2008 |
| CN | 101632833 A | 1/2010 |
| CN | 101974529 A | 2/2011 |
| CN | 102475892 A | 5/2012 |
| DE | 1 695 303 A1 | 4/1972 |
| DE | 41 10 085 A1 | 10/1992 |
| DE | 10 2007 052 114 A1 | 5/2009 |
| EP | 0 021 099 A1 | 1/1981 |
| EP | 0 031 285 A2 | 7/1981 |
| EP | 0 043 075 A2 | 1/1982 |
| EP | 0 081 099 A2 | 6/1983 |
| EP | 0 339 842 A2 | 11/1988 |
| EP | 0 386 563 A1 | 9/1990 |
| EP | 0 415 901 A2 | 3/1991 |
| EP | 0 698 034 B1 | 2/1996 |
| EP | 0 754 188 B1 | 11/1997 |
| EP | 0 788 366 B1 | 12/1999 |
| EP | 0 739 899 B1 | 6/2001 |
| EP | 1 247 815 A2 | 10/2002 |
| EP | 1 493 818 A2 | 1/2005 |
| EP | 1 505 152 A1 | 2/2005 |
| EP | 1 626 086 A2 | 2/2006 |
| EP | 1 637 597 A1 | 3/2006 |
| EP | 1 657 306 A1 | 5/2006 |
| EP | 1 743 901 A2 | 1/2007 |
| EP | 05020019.5 A1 | 3/2007 |
| EP | 05020020.3 A1 | 3/2007 |
| EP | 06016578.4 A1 | 2/2008 |
| EP | 1 939 291 A2 | 7/2008 |
| EP | 2 113 565 A1 | 11/2009 |
| EP | 2 141 234 A1 | 1/2010 |
| EP | 2 207 797 A1 | 7/2010 |
| EP | 1 453 962 B1 | 8/2010 |
| EP | 2 213 738 A2 | 8/2010 |
| EP | 2 284 266 A2 | 2/2011 |
| EP | 2 327 783 A1 | 6/2011 |
| EP | 2 338 449 A1 | 6/2011 |
| EP | 2 338 499 A1 | 6/2011 |
| EP | 1 857 119 B1 | 11/2011 |
| EP | 2 277 508 B1 | 4/2012 |
| EP | 1 969 125 B1 | 6/2012 |
| EP | 2 497 827 A1 | 9/2012 |
| EP | 2 123 757 B1 | 10/2012 |
| EP | 2 508 530 A1 | 10/2012 |
| EP | 2 514 758 A1 | 10/2012 |
| EP | 2 518 150 A2 | 10/2012 |
| EP | 1 920 775 B1 | 12/2012 |
| EP | 2 551 354 A1 | 1/2013 |
| EP | 1 915 448 B1 | 9/2013 |
| EP | 2 671 949 A1 | 12/2013 |
| EP | 1 957 648 B1 | 4/2014 |
| EP | 1 973 574 B1 | 4/2014 |
| EP | 2 712 870 A1 | 4/2014 |
| EP | 2 069 500 B1 | 9/2014 |
| EP | 2 207 787 B1 | 11/2014 |
| EP | 2 492 355 B1 | 4/2015 |
| JP | 0H6-501843 A | 3/1994 |
| JP | 07-099976 A | 4/1995 |
| JP | 08-154687 A | 6/1996 |
| JP | 2003-535043 A | 11/2003 |
| JP | 2005-526778 A | 9/2005 |
| JP | 2006-238795 A | 9/2006 |
| WO | WO 84/00688 A1 | 3/1984 |
| WO | WO 89/08146 A1 | 9/1989 |
| WO | WO 90/14353 A1 | 11/1990 |
| WO | WO 91/06309 A1 | 5/1991 |
| WO | WO 92/02641 A1 | 2/1992 |
| WO | WO 92/03454 A1 | 3/1992 |
| WO | WO 92/17484 A1 | 10/1992 |
| WO | WO 93/07882 A1 | 4/1993 |
| WO | WO 93/08296 A1 | 4/1993 |
| WO | WO 93/23569 A1 | 11/1993 |
| WO | WO 94/02501 A1 | 2/1994 |
| WO | WO 94/15619 A1 | 7/1994 |
| WO | WO 94/17093 A1 | 8/1994 |
| WO | WO 94/24144 A2 | 10/1994 |
| WO | WO 94/26764 A1 | 11/1994 |
| WO | WO 95/03406 A2 | 2/1995 |
| WO | WO 95/32719 A1 | 12/1995 |
| WO | WO 96/02556 A2 | 2/1996 |
| WO | WO 96/07392 A2 | 3/1996 |
| WO | WO 96/18736 A1 | 6/1996 |
| WO | WO 96/19572 A1 | 6/1996 |
| WO | WO 96/40159 A1 | 12/1996 |
| WO | WO 96/41812 A1 | 12/1996 |
| WO | WO 99/55857 A2 | 11/1999 |
| WO | WO 00/66609 A1 | 11/2000 |
| WO | WO 01/16312 A2 | 3/2001 |
| WO | WO 01/22990 A2 | 5/2001 |

(56) References Cited

FOREIGN PATENT DOCUMENTS

| | | |
|---|---|---|
| WO | WO 01/68077 A2 | 9/2001 |
| WO | WO 01/70751 A1 | 9/2001 |
| WO | WO 02/10432 A2 | 2/2002 |
| WO | WO 03/008432 A1 | 1/2003 |
| WO | WO 03/012052 A2 | 2/2003 |
| WO | WO 03/072757 A2 | 9/2003 |
| WO | WO 03/078595 A2 | 9/2003 |
| WO | WO 03/086280 A2 | 10/2003 |
| WO | WO 03/087367 A2 | 10/2003 |
| WO | WO 03/087368 A2 | 10/2003 |
| WO | WO 03/101375 A2 | 12/2003 |
| WO | WO 2004/015062 A2 | 2/2004 |
| WO | WO 2004/020631 A2 | 3/2004 |
| WO | WO 2004/022777 A1 | 3/2004 |
| WO | WO 2004/024063 A2 | 3/2004 |
| WO | WO 2004/044123 A2 | 5/2004 |
| WO | WO 2004/045543 A2 | 6/2004 |
| WO | WO 2004/048511 A2 | 6/2004 |
| WO | WO 2004/061423 A2 | 7/2004 |
| WO | WO 2004/074441 A2 | 9/2004 |
| WO | WO 2004/080418 A2 | 9/2004 |
| WO | WO 2004/080425 A2 | 9/2004 |
| WO | WO 2004/083430 A2 | 9/2004 |
| WO | WO 2004/085623 A2 | 10/2004 |
| WO | WO 2004/106517 A1 | 12/2004 |
| WO | WO 2004/111190 A2 | 12/2004 |
| WO | WO 2005/005632 A2 | 1/2005 |
| WO | WO 2005/076979 A2 | 8/2005 |
| WO | WO 2005/089287 A2 | 9/2005 |
| WO | WO 2005/108573 A2 | 11/2005 |
| WO | WO 2005/117991 A2 | 12/2005 |
| WO | WO 2006/016574 A1 | 2/2006 |
| WO | WO 2006/063252 A2 | 6/2006 |
| WO | WO 2006/074400 A2 | 7/2006 |
| WO | WO 2006/078646 A2 | 7/2006 |
| WO | WO 2006/105361 A2 | 10/2006 |
| WO | WO 2006/110813 A2 | 10/2006 |
| WO | WO 2006/119643 A1 | 11/2006 |
| WO | WO 2006/122409 A1 | 11/2006 |
| WO | WO 2006/128739 A1 | 12/2006 |
| WO | WO 2006/130949 A1 | 12/2006 |
| WO | WO 2007/021142 A1 | 2/2007 |
| WO | WO 2007/030619 A2 | 3/2007 |
| WO | WO 2007/031319 A1 | 3/2007 |
| WO | WO 2007/031322 A1 | 3/2007 |
| WO | WO 2007/038788 A2 | 4/2007 |
| WO | WO 2007/051303 A1 | 5/2007 |
| WO | WO 2007/107304 A2 | 9/2007 |
| WO | WO 2008/017473 A2 | 2/2008 |
| WO | WO 2008/045576 A2 | 4/2008 |
| WO | WO 2008/076127 A1 | 6/2008 |
| WO | WO 2008/080091 A2 | 7/2008 |
| WO | WO 2008/087641 A2 | 7/2008 |
| WO | WO 2008/087642 A2 | 7/2008 |
| WO | WO 2008/099396 A1 | 8/2008 |
| WO | WO 2008/124165 A2 | 10/2008 |
| WO | WO 2008/131807 A2 | 11/2008 |
| WO | WO 2008/134593 A1 | 11/2008 |
| WO | WO 2009/018506 A2 | 2/2009 |
| WO | WO 2009/038707 A2 | 3/2009 |
| WO | WO 2009/046541 A1 | 4/2009 |
| WO | WO 2009/051659 A2 | 4/2009 |
| WO | WO 2009/056116 A1 | 5/2009 |
| WO | WO 2009/060124 A2 | 5/2009 |
| WO | WO 2009/060281 A2 | 5/2009 |
| WO | WO 2009/061417 A1 | 5/2009 |
| WO | WO 2009/064590 A2 | 5/2009 |
| WO | WO 2009/068677 A1 | 6/2009 |
| WO | WO 2009/083738 A2 | 7/2009 |
| WO | WO 2009/141146 A1 | 11/2009 |
| WO | WO 2009/146556 A1 | 12/2009 |
| WO | WO 2009/151600 A2 | 12/2009 |
| WO | WO 2010/028079 A2 | 3/2010 |
| WO | WO 2010/042742 A2 | 4/2010 |
| WO | WO 2010/042749 A2 | 4/2010 |
| WO | WO 2010/042751 A2 | 4/2010 |
| WO | WO 2010/042755 A2 | 4/2010 |
| WO | WO 2010/047216 A1 | 4/2010 |
| WO | WO 2010/062502 A1 | 6/2010 |
| WO | WO 2010/099161 A1 | 9/2010 |
| WO | WO 2010/118263 A1 | 10/2010 |
| WO | WO 2010/120874 A2 | 10/2010 |
| WO | WO 2010/136192 A1 | 12/2010 |
| WO | WO 2010/147655 A2 | 12/2010 |
| WO | WO 2011/008857 A1 | 1/2011 |
| WO | WO 2011/011716 A1 | 1/2011 |
| WO | WO 2011/028218 A1 | 3/2011 |
| WO | WO 2011/064130 A1 | 6/2011 |
| WO | WO 2011/133559 A2 | 10/2011 |
| WO | WO 2011/138328 A2 | 11/2011 |
| WO | WO 2011/140285 A2 | 11/2011 |
| WO | WO 2012/056449 A2 | 5/2012 |
| WO | WO 2012/056457 A2 | 5/2012 |
| WO | WO 2012/091523 A2 | 7/2012 |
| WO | WO 2012/125987 A2 | 9/2012 |
| WO | WO 2012/130886 A1 | 10/2012 |
| WO | WO 2013/003887 A1 | 1/2013 |
| WO | WO 2013/013820 A1 | 1/2013 |
| WO | WO 2013/020986 A1 | 2/2013 |
| WO | WO 2013/053480 A1 | 4/2013 |
| WO | WO 2013/053481 A1 | 4/2013 |
| WO | WO 2013/075140 A1 | 5/2013 |
| WO | WO 2013/153082 A1 | 10/2013 |
| WO | WO 2014/049079 A1 | 4/2014 |
| WO | WO 2014/124433 A1 | 8/2014 |

OTHER PUBLICATIONS

Algner, et al., *J. Biomed. Biotechnol*.2006(4):71659 (2006).
Akira, et al., *C R Biol*. 327(6):581-9 (2004).
Aleman, et al., *RNA* 13(3):385-395 (Mar. 2007).
Alexopoulou, et al., *Nature*, 413(6857):732-8 (2001).
Ambion, Life Technologies Corporation, Catalog Nos. AM1330, AM1333, AM1334, AM1338, Publ. No. 1330M, Revision G. (2012).
Andrejeva, et al., *Proc Natl Acad Se; USA*, 101:17264-9 (Dec. 7, 2004).
Arnold, et al., *J.Biol.Chem*., 274(5)1 706-2716 (1999).
Bartenschlager, et al., *J. Gen. Virol*.,81:1631-1648 (2000).
Barton, et al., *Nat Immunol* 7:49-56 (Jan. 2006).
Bass, et al., *Cell* 55(6)1 089-98 (1988).
Baudin, et al., *EMBO J*., 13(13):3158-3166 (D34) (1994).
Behlke, et al., *Mol Ther*, 13(4):644-670 (Apr. 2006).
Bekeredjian-Ding, et al., *J Immunol* ,174: 4043-50 (Apr. 1, 2005).
Besch, et al., *Cell Death Differ*, 14:818-29 (2007).
Blackburn, et al., *J.C.S. Chem. Commun*., 1188-1190 (1981).
Blumberg, et al., *Cell*, 23(3):837-45 (Mar. 1981).
Blumberg, et al., *J Virol*., 40(2):568-76 (Nov. 1981).
Bonin, et al., *RNA*, 6:563-570 (2000).
Bowie, et al., *Trends in Immunology*, 28(4):147-150 (2007).
Brownlee, et al., *Nucleic Acids Research*, 23(14):2641-2647 (1995).
Brzozka, et al. *Journal of Virology*, 80:2675-83 (Mar. 2006).
Brzozka, et al., *Journal of Virology*, 79:7673-81 (Jun. 2005).
Bui, et al., *Curr. Opin. Immunol*., 19:203-8 (2007).
Carroll, et al. *Methods in Enzymology*, 275:365-382 (1996).
Cazenave, et al., *Proc. Natl. Acad. Sci. USA*, 91:6672-6976 (1994).
Chang et al., *Microbes and Infection* 8, 157 (2006).
Chaperot, et al., *The Journal of Immunology*, 176:248-255 (2006).
Chawla-Sarkar, et al., *Cell Death and Differentiation*, 11:915-923 (2004).
Chemicool, "Definition of Homogeneous," in *Chemicool* (2014). Retrieved on Jan. 25, 2015 from www.chemicool.com/definition/homogeneous.html.
Chen, et al., *J Virol*., 81(2):964-76 (2007).
Cheong, et al., *Nucleic Acids Res*, 24(21):4197-4201 (D35) (1996).
Chien, et al., *Cancer Gene Therapy*, 12(3):321-328 (2005).
Chiocca, *Nat Rev Cancer*, 2:938-950 (2002).
Coe, et al., *J. Chem. Soc., Chem. Commun*., 312-314 (1991).
Coffey, et al., *Science*, 282:1332-1334 (1998).
Colonno, et al., *Cell*, 15:93-101 (1978).

(56) References Cited

OTHER PUBLICATIONS

Cuesta, *J Immunol.*, 178(6):3602-11 (2007).
Cui, et al. *Molecular Cell*, 29:169-179 (2008).
Cullen, *Mol Cell*, 16:861-5 (Dec. 22, 2004).
Curiel, *J. Clin. Invest.*, 117:1167-74 (2007).
Danial, et al., *Cell*, 116:205-19 (2004).
Davis, et al., *PNAS*, 101(29)1 0697-10702 (Jul. 20, 2004).
De Fougerolles, et al., *J. Nat.Rev.Drug Discov.*, 6:443-53 (2007).
De Jonge, et al., *Gene Therapy*, 13:400-411 (2006)).
Decatur, et al., *J. Biol. Chem.*, 278:695-8 (Jan. 3, 2003).
Delale, et al., *J Immunol*, 175:6723-32 (Nov. 15, 2005).
Der, et al, *Proc Natl Acad Sci USA*, 92:8841-5 (Sep. 12, 1995).
Diebold, et al., *Nature*, 424:324-8 (Jul. 17, 2003).
Diebold, et al., *Science*, 303:1529-31 (Mar. 5, 2004).
Duan, et al., *Antiviral Therapy*, 13(1):109-114 (2008).
Dunn, et al., *J Mol Biol*, 166:477-535 (Jun. 5, 1983).
Elbashir, et al., *Nature*, 411:494-498 (May 24, 2001).
Elbashir, et al., *The EMBO Journal*, 20(23):6877-6888 (2001).
Entry „Influenca A virus in Wikipedia.
Entry „Oligonucleotide synthesis in Wikipedia.
Fromont-Racine, et al., *Gene*, 313:17-42 (Aug. 14, 2003).
Furuichi, et al., *Adv Virus Res*, 55:135-84 (2000).
Gaur, et al., *Tetrahedron Letters*, 33:3301-3304 (1992).
GenBank Acc No. AF389115.1 (Sep. 19, 2002) Influenza A virus (A/Puerto Rico/8/34/Mount Sinai (H1N1 >>, segment 1, complete sequence (see first nucleotide, Pos. 1) (D15).
GenBank Acc No. AF389116.1 (Sep. 19, 2002) Influenza A virus (A/Puerto Rico/8/34/Mount Sinai (H1N1)), segment 2, complete sequence (see first nucleotide, Pos. 1) (D16).
GenBank Acc No. AF389117.1 (Sep. 19, 2002) Influenza A virus (A/Puerto Rico/8/34/Mount Sinai (H1N1)), segment 3, complete sequence (see first nucleotide, Pos. 1) (D17).
GenBank Acc No. AF389118.1 (Sep. 19, 2002) Influenza A virus (A/Puerto Rico/8/34/Mount Sinai (H1N1)), segment 4, complete sequence (see first nucleotide, Pos. 1) (D18).
GenBank Acc No. AF389119.1 (Sep. 19, 2002) Influenza A virus (A/Puerto Rico/8/34/Mount Sinai (H1N1)), segment 5, complete sequence (see first nucleotide, Pos. 1) (D19).
GenBank Acc No. AF389120.1 (Sep. 19, 2002) Influenza A virus (A/Puerto Rico/8/34/Mount Sinai (H1N1)), segment 6, complete sequence (see first nucleotide, Pos. 1) (D20).
GenBank Acc No. AF389121.1 (Sep. 19, 2002) Influenza A virus (A/Puerto Rico/8/34/Mount Sinai (H1N1)), segment 7, complete sequence (see first nucleotide, Pos. 1) (D21).
GenBank Acc No. AF389122.1 (Sep. 19, 2002) Influenza A virus (A/Puerto Rico/8/34/Mount Sinai (H1N1)), segment 8, complete sequence (see first nucleotide, Pos. 1) (D22).
GenBank Acc. No. AF221499.1 (Mar. 9, 2001) Japanese encephalitis virus, isolate CH2195LA, complete genome (see first nucleotide, Pos. 1) (D14).
GenBank Acc. No. J02428.1 (Oct. 21, 2002) Vesicular stomatitis Indiana virus, complete genome (see first nucleotide, Pos. 1) (D13).
Gerber, et al., *Trends Biochem Sci*, 26(6):376-84 (2001).
Gerrits, Digital dissertation, FU Berlin, 2001, English Abstract.
Gitlin, et al., *Proc Natl Acad Sci USA*, 103(22):8459-64 (2006).
Goldeck, et al., *Angew. Chem.*, 126(4):782-786 (2014).
Gondai, et al., *Nucleic Acids Res*, 36(3):e18 (2008).
Grzelinski, et al., *Hum Gene Ther.*, 17(7):751-66 (2005).
Haas, et al., *Immunity*,28:315-232 (2008).
Hanahan, et al., *Cell*, 100:57-70 (2000).
Hartmann, et al., *Handbook of RNA Biochemistry*, pp. 6, 39, 43 (2005).
Heil, et al., *Science*, 303:526-9 (Mar. 5, 2004).
Helm, et al., *RNA*, 5:618-621 (1999).
Hemmi, et al., *Nat Immunol*, 3:196 (Feb. 2002).
Hemmi, et al., *Nature*, 408:740-5 (Dec. 7, 2000).
Henry, et al., *J Exp Med* 204(5):987-94 (2007).
Hofacker, et al., *Bioinformatics*, 20:1495-1499 (2004).
Holý, et al., *Collect. Czech. Commun.*, 47:3447-3463 (1982).
Honda, et al., *Virus Res*, 55: 199-206 (Jun. 1998).
Hornung, et al., *J Immunol*, 168:4531-7 (May 1, 2002).
Hornung, et al., *Nat Med*, 11(3):263-70 (Mar. 2005).
Hornung, et al., *Science*, 314:994-997 (2006).
Hsu, et al., *Croc.Natl.Acad.Sci.U.S.A.*, 84:8140-8141 (1987).
Huang, et al., *Biochemistry*, 39 (50):15548-15555 (2000).
Ishii, et al., *Nat Immunol*, 7:40-8 (Jan. 2006).
Jiang, et al., *Genes & Dev*, 17:832-837 (2003).
Judge, et al., *Nat Biotechnol*, 23:457-462 (2005).
Kamphuis, et al., *Blood*, 108:3253-61 (2006).
Kanneganti, et al. *Nature*, 440 (7081):233-6 (2006).
Kao, et al., *Virology*, 287:251-260 (2001).
Kariko, et al., *Biochem. Biophys. Res. Commun.*, 128(2):695-698 (1985).
Kariko, et al., *Immunity*, 23:165-75 (Aug. 2005).
Kato, et al., *Immunity*, 23(1):19-28 (Jul. 2005).
Kato, et al., *Nature*, 441 (7089):101-105 (Apr. 9, 2006).
Kawai, et al., *Nat Immunol*, 6(10):981-988 (Oct. 2005).
Kawai, et al., *Nat Immunol*, 7(2):131-7 (2006).
Kennedy, et al., *J.Mol.Biol.*, 370:256-268 (2007).
Khan, et al., *J Drug Target*, 12(6):393-404 (2004).
Kim, et al., *Nat Biotechnol*, 22:321-325 (Mar. 2004).
Knorre, et al., *FEBS Letters*, 70(1)1 05-108 (1976).
Koh, et al., *J. Med. Chem.*, 48:2867-2875 (2005).
Kossen, et al. *Chemistry and Biology*, 11:807-815 (2004).
Krieg, *Annu Rev Immunol*, 20:709-60 (2002).
Krieg, et al., *Nature*, 374:546-9 (Apr. 6, 1995).
Krug, et al., *Eur J Immunol*, 31:2154-63 (Jul. 2001).
Krug, et al., *Immunity*, 21:107-19 (Jul. 2004).
Krupp, *Gene*, 72:75-89 (1988).
Kuzmine, et al., *The Journal of Biol. Chem.*, 278(5):2819-2823 (2003).
Latz, et al., *Nat Immunol*, 5 (2):190-8 (2004).
Latz, et al., *Nat. Immunol*, 8:772-779 (2007).
Lau, et al. *J Exp Med*, 202 (9):1171-7 (2005).
Lebedev, et al., *Nucleosides, Nucleotides and Nucleic Acids*, 20(4-7):1403-1409 (2001).
Lee, et al., *Proc Natl Acad Sci USA*, 74:59-63 (Jan. 1977).
Limbach, et al., *Nucleic Acids Res*, 22:2183-2196 (1994).
Loo, et al., *J Virol*, 82:335-345 (2008).
Lu, et al., *Nucleic Acids Res*, 39(4):1565-1575 (Mar. 2011).
Ludwig, *Acta Biochim Biophys Acad Sci Hung*, 16:131-3 (1981).
Ludwig, et al., *J. Org. Chem.*, 54:631-635 (1989).
Ludwig, et al., *J. Org. Chem.*, 56:1777-1783-D9 (1991).
Ma, et al., *Molecular Therapy—Nucleic Acids*, 3(e161):1-11 (2014).
Maitra, et al., *PNAS*, 77(7):3908-3911 (1980).
Marques, et al., *Nat Biotechnol*, 24(5):559-565 (May 2006).
Matsumoto, et al., *J Immunol*, 171(6):3154-62 (2003).
McGill, et al., *Cell*, 109:707-18 (2002).
Meister, et al., *Mol Cell*, 15:185 (Jul. 23, 2004).
Melchjorsen, et al., *J Virol*, 79:12944-51 (2005).
Meyer, et al., *Methods in Molecular Biol*, 1086:21-40 (2014).
Meylan, et al., *Nature*, 437(7062):1167-72 (Oct. 20, 2005).
Miller, et al., *N.Engl.J.Med.* 355:51-65 (2006).
Milligan, et al., *Dep. Of Chem. And Biochem*, 15(21):8783-98 (1987).
Milligan, et al., *Methods in Enzymology, RNA Processing, Part A General Methods*, p. 51-62 (1987).
Minakuchi, et al., *Nucleic Acids Research*, 32(13):e109 (2004).
Mocikat, et al., *Immunity*, 19:516-569 (Oct. 2003).
Muller, et al., *Science*, 264:1918-21 (1994).
Neumann, et al., *Curr. Topics in•Microbiol. and Immunol.*, 283:121-43 (2004).
Nishiya, et al, *J Biol Chem*, 279(18):19008-17 (2004).
Obeid, et al., *Nat.Med.*, 13:54-61 (2007).
Olsen, et al., *Journal of Biological Chemistry*, 271(13):7435-7439 (1996).
Palladino, et al., *Cell*, 102(4):437-49 (2000).
Paul, et al. *Chemistry and Biology*, 13:329-338 (2006).
Pearse, et al., *Adv Drug Deily Rev*, 57(3):465-474 (Jan. 10, 2005).
Pei et al., *Nat. Methods*, 3:670-6 (2006).
Peterli, et al., *Helvetica Chimica Acta*, 75:696-706 (1992).
Phuangsab, et al., *Cancer Lett*, 172:27-36 (2001).
Pichlmair, et al., *Science*, 314:997-1001 (2006).

(56) References Cited

OTHER PUBLICATIONS

Plumet, et al., *PLoS ONE*, 3(e29):1-10 (2007).
Poeck, et al., *Blood*, 103(8):3058-3064 (Apr. 2004) (www.bloodjournal.org/cgi/content/full/103/8/3058#REF4).
Poeck, et al., *Nature Medicine*, 14(11):1256-1262 (2008).
Portela, et al., *J. Gen. Virol.*, 2992(83):723-734 (2002).
Radecke, et al., *Embo J*, 14:5773-84 (Dec. 1, 1995).
Ranjith-Kumar, et al., *J. Virol.*, 76(24):12526-12536 (2002).
Ranjith-Kumar, et al., *RNA*, 12:303-312 (2006).
Reynolds, et al., *Nat Biotechnol*, 22:326-30 (2004).
Roempp, Sequenzhomologie, Georg Thieme Verlag KG, https://roempp.thieme.de/roempp4.0/do/data/RD-19.01964.
Rohayem, et al., *Journal of Virology*, 80(14):7060-7069 (2006).
Rosa, et al., *Molecular and Cellular Biology*, 1(9):785-796 (Sep. 1981).
Rossi, *Gene Therapy* 13:583-584 (2006).
Rothenfusser, et al., *J•Immunol*, 175:5260-8 (Oct. 15, 2005).
Rozenski, et al., *Nucleic acids research*, 27:196-97 (Jan. 1, 1999).
Rubin, et al, *Lancet*, 369:1731-41 (2007).
Ru Dd, et al., *J Immunol*, 176:1937-42 (Feb. 1, 2006).
Russell, *Cancer Gene Ther*, 9:961-966 (2002).
Samanta, et al., *The EMBO Journal*, 25:4207-4214 ( Aug. 2006).
Schlee, et al., *Immunity*, 31:25-34 (2009).
Schlee, et al., *CTMI*, 316:207-230 (2007).
Schlee, et al., *Mol Ther*, 18(7):1254-1262 (2010).
Schlee, et al., *Molecular Therapy*, 14(4):463-470 (2006).
Schmidt, et al., *PNAS*, 106(29):12067-12072 (2009).
Schnell, et al., *EMBO J*, 13(18):4195-4203 (1994).
Schoatzau, et al., *Chem. Commun.*, 3:387-388 (1996).
Selisko, et al., *Virology*, 351(1):145-158 (2006).
Seth, et al., *Cell*, 122(5):669-82 (Sep. 9, 2005).
Shatkin, et al., *Nat Struct Biol*, 7(10):838-42 (Oct. 2000).
Singh, et al., *PNAS USA*,86:8280-3 (Nov. 1989).
Sioud, *Advanced Drug Delivery Reviews*, 59(2-3):153-163 (2007).
Sioud, et al., *Biochem Biophys Res Commun*, 312(4):1220-1225 (2003).
Sioud, et al., *J Mol Biol*, 348:1079-1090 (2005).
Sioud, *Eur J Immunol*, 36(5):1222-30 (2006).
Soutschek, et al., *Nature*, 432(7014):173-178 (Nov. 2004).
Sproat, et al., *Nucleic acids research*, 27(8):1950-1955 (1999).
Stetson, et al., *J.Exp.Med.* 203:1837-41 (2006).
Stojdl, et al., *Nat Med*, 6:821-825 (2000).
Strahle, et al., *Virology*, 351(1):101-11 (2006).
Stump, et al., *Nucleic Acids Research*, 21(23):5480-5484 (1993).
Sugiyama, et al., *J Immunol*, 174:2273-2279 (2005).
Sumpter, Jr., et al., *J Virol* 79, 2689 (Mar. 2005).
Tabeta, et al., *Proc Natl Acad Sci USA*, 101:3516-21 (Mar. 9, 2004).
Takahasi, et al., *Molecular Cell*, 29:428-440 (Feb. 29, 2008).
Tormo, et al., *Am J Pathol*, 169:665-72 (2006).
Tormo, et al., *Cancer Res.*, 66:5427-35 (2006).
Tschoep, et al., *J Mol Med*, 79:306-13 (2001).
Tschopp, et al., *Nature Reviews*, 4:95-104 (Feb. 2003).
Uno, et al., *Nat.Med.*, 12:693-8 (2006).
Urban-Klein, et al., *Gene Therapy*, 12(5):461-466 (2005).
Van Dijk, et al., *J. Gen. Virol.*, 85:1077-1093 (2004).
Van Dijk, et al., *Virology*, 211:320-323 (1995).
Van Holten, et al., *Arthritis Research*, 4:346-352 (2002).
Vollmer, et al., *Antisense Nucleic Acid Drug Dev*, 12:165-75 (Jun. 2002).
Wagner, et al., ROEMPP Online, Version 3.36, catchword "Lipofektion" (= engl. "lipofection").
Walther, et al., *Drugs*, 60(2):249-271 (Aug. 2000).
Wang, et al., *J Med Chem.* 47:6902-6913 (2004).
Wang, et al., *Nat Struct & Mol Biol*, 17(7):781-787 (Jul. 2010).
Weber, et al., *J Virol*, 80(10):5059-64 (May 2006).
Whelan, et al., *Curr. Topics in Microbiol. and Immunol.*, 283:61-119 (2004).
Wu, et al., *Brain Research*, 1008(2):284-287 (May 22, 2004).
Xiao, et al., *Annual review of biochemistry*, 71:165-89 (2002).
Xu, et al., *Mol Cell.* 19(6):727-40 (Sep. 16, 2005.
Yang, et al., *Embo J*, 14(24):6095-6106 (Dec. 15, 1995).
Yang, et al., *Immunity*, 23(5):465-78 (Nov. 2005).
Yoneyama, et al., *Nat. Immunol.*, 5(7):730-737 (Jul. 2004).
Yoneyama, et al., *J. Biol.Chem.*, 282:15315-8 (2007).
Yoneyama, et al., *Journal of Immunlogy*, 175:2851-2858 (2005).
Yount, et al., *Archives Of Biochemistry And Biophysics*, 113:288-295 (1966).
Zeh, et al., *Cancer Gene Ther*, 9:1001-1012 (2002).
Zimmermann, et al., *Nature*, 441(7089):111-114 (May 2006).
Zlatev, et al., *ORG LETT*, 12(10):2190-2193 (2010).
Gantier et al., "The response of mammalian cells to double-stranded RNA," *Cytokine & Growth Factor Reviews*, 18: 363-371 (2007).
Pleiss et al., "T7 RNA polymerase produces 5' end heterogeneity during in vitro transcription from certain templates," *RNA*, 4: 1313-1317 (1998).
Behlke & Devor, "Chemical Synthesis of Oligonucleotides," White Paper, Integrated DNA Technologies, pp. 1-12 (2005).
Fruscoloni et al., "Exonucleolytic degradation of double-stranded RNA by an activity in *Xenopus laevis* germinal vesicles," *PNAS*, vol. 100, No. 4, pp. 1639-1644 (2003).
Fullerton et al., "Structural and Functional Characterization of Sapovirus RNA-Dependent RNA Polymerase," *Journal of Virology*, vol. 81, No. 4, pp. 1858-1871 (Feb. 2007).
Habjan et al., "Processing of Genome 5' Termini as a Strategy of Negative-Strand RNA Viruses to Avoid RIG-I-Dependent Interferon Induction," *PLoS ONE*, vol. 3, No. 4, e2032, pp. 1-8 (2008).
Kim & Rossi, "Strategies for silencing human disease using RNA interference," *Nature Reviews Genetics*, vol. 8, pp. 173-184 (2007).
Rohayem et al., "Characterization of norovirus $3D^{pol}$ RNA-dependent RNA polymerase activity and initiation of RNA synthesis," *Journal of General Virology*, vol. 87, pp. 2621-2630 (2006).
Saito et al., "Regulation of innate antiviral defenses through a shared repressor domain in RIG-I and LGP2," *PNAS*, vol. 104, No. 2, pp. 582-587 (2007).
Soukup & Breaker, "Relationship between internucleotide linkage geometry and the stability of RNA," *RNA*, vol. 5, pp. 1308-1325 (1999).
Straehle et al., "Activation of the Beta Interferon Promoter by Unnatural Sendai Virus Infection Requires RIG-I and Is Inhibited by Viral C Proteins," *Journal of Virology*, vol. 81, No. 22, pp. 12227-12237 (2007).
Vilfan et al., "An RNA toolbox for single-molecule force spectroscopy studies," *Nucleic Acids Research*, vol. 35, No. 19, pp. 6625-6639 (2007).
Chawla-Sarkar et al., "Apoptosis and interferons: Role of interferon-stimulated genes as mediators of apoptosis," *Apoptosis 8(3)*: 237-249 (2003).
Scheel et al., "Toll-like receptor-dependent activation of several human blood cell types by protamine-condensed mRNA," *Eur. J. Immunol.* 35: 1557-1566 (2005).
Sledz & Williams, "RNA interference in biology and disease," *Blood* 106(3): 787-794 (2005).

(56) References Cited

OTHER PUBLICATIONS

Carpick et al., "Characterization of the Solution Complex between the Interferon-induced, Double-stranded RNA-activated Protein Kinase and HIV-I Transactivating Region", *Journal of Biological Chemistry*, 272(14): 9510-9516 (1997).

Meurs et al., "Molecular Cloning and Characterization o fthe Human Double-Stranded RNA-Activated Protein Kinase Induced by Interferon", *Cell*, 62: 379-390 (1990).

Rehwinkel et al., "RIG-I Detects Viral Genomic RNA during Negative-Strand RNA Virus Infection", *Cell* 140: 397-408 (2010).

* cited by examiner

```
Primer      CTATATGCCCCAGCATGAGGCCTCTGTTTGATTCTCC
            |||||| |||||||||||||
2.2-siRNA         GCAUGCGACCUCUGUUGA Amino acid (AA)   Ser Met Arg Pro Leu Phe Asp
AA-Position       202 203 204 205 206 207 208
```

Figure 31

```
                        SEQUENCE LISTING

<160> NUMBER OF SEQ ID NOS: 91

<210> SEQ ID NO 1
<211> LENGTH: 23
<212> TYPE: RNA
<213> ORGANISM: Artificial Sequence
<220> FEATURE:
<223> OTHER INFORMATION: synthetic

<400> SEQUENCE: 1
gggggggggg gaaaaaaaaa aaa                                           23

<210> SEQ ID NO 2
<211> LENGTH: 24
<212> TYPE: RNA
<213> ORGANISM: Artificial Sequence
<220> FEATURE:
<223> OTHER INFORMATION: synthetic

<400> SEQUENCE: 2
ggggcugacc cugaaguuca ucuu                                          24

<210> SEQ ID NO 3
<211> LENGTH: 20
<212> TYPE: DNA
<213> ORGANISM: Artificial Sequence
<220> FEATURE:
```

<223> OTHER INFORMATION: synthetic

<400> SEQUENCE: 3
gggggacgat cgtcggggggg                                                      20

<210> SEQ ID NO 4
<211> LENGTH: 27
<212> TYPE: RNA
<213> ORGANISM: Artificial Sequence
<220> FEATURE:
<223> OTHER INFORMATION: synthetic

<400> SEQUENCE: 4
aagcugaccc ugaaguucau cugcacc                                               27

<210> SEQ ID NO 5
<211> LENGTH: 27
<212> TYPE: RNA
<213> ORGANISM: Artificial Sequence
<220> FEATURE:
<223> OTHER INFORMATION: synthetic

<400> SEQUENCE: 5
ggugcagaug aacuucaggg ucagcuu                                               27

<210> SEQ ID NO 6
<211> LENGTH: 29
<212> TYPE: RNA
<213> ORGANISM: Artificial Sequence
<220> FEATURE:
<223> OTHER INFORMATION: synthetic

<400> SEQUENCE: 6
gcugacccug aaguucaucu gcaccacuu                                             29

<210> SEQ ID NO 7
<211> LENGTH: 27
<212> TYPE: RNA
<213> ORGANISM: Artificial Sequence
<220> FEATURE:
<223> OTHER INFORMATION: synthetic

<400> SEQUENCE: 7
guggugcaga ugaacuucag ggucagc                                               27

<210> SEQ ID NO 8
<211> LENGTH: 24
<212> TYPE: RNA
<213> ORGANISM: Artificial Sequence
<220> FEATURE:
<223> OTHER INFORMATION: synthetic

<400> SEQUENCE: 8
aacacacaca cacacacaca cuuu                                                  24

<210> SEQ ID NO 9
<211> LENGTH: 24
<212> TYPE: RNA
<213> ORGANISM: Artificial Sequence
<220> FEATURE:
<223> OTHER INFORMATION: synthetic

<400> SEQUENCE: 9
gacacacaca cacacacaca cuuu                                                  24

-continued

```
<210> SEQ ID NO 10
<211> LENGTH: 24
<212> TYPE: RNA
<213> ORGANISM: Artificial Sequence
<220> FEATURE:
<223> OTHER INFORMATION: synthetic

<400> SEQUENCE: 10
cacacacaca cacacacaca cuuu                                              24

<210> SEQ ID NO 11
<211> LENGTH: 24
<212> TYPE: RNA
<213> ORGANISM: Artificial Sequence
<220> FEATURE:
<223> OTHER INFORMATION: synthetic

<400> SEQUENCE: 11
uacacacaca cacacacaca cuuu                                              24

<210> SEQ ID NO 12
<211> LENGTH: 26
<212> TYPE: RNA
<213> ORGANISM: Artificial Sequence
<220> FEATURE:
<223> OTHER INFORMATION: synthetic

<400> SEQUENCE: 12
aaagugugug ugugugugug uguugu                                            26

<210> SEQ ID NO 13
<211> LENGTH: 25
<212> TYPE: RNA
<213> ORGANISM: Artificial Sequence
<220> FEATURE:
<223> OTHER INFORMATION: synthetic

<400> SEQUENCE: 13
aaagugugug ugugugugug uguug                                             25

<210> SEQ ID NO 14
<211> LENGTH: 26
<212> TYPE: RNA
<213> ORGANISM: Artificial Sequence
<220> FEATURE:
<223> OTHER INFORMATION: synthetic

<400> SEQUENCE: 14
aaaaagugug ugugugugug uguguu                                            26

<210> SEQ ID NO 15
<211> LENGTH: 25
<212> TYPE: RNA
<213> ORGANISM: Artificial Sequence
<220> FEATURE:
<223> OTHER INFORMATION: synthetic

<400> SEQUENCE: 15
aaaagugugu gugugugugu guguu                                             25

<210> SEQ ID NO 16
<211> LENGTH: 24
<212> TYPE: RNA
<213> ORGANISM: Artificial Sequence
<220> FEATURE:
<223> OTHER INFORMATION: synthetic
```

-continued

<400> SEQUENCE: 16
aaagugugug ugugugugug uguu          24

<210> SEQ ID NO 17
<211> LENGTH: 23
<212> TYPE: RNA
<213> ORGANISM: Artificial Sequence
<220> FEATURE:
<223> OTHER INFORMATION: synthetic

<400> SEQUENCE: 17
aagugugugu gugugugugu guu          23

<210> SEQ ID NO 18
<211> LENGTH: 21
<212> TYPE: RNA
<213> ORGANISM: Artificial Sequence
<220> FEATURE:
<223> OTHER INFORMATION: synthetic

<400> SEQUENCE: 18
gugugugugu gugugugugu u          21

<210> SEQ ID NO 19
<211> LENGTH: 20
<212> TYPE: RNA
<213> ORGANISM: Artificial Sequence
<220> FEATURE:
<223> OTHER INFORMATION: synthetic

<400> SEQUENCE: 19
ugugugugug uguguguguu          20

<210> SEQ ID NO 20
<211> LENGTH: 19
<212> TYPE: RNA
<213> ORGANISM: Artificial Sequence
<220> FEATURE:
<223> OTHER INFORMATION: synthetic

<400> SEQUENCE: 20
gugugugugu gugugugu          19

<210> SEQ ID NO 21
<211> LENGTH: 17
<212> TYPE: RNA
<213> ORGANISM: Artificial Sequence
<220> FEATURE:
<223> OTHER INFORMATION: synthetic

<400> SEQUENCE: 21
gugugugugu gugugu          17

<210> SEQ ID NO 22
<211> LENGTH: 15
<212> TYPE: RNA
<213> ORGANISM: Artificial Sequence
<220> FEATURE:
<223> OTHER INFORMATION: synthetic

<400> SEQUENCE: 22
gugugugugu guguu          15

<210> SEQ ID NO 23
<211> LENGTH: 13

```
<212> TYPE: RNA
<213> ORGANISM: Artificial Sequence
<220> FEATURE:
<223> OTHER INFORMATION: synthetic

<400> SEQUENCE: 23
gugugugugu guu                                                          13

<210> SEQ ID NO 24
<211> LENGTH: 26
<212> TYPE: RNA
<213> ORGANISM: Artificial Sequence
<220> FEATURE:
<223> OTHER INFORMATION: synthetic

<400> SEQUENCE: 24
aaagugugug ugugugugug ugcgu                                             26

<210> SEQ ID NO 25
<211> LENGTH: 25
<212> TYPE: RNA
<213> ORGANISM: Artificial Sequence
<220> FEATURE:
<223> OTHER INFORMATION: synthetic

<400> SEQUENCE: 25
aaagugugug ugugugugug ugucg                                             25

<210> SEQ ID NO 26
<211> LENGTH: 26
<212> TYPE: RNA
<213> ORGANISM: Artificial Sequence
<220> FEATURE:
<223> OTHER INFORMATION: synthetic

<400> SEQUENCE: 26
aaaaagugug ugugugugug uguguc                                            26

<210> SEQ ID NO 27
<211> LENGTH: 25
<212> TYPE: RNA
<213> ORGANISM: Artificial Sequence
<220> FEATURE:
<223> OTHER INFORMATION: synthetic

<400> SEQUENCE: 27
aaaagugugu gugugugugu guguc                                             25

<210> SEQ ID NO 28
<211> LENGTH: 24
<212> TYPE: RNA
<213> ORGANISM: Artificial Sequence
<220> FEATURE:
<223> OTHER INFORMATION: synthetic

<400> SEQUENCE: 28
aaagugugug ugugugugug uguc                                              24

<210> SEQ ID NO 29
<211> LENGTH: 23
<212> TYPE: RNA
<213> ORGANISM: Artificial Sequence
<220> FEATURE:
<223> OTHER INFORMATION: synthetic

<400> SEQUENCE: 29
```

```
aagugugugu gugugugugu guc                                          23

<210> SEQ ID NO 30
<211> LENGTH: 21
<212> TYPE: RNA
<213> ORGANISM: Artificial Sequence
<220> FEATURE:
<223> OTHER INFORMATION: synthetic

<400> SEQUENCE: 30
gugugugugu gugugugugu c                                            21

<210> SEQ ID NO 31
<211> LENGTH: 20
<212> TYPE: RNA
<213> ORGANISM: Artificial Sequence
<220> FEATURE:
<223> OTHER INFORMATION: synthetic

<400> SEQUENCE: 31
ugugugugug uguguguguc                                              20

<210> SEQ ID NO 32
<211> LENGTH: 19
<212> TYPE: RNA
<213> ORGANISM: Artificial Sequence
<220> FEATURE:
<223> OTHER INFORMATION: synthetic

<400> SEQUENCE: 32
gugugugugu gugugguc                                                19

<210> SEQ ID NO 33
<211> LENGTH: 17
<212> TYPE: RNA
<213> ORGANISM: Artificial Sequence
<220> FEATURE:
<223> OTHER INFORMATION: synthetic

<400> SEQUENCE: 33
gugugugugu gugguc                                                  17

<210> SEQ ID NO 34
<211> LENGTH: 15
<212> TYPE: RNA
<213> ORGANISM: Artificial Sequence
<220> FEATURE:
<223> OTHER INFORMATION: synthetic

<400> SEQUENCE: 34
gugugugugu guguc                                                   15

<210> SEQ ID NO 35
<211> LENGTH: 13
<212> TYPE: RNA
<213> ORGANISM: Artificial Sequence
<220> FEATURE:
<223> OTHER INFORMATION: synthetic

<400> SEQUENCE: 35
gugugugugu guc                                                     13

<210> SEQ ID NO 36
<211> LENGTH: 26
<212> TYPE: RNA
<213> ORGANISM: Artificial Sequence
```

```
<220> FEATURE:
<223> OTHER INFORMATION: synthetic

<400> SEQUENCE: 36
aaagugugug ugugugugug uguggu                                          26

<210> SEQ ID NO 37
<211> LENGTH: 24
<212> TYPE: RNA
<213> ORGANISM: Artificial Sequence
<220> FEATURE:
<223> OTHER INFORMATION: synthetic

<400> SEQUENCE: 37
aaagugugug ugugugugug ugug                                            24

<210> SEQ ID NO 38
<211> LENGTH: 26
<212> TYPE: RNA
<213> ORGANISM: Artificial Sequence
<220> FEATURE:
<223> OTHER INFORMATION: synthetic

<400> SEQUENCE: 38
aaagugugug ugugugugug uguagu                                          26

<210> SEQ ID NO 39
<211> LENGTH: 24
<212> TYPE: RNA
<213> ORGANISM: Artificial Sequence
<220> FEATURE:
<223> OTHER INFORMATION: synthetic

<400> SEQUENCE: 39
aaagugugug ugugugugug ugua                                            24

<210> SEQ ID NO 40
<211> LENGTH: 23
<212> TYPE: RNA
<213> ORGANISM: Artificial Sequence
<220> FEATURE:
<223> OTHER INFORMATION: synthetic

<400> SEQUENCE: 40
aaagugugug ugugugugug ugu                                             23

<210> SEQ ID NO 41
<211> LENGTH: 21
<212> TYPE: RNA
<213> ORGANISM: Artificial Sequence
<220> FEATURE:
<223> OTHER INFORMATION: synthetic

<400> SEQUENCE: 41
aaagugugug ugugugugug u                                               21

<210> SEQ ID NO 42
<211> LENGTH: 19
<212> TYPE: RNA
<213> ORGANISM: Artificial Sequence
<220> FEATURE:
<223> OTHER INFORMATION: synthetic

<400> SEQUENCE: 42
aaagugugug ugugugugu                                                  19
```

```
<210> SEQ ID NO 43
<211> LENGTH: 30
<212> TYPE: RNA
<213> ORGANISM: Artificial Sequence
<220> FEATURE:
<223> OTHER INFORMATION: synthetic

<400> SEQUENCE: 43
gacgacgacg acgacgacga cgacgacgac                                      30

<210> SEQ ID NO 44
<211> LENGTH: 24
<212> TYPE: RNA
<213> ORGANISM: Artificial Sequence
<220> FEATURE:
<223> OTHER INFORMATION: synthetic

<400> SEQUENCE: 44
gacacacaca cacacacaca caca                                            24

<210> SEQ ID NO 45
<211> LENGTH: 34
<212> TYPE: RNA
<213> ORGANISM: Artificial Sequence
<220> FEATURE:
<223> OTHER INFORMATION: synthetic Reference name AS A34

<400> SEQUENCE: 45
aaagugugug ugugugugug uguugugugu gugu                                 34

<210> SEQ ID NO 46
<211> LENGTH: 24
<212> TYPE: RNA
<213> ORGANISM: Artificial Sequence
<220> FEATURE:
<223> OTHER INFORMATION: derived from Aequorea victoria sequence
      identical to GFP protein except for last 3 nucleotides at 3'end
      Reference name ASGFP2

<400> SEQUENCE: 46
aagaugaacu ucagggucag cguc                                            24

<210> SEQ ID NO 47
<211> LENGTH: 23
<212> TYPE: RNA
<213> ORGANISM: Artificial Sequence
<220> FEATURE:
<223> OTHER INFORMATION: derived from Aequorea victoria sequence
      identical to GFP protein except for last 2 nucleotides at 3'end
      Reference name ASGFP2 3'23

<400> SEQUENCE: 47
aagaugaacu ucagggucag cgu                                             23

<210> SEQ ID NO 48
<211> LENGTH: 21
<212> TYPE: RNA
<213> ORGANISM: Artificial Sequence
<220> FEATURE:
<223> OTHER INFORMATION: derived from Aequorea victoria sequence
      Reference name ASGFP2 3'21

<400> SEQUENCE: 48
aagaugaacu ucagggucag c                                               21

<210> SEQ ID NO 49
```

```
<211> LENGTH: 19
<212> TYPE: RNA
<213> ORGANISM: Artificial Sequence
<220> FEATURE:
<223> OTHER INFORMATION: derived from Aequorea victoria sequence
      Reference name ASGFP2 3'19

<400> SEQUENCE: 49
aagaugaacu ucaggguca                                              19

<210> SEQ ID NO 50
<211> LENGTH: 21
<212> TYPE: RNA
<213> ORGANISM: Artificial Sequence
<220> FEATURE:
<223> OTHER INFORMATION: derived from Aequorea victoria sequence
      identical to GFP protein except for last 3 nucleotides at 3'end
      Reference name ASGFP2 5'21

<400> SEQUENCE: 50
augaacuuca gggucagcgu c                                           21

<210> SEQ ID NO 51
<211> LENGTH: 19
<212> TYPE: RNA
<213> ORGANISM: Artificial Sequence
<220> FEATURE:
<223> OTHER INFORMATION: derived from Aequorea victoria sequence
      identical to GFP protein except for last 3 nucleotides at 3'end
      Reference name ASGFP2 5'19

<400> SEQUENCE: 51
gaacuucagg gucagcguc                                              19

<210> SEQ ID NO 52
<211> LENGTH: 24
<212> TYPE: RNA
<213> ORGANISM: Artificial Sequence
<220> FEATURE:
<223> OTHER INFORMATION: derived from Aequorea victoria sequence
      identical to GFP protein except for last 3 nucleotides at 5'end
      Reference name 3P-GFP1

<400> SEQUENCE: 52
ggggcugacc cugaaguuca ucuu                                        24

<210> SEQ ID NO 53
<211> LENGTH: 24
<212> TYPE: RNA
<213> ORGANISM: Artificial Sequence
<220> FEATURE:
<223> OTHER INFORMATION: derived from Aequorea victoria sequence
      identical to GFP protein except for last 3 nucleotides at 5'end
      Reference name 3P-GFP2

<400> SEQUENCE: 53
gacgcugacc cugaaguuca ucuu                                        24

<210> SEQ ID NO 54
<211> LENGTH: 24
<212> TYPE: RNA
<213> ORGANISM: Artificial Sequence
<220> FEATURE:
<223> OTHER INFORMATION: synthetic Reference name 3P-GFP3

<400> SEQUENCE: 54
ggggcgcuga cgcccugaag uuca                                        24
```

```
<210> SEQ ID NO 55
<211> LENGTH: 25
<212> TYPE: RNA
<213> ORGANISM: Artificial Sequence
<220> FEATURE:
<223> OTHER INFORMATION: synthetic Reference name TAK P25

<400> SEQUENCE: 55
aaacugaaag ggagaaguga aagug                                       25

<210> SEQ ID NO 56
<211> LENGTH: 27
<212> TYPE: RNA
<213> ORGANISM: Artificial Sequence
<220> FEATURE:
<223> OTHER INFORMATION: synthetic Reference name TAK 25P

<400> SEQUENCE: 56
aaacugaaag ggagaaguga aagugag                                     27

<210> SEQ ID NO 57
<211> LENGTH: 25
<212> TYPE: RNA
<213> ORGANISM: Artificial Sequence
<220> FEATURE:
<223> OTHER INFORMATION: synthetic Reference name TAK 25

<400> SEQUENCE: 57
aaacugaaag ggagaaguga aagug                                       25

<210> SEQ ID NO 58
<211> LENGTH: 25
<212> TYPE: RNA
<213> ORGANISM: Artificial Sequence
<220> FEATURE:
<223> OTHER INFORMATION: synthetic Reference name TAK 25c

<400> SEQUENCE: 58
cacuuucacu ucucccuuuc aguuu                                       25

<210> SEQ ID NO 59
<211> LENGTH: 19
<212> TYPE: RNA
<213> ORGANISM: Artificial Sequence
<220> FEATURE:
<223> OTHER INFORMATION: derived from mouse sequence Reference name
      Murine Bcl-22.1 sense

<400> SEQUENCE: 59
augccuuugu ggaacuaua                                              19

<210> SEQ ID NO 60
<211> LENGTH: 19
<212> TYPE: RNA
<213> ORGANISM: Artificial Sequence
<220> FEATURE:
<223> OTHER INFORMATION: derived from mouse sequence Reference name
      Murine Bcl-22.1 anti-sense

<400> SEQUENCE: 60
uauaguucca caaaggcau                                              19

<210> SEQ ID NO 61
<211> LENGTH: 19
<212> TYPE: RNA
<213> ORGANISM: Artificial Sequence
```

```
<220> FEATURE:
<223> OTHER INFORMATION: derived from mouse sequence Reference name
      Murine Bcl-22.1 sense

<400> SEQUENCE: 61
gcaugcgacc ucuguuuga                                                    19

<210> SEQ ID NO 62
<211> LENGTH: 19
<212> TYPE: RNA
<213> ORGANISM: Artificial Sequence
<220> FEATURE:
<223> OTHER INFORMATION: derived from mouse sequence Reference name
      Murine Bcl-22.1 anti-sense

<400> SEQUENCE: 62
ucaaacagag gucgcaugc                                                    19

<210> SEQ ID NO 63
<211> LENGTH: 19
<212> TYPE: RNA
<213> ORGANISM: Artificial Sequence
<220> FEATURE:
<223> OTHER INFORMATION: derived from mouse sequence Reference name
      Murine Bcl-22.1 sense

<400> SEQUENCE: 63
ggaugacuga guaccugaa                                                    19

<210> SEQ ID NO 64
<211> LENGTH: 19
<212> TYPE: RNA
<213> ORGANISM: Artificial Sequence
<220> FEATURE:
<223> OTHER INFORMATION: derived from mouse sequence Reference name
      Murine Bcl-22.1 anti-sense

<400> SEQUENCE: 64
uucagguacu cagucaucc                                                    19

<210> SEQ ID NO 65
<211> LENGTH: 19
<212> TYPE: RNA
<213> ORGANISM: Artificial Sequence
<220> FEATURE:
<223> OTHER INFORMATION: synthetic Reference name PolyA

<400> SEQUENCE: 65
aaaaaaaaaa aaaaaaaaa                                                    19

<210> SEQ ID NO 66
<211> LENGTH: 19
<212> TYPE: RNA
<213> ORGANISM: Artificial Sequence
<220> FEATURE:
<223> OTHER INFORMATION: derived from mouse sequence Murine RIG-I sense

<400> SEQUENCE: 66
gaagcgucuu cuaauaauu                                                    19

<210> SEQ ID NO 67
<211> LENGTH: 19
<212> TYPE: RNA
<213> ORGANISM: Artificial Sequence
<220> FEATURE:
<223> OTHER INFORMATION: derived from mouse sequence Reference name
      Murine RIG-I anti-sense
```

```
<400> SEQUENCE: 67
aauuauuaga agacgcuuc                                                 19

<210> SEQ ID NO 68
<211> LENGTH: 19
<212> TYPE: RNA
<213> ORGANISM: Artificial Sequence
<220> FEATURE:
<223> OTHER INFORMATION: synthetic Reference name Control siRNA sense

<400> SEQUENCE: 68
uucuccgaac gugucacgu                                                 19

<210> SEQ ID NO 69
<211> LENGTH: 19
<212> TYPE: RNA
<213> ORGANISM: Artificial Sequence
<220> FEATURE:
<223> OTHER INFORMATION: synthetic Reference name Control siRNA anti-
      sense

<400> SEQUENCE: 69
acgugacacg uucggagaa                                                 19

<210> SEQ ID NO 70
<211> LENGTH: 19
<212> TYPE: RNA
<213> ORGANISM: Artificial Sequence
<220> FEATURE:
<223> OTHER INFORMATION: derived from mouse sequence Reference name
      Murine Bcl-22.4 sense

<400> SEQUENCE: 70
ggagaacagg guaugauaa                                                 19

<210> SEQ ID NO 71
<211> LENGTH: 19
<212> TYPE: RNA
<213> ORGANISM: Artificial Sequence
<220> FEATURE:
<223> OTHER INFORMATION: derived from mouse sequence Reference name
      Murine Bcl-22.4 anti-sense

<400> SEQUENCE: 71
ccucuugucc cauacuauu                                                 19

<210> SEQ ID NO 72
<211> LENGTH: 19
<212> TYPE: RNA
<213> ORGANISM: Artificial Sequence
<220> FEATURE:
<223> OTHER INFORMATION: derived from human sequence Reference name
      Human Bcl-2 h2.2 sense

<400> SEQUENCE: 72
gcaugcggcc ucuguuuga                                                 19

<210> SEQ ID NO 73
<211> LENGTH: 19
<212> TYPE: RNA
<213> ORGANISM: Artificial Sequence
<220> FEATURE:
<223> OTHER INFORMATION: derived from human sequence Reference name
      Human Bcl-2 h2.2 anti-sense

<400> SEQUENCE: 73
```
cguacgccgg agacaaacu                                                19

<210> SEQ ID NO 74
<211> LENGTH: 19
<212> TYPE: DNA
<213> ORGANISM: Artificial Sequence
<220> FEATURE:
<223> OTHER INFORMATION: derived from mouse sequence Reference name
      IFNAR sense

<400> SEQUENCE: 74
tggaagccgt tcagataaa                                                19

<210> SEQ ID NO 75
<211> LENGTH: 19
<212> TYPE: DNA
<213> ORGANISM: Artificial Sequence
<220> FEATURE:
<223> OTHER INFORMATION: derived from mouse sequence Reference name
      IFNAR anti-sense

<400> SEQUENCE: 75
tttatctgaa cggcttcca                                                19

<210> SEQ ID NO 76
<211> LENGTH: 32
<212> TYPE: DNA
<213> ORGANISM: Artificial Sequence
<220> FEATURE:
<223> OTHER INFORMATION: derived from mouse sequence Reference name
      Murine Bcl-22.2 sense

<400> SEQUENCE: 76
tcaaacagag gtcgcatgcc tatagtgagt cg                                 32

<210> SEQ ID NO 77
<211> LENGTH: 32
<212> TYPE: DNA
<213> ORGANISM: Artificial Sequence
<220> FEATURE:
<223> OTHER INFORMATION: derived from mouse sequence Reference name
      Murine Bcl-22.2 anti-sense

<400> SEQUENCE: 77
gcatgcgacc tctgtttgac tatagtgagt cg                                 32

<210> SEQ ID NO 78
<211> LENGTH: 32
<212> TYPE: DNA
<213> ORGANISM: Artificial Sequence
<220> FEATURE:
<223> OTHER INFORMATION: synthetic Reference name GC sense

<400> SEQUENCE: 78
ggcgccccgc cgcgccccgc tatagtgagt cg                                 32

<210> SEQ ID NO 79
<211> LENGTH: 32
<212> TYPE: DNA
<213> ORGANISM: Artificial Sequence
<220> FEATURE:
<223> OTHER INFORMATION: synthetic Reference name GC anti-sense

<400> SEQUENCE: 79
gcggggcgcg gcggggcgcc tatagtgagt cg                                 32

<210> SEQ ID NO 80
<211> LENGTH: 32
<212> TYPE: DNA
<213> ORGANISM: Artificial Sequence
<220> FEATURE:
<223> OTHER INFORMATION: derived from mouse sequence Reference name
      Murine Bcl-22.4 sense

<400> SEQUENCE: 80
ttatcatacc ctgttctccc tatagtgagt cg                                32

<210> SEQ ID NO 81
<211> LENGTH: 32
<212> TYPE: DNA
<213> ORGANISM: Artificial Sequence
<220> FEATURE:
<223> OTHER INFORMATION: derived from mouse sequence Reference name
      Murine Bcl-22.4 anti-sense

<400> SEQUENCE: 81
ggagaacagg gtatgataac tatagtgagt cg                                32

<210> SEQ ID NO 82
<211> LENGTH: 32
<212> TYPE: DNA
<213> ORGANISM: Artificial Sequence
<220> FEATURE:
<223> OTHER INFORMATION: derived from human sequence Reference name
      Human Bcl-2 h2.2 sense

<400> SEQUENCE: 82
tcaaacagag gccgcatgcc tatagtgagt cg                                32

<210> SEQ ID NO 83
<211> LENGTH: 32
<212> TYPE: DNA
<213> ORGANISM: Artificial Sequence
<220> FEATURE:
<223> OTHER INFORMATION: derived from human sequence Reference name
      Human Bcl-2 h2.2 anti-sense

<400> SEQUENCE: 83
gcatgcggcc tctgtttgac tatagtgagt cg                                32

<210> SEQ ID NO 84
<211> LENGTH: 32
<212> TYPE: DNA
<213> ORGANISM: Artificial Sequence
<220> FEATURE:
<223> OTHER INFORMATION: synthetic Reference name Murina Bcl-2 mismatch
      sense

<400> SEQUENCE: 84
tcaaacagtc ctcgcatgcc tatagtgagt cg                                32

<210> SEQ ID NO 85
<211> LENGTH: 32
<212> TYPE: DNA
<213> ORGANISM: Artificial Sequence
<220> FEATURE:
<223> OTHER INFORMATION: synthetic Reference name Human Bcl-2 mismatch
      anti-sense

<400> SEQUENCE: 85
gcatgcgagg actgtttgac tatagtgagt cg                                32

```
<210> SEQ ID NO 86
<211> LENGTH: 25
<212> TYPE: DNA
<213> ORGANISM: Artificial Sequence
<220> FEATURE:
<223> OTHER INFORMATION: derived from mouse sequence Reference name cDNA

<400> SEQUENCE: 86
gttcatctga agtttccagc ctttg                                             25

<210> SEQ ID NO 87
<211> LENGTH: 23
<212> TYPE: DNA
<213> ORGANISM: Artificial Sequence
<220> FEATURE:
<223> OTHER INFORMATION: synthetic Reference name primer GR 5'

<400> SEQUENCE: 87
cgactggagc acgaggacac tga                                               23

<210> SEQ ID NO 88
<211> LENGTH: 26
<212> TYPE: DNA
<213> ORGANISM: Artificial Sequence
<220> FEATURE:
<223> OTHER INFORMATION: synthetic Reference name primer GRN 5'

<400> SEQUENCE: 88
ggacactgac atggactgaa ggagta                                            26

<210> SEQ ID NO 89
<211> LENGTH: 32
<212> TYPE: DNA
<213> ORGANISM: Artificial Sequence
<220> FEATURE:
<223> OTHER INFORMATION: synthetic Reference name primer Rev.1

<400> SEQUENCE: 89
tccctttggc agtaaatagc tgattcgacc at                                     32

<210> SEQ ID NO 90
<211> LENGTH: 30
<212> TYPE: DNA
<213> ORGANISM: Artificial Sequence
<220> FEATURE:
<223> OTHER INFORMATION: synthetic Reference name primer Rev.2

<400> SEQUENCE: 90
aagtcccttc tccagtccat ggaagaccag                                        30

<210> SEQ ID NO 91
<211> LENGTH: 33
<212> TYPE: DNA
<213> ORGANISM: Artificial Sequence
<220> FEATURE:
<223> OTHER INFORMATION: synthetic Reference name primer RevN

<400> SEQUENCE: 91
ctttggcagt aaatagctga ttcgaccatt tgc                                    33
```

5' TRIPHOSPHATE OLIGONUCLEOTIDE WITH BLUNT END AND USES THEREOF

CROSS-REFERENCE TO RELATED APPLICATIONS

This application is a continuation of U.S. application Ser. No. 12/993,420, which is a 35 U.S.C. §371 National Phase Entry application of International Application No. PCT/EP2009/003621 filed on May 20, 2009, which designates the United States, and which claims the benefit of priority of European Application No. 08009406.3 filed May 21, 2008, European Application No. 08015261.4 filed Aug. 29, 2008, and European Application No. 08018243.9 filed Oct. 17, 2008; and which also claims the benefit of priority under 35 U.S.C. §119(e) of U.S. Provisional Application No. 61/076,986 filed Jun. 30, 2008; U.S. Provisional Application No. 61/082,431 filed Jul. 21, 2008; U.S. Provisional Application No. 61/092,825 filed Aug. 29, 2008; and U.S. Provisional Application No. 61/100,594 filed Sep. 26, 2008, the contents of each of which are incorporated by reference herein in their entirety.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: 20,480 bytes ASCII (Text) file named "723250_ST25.TXT" created Apr. 13, 2016.

FIELD OF THE INVENTION

The present invention relates to the field of immunotherapy and drug discovery. The present invention provides an oligonucleotide which is capable of activating RIG-I and/or inducing an anti-viral, in particular, an IFN, response in cells expressing RIG-I. The present invention further provides the use of said oligonucleotide for inducing an anti-viral, in particular, an IFN, response in vitro and in vivo. The present invention further relates to an oligonucleotide which has both gene-silencing activity and is capable of activating RIG-I. The present invention additionally provides the use of said oligonucleotide for preventing and/or treating diseases or conditions such as infections, tumors/cancers, and immune disorders.

BACKGROUND OF THE INVENTION

The presence of viral nucleic acids represents a danger signal for the immune system which initiates an anti-viral response to impede viral replication and eliminate the invading pathogen[1]. Interferon (IFN) response is a major component of the anti-viral response and comprises the production of type I IFNs, IFN-α and IFN-β. An anti-viral response also comprises the production of various other cytokines, such as IL-12, which promote innate and adaptive immunity[1].

In order to detect foreign nucleic acids, immune cells are equipped with a set of pattern recognition receptors (PRR) which act at the frontline of the recognition process and which can be grouped into two major classes: the Toll-like receptors and the RNA helicases.

Members of the Toll-like receptor (TLR) family have been implicated in the detection of long dsRNA (TLR3)[2], ssRNA (TLR7 and 8)[3,4], short dsRNA (TLR7)[5] and CpG DNA (TLR9)[6]. The TLRs reside primarily in the endosomal membranes of the immune cells[7,8] and recognize viral nucleic acids that have been taken up by the immune cells into the endosomal compartments[9].

RNA helicases, such as RIG-I, MDA-5 and LGP-2, have been implicated in the detection of viral RNA[10,11]. In contrast to the TLRs, the RNA helicases are cytosolic and are expressed in a wide spectrum of cell types, including immune cells and non-immune cells, such as fibroblasts and epithelial cells[12]. Therefore, not only immune cells, but also non-immune cells which express one or more of the RNA helicase(s), are capable of detecting and responding to viral RNA.

Both the TLR and the RNA helicase systems co-operate to optimally detect viral RNA.

Given the abundance of host RNA present in the cytoplasm, it is an intricate task to specifically and reliably detect virus-derived RNA. Maximal sensitivity together with a high degree of specificity for "non-self" are required. Two major mechanisms appear to be in place in vertebrate cells to distinguish "non-self" from "self" nucleic acids via a protein receptor-based recognition system: (1) the detection of a pathogen-specific compartmentalization, and (2) the detection of a pathogen-specific molecular signature or motif.

Endosomal RNA is recognized by the TLRs as "non-self"[4]. Notably, host RNA can acquire the ability to stimulate an IFN response via the activation of TLRs under certain pathological situations[13].

Furthermore, there exist structural motifs or molecular signatures that allow the pattern recognition receptors (PRRs) to determine the origin of an RNA. For example, long dsRNA has been proposed to stimulate an IFN response via TLR3[2], RIG-I[11] and MDA-5[14]. The present inventors recently identified the 5' triphosphate moiety of viral RNA transcripts as the ligand for RIG-I[16,19]. Even though nascent nuclear endogenous host RNA transcripts initially also contain a 5' triphosphate, several nuclear post-transcriptional modifications, including 5' capping, endonucleolytic cleavage, and base and backbone modifications, of the nascent RNA transcripts lead to mature cytoplasmic RNAs which are ignored by RIG-I. In addition, blunt-ended short dsRNA without any 5' phosphate group[16] or with 5' monophosphate[24] has also been postulated to stimulate RIG-I. A clearly defined molecular signature has not yet been reported for the ssRNA-sensing TLRs, TLR7 and TLR8. However, the fact that certain sequence motifs are better recognized than others by the TLRs suggests that the nucleotide composition of the RNA, on top of endosomal localization, may represent basis for discriminating between "self" and "non-self" by the TLRs[3-5, 10, 11, 17, 18].

Despite its pivotal role in anti-viral defense, the mechanism of viral RNA recognition by RIG-I is not yet fully elucidated. Therefore, there is a need in the art to better understand the recognition of viral and/or other non-self RNA by RIG-I. Furthermore, given the efficacy of IFN-α in various clinical applications, there is a need in the art to provide alternative agents for inducing IFN-α production in vitro and in vivo.

It is therefore an object of the present invention to further identify the structural motifs or molecular signatures of an RNA molecule which are recognized by RIG-I. It is another object of the present invention to prepare RNA molecules which are capable of activating RIG-I and inducing an anti-viral, in particular, an IFN, response in cells expressing RIG-I. It is a further object of the present invention to use said RNA molecules for inducing an anti-viral, in particular, an IFN, response in vitro and in vivo. It is an ultimate object of the present invention to use said RNA molecules for preventing and/or treating diseases or conditions which would benefit from an anti-viral, in particular, an IFN, response, such as infections, tumors/cancers, and immune disorders.

Cellular transformation and progressive tumor growth result from an accumulation of genetic and epigenetic changes that alter normal cell proliferation and survival pathways[38]. Tumor pathogenesis is accompanied by a process called cancer immunoediting, a temporal transition from immune-mediated tumor elimination in early phases of tumor development to immune escape of established tumors. The interferons (IFNs) have emerged as central coordinators of these tumor-immune-system interactions[38]. Due to their plasticity tumors tend to evade single-targeted therapeutic approaches designed to control proliferation and survival of tumor cells[40]. Tumors even evade immunotherapies that are directed at multiple tumor antigens[41].

It is therefore a further object of the present invention to use said RNA molecules for inducing apoptose, or both for inducing an anti-viral, in particular, an IFN, response in vitro and in vivo and for inducing apoptosis in the same molecule.

There remains a need in the art for combinatorial approaches that suppress tumor cell survival and at the same time increase immunogenicity of tumor cells in order to provide more effective tumor treatments[42, 43].

SUMMARY OF THE INVENTION

The present invention provides an oligonucleotide preparation comprising an essentially homogenous population of an oligonucleotide,
  wherein the oligonucleotide has at least one blunt end,
  wherein the oligonucleotide comprises at least 1, preferably at least 3, more preferably at least 6 ribonucleotide(s) at the 5' end at the blunt end,
  wherein the blunt end bears a 5' triphosphate attached to the most 5' ribonucleotide, wherein the 5' triphosphate is free of any cap structure,
  wherein the blunt end is an end of a fully double-stranded section, and wherein the fully double-stranded section is at least 19, preferably at least 21, more preferably at least 24 base pairs in length.

In one embodiment, the oligonucleotide is double-stranded.

In another embodiment, the double-stranded section is the stem of a single-stranded oligonucleotide having a stem-and-loop structure.

In one embodiment, the oligonucleotide comprises at least one inosine.

In another embodiment, the most 5' ribonucleotide with the triphosphate attached to is selected from A, G and U, preferably A and G, and most preferably A.

In a specific embodiment, the sequence of the first 4 ribonucleotides at the 5' end is selected from: AAGU, AAAG, AUGG, AUUA, AACG, AUGA, AGUU, AUUG, AACA, AGAA, AGCA, AACU, AUCG, AGGA, AUCA, AUGC, AGUA, AAGC, AACC, AGGU, AAAC, AUGU, ACUG, ACGA, ACAG, AAGG, ACAU, ACGC, AAAU, ACGG, AUUC, AGUG, ACAA, AUCC, AGUC, wherein the sequence is in the 5'→3' direction.

In yet another embodiment, the oligonucleotide is free of modifications selected pseudouridine, 2-thiouridine, 2'-Fluorine-dNTP, in particular 2'-fluorine-dCTP, 2'-fluorine-dUTP.

In a preferred embodiment, the most 3' nucleotide which base pairs with the most 5' ribonucleotide bearing the 5' triphosphate at the blunt end is 2'-O-methylated. More preferably, said nucleotide is 2'-O-methylated UTP.

In a further embodiment, the oligonucleotide comprises at least one structural motif recognized by at least one of TLR3, TLR7, TLR8 and TLR9.

In an additional embodiment, the oligonucleotide has gene-silencing activity.

In a preferred embodiment, the oligonucleotide having gene-silencing activity is a siRNA.

In a further embodiment, the oligonucleotide of the invention has both gene-silencing activity and the ability of RIG-I activation, e.g. a double-stranded oligonucleotide with a 5'-triphosphate end (3p-siRNA).

In a further embodiment, the oligonucleotide of the invention has gene-silencing activity and the ability of RIG-I activation, e.g. a double-stranded oligonucleotide with a 5'-triphosphate end (3p-siRNA), and contains sequences or structural motifs that are recognized by TLR7 and activate TLR7.

The present invention provides a pharmaceutical composition comprising at least one oligonucleotide preparation of the present invention and a pharmaceutically acceptable carrier.

In one embodiment, the pharmaceutical composition further comprises at least one agent selected from an immunostimulatory agent, an antigen, an anti-viral agent, an anti-bacterial agent, an anti-tumor agent, retinoic acid, IFN-α, and IFN-β.

The present invention further provides the use of at least one oligonucleotide preparation of the present invention for the preparation of a composition for inducing type I IFN production.

The present invention also provides the use of at least one oligonucleotide preparation of the present invention for the preparation of a composition for preventing and/or treating a disease or condition selected from an infection, a tumor, and an immune disorder.

In one embodiment, the oligonucleotide preparation is used in combination with at least one agent selected from an immunostimulatory agent, an antigen, an anti-viral agent, an anti-bacterial agent, an anti-tumor agent, retinoic acid, IFN-α, and IFN-β.

In another embodiment, the composition is prepared for administration in combination with at least one treatment selected from a prophylactic and/or a therapeutic treatment of an infection, a tumor, and an immune disorder.

The present invention additionally provides an in vitro method for inducing type I IFN production in a cell, comprising the steps of:
  (a) mixing at least oligonucleotide preparation of the present invention with a complexation agent; and
  (b) contacting a cell with the mixture of (a), wherein the cell expresses RIG-I.

The present invention provides an oligonucleotide preparation comprising an essentially homogenous population of a single-strand oligonucleotide, wherein the oligonucleotide has a nucleotide sequence which is 100% complementary to at least 19, preferably at least 21 nucleotides at the very 5' end of the genomic RNA of a negative single-strand RNA virus. The present invention further provides the use of said oligonucleotide preparation for the preparation of a composition for preventing and/or treating an infection by the negative single-strand RNA virus in a mammal.

The present invention also provides an oligonucleotide preparation comprising an essentially homogenous population of a single-strand oligonucleotide, wherein the oligonucleotide has a nucleotide sequence which is 100% complementary to the nucleotide sequence at the 5' end of the genomic RNA of a negative single-strand RNA virus between nucleotides 2+m and 2+m+n, wherein m and n are independently positive integers, wherein m equals to or is greater than 1 and is less than or equals to 5, and wherein n equals to or is greater than 12. The present invention further provides the use of said oligonucleotide preparation for the preparation of a composition for preventing and/or inhibiting a type I IFN response against the single-strand RNA virus in a mammal. The present invention additionally provides the use of said oligonucleotide preparation for the preparation of a composition for treating virus-induced hemorrhagic fever.

In certain embodiments, the negative single-strand RNA virus is selected from influenza A virus, Rabies virus, Newcastle disease virus (NDV), vesicular stomatitis virus (VSV), Measles virus, mumps virus, respiratory syncytial virus (RSV), Sendai virus, Ebola virus, or Hantavirus.

In a further embodiment, the present invention is directed to an oligonucleotide preparation as defined above having the ability to induce apoptosis.

In a further embodiment, the present invention is directed to an oligonucleotide preparation as defined above having the ability to preferentially induce apoptosis in tumor cells compared to primary cells, for example if the tumor is a melanoma the primary cells may be melanocytes or fibroblasts.

In a further embodiment, the present invention is directed to an oligonucleotide preparation as defined above having two distinct functional properties: a) gene silencing and b) RIG-I activation. Particularly preferred are anti-bcl-2 double-stranded oligonucleotides with 5'-triphosphate ends (3p-siRNA). The present invention further provides a pharmaceutical composition comprising said oligonucleotide preparations having two distinct functional properties and optionally a pharmaceutically acceptable carrier. The present invention further provides a pharmaceutical composition comprising said oligonucleotide preparations having apoptose-inducing activity. The present invention additionally provides the use of said oligonucleotide preparations having two distinct functional properties for the preparation of a pharmaceutical composition for treating cancer, in particular melanomas.

The present invention further provides a pharmaceutical composition comprising at least one of the above-described oligonucleotide preparation and a pharmaceutically acceptable carrier.

The present invention provides a method for preparing a double-strand oligonucleotide preparation having type I IFN-inducing activity, comprising the steps of:

(a) identifying two oligonucleotide sequences, wherein at least one of the nucleotide sequences comprises at least 1 ribonucleotide at the 5' end, wherein the sequence of the at least 19, preferably at least 21 nucleotides at the 5' end of the at least one oligonucleotide sequence which comprises at least 1 ribonucleotide at the 5' end has 100% complementarity with the sequence of the at least 19, preferably at least 21 nucleotides at the 3' end of the other oligonucleotide sequence, thereby forming a blunt end;

(b) preparing two essentially homogenous populations of two oligonucleotides having the sequences identified in (a), wherein the at least one oligonucleotide which comprises at least 1 ribonucleotide at the 5' end which forms the blunt end bears a 5' triphosphate on the most 5' ribonucleotide;

(c) preparing an essentially homogenous population of a double-strand oligonucleotide from the two oligonucleotides prepared in (b); and (d) optionally testing the type I IFN-inducing activity of the double-strand oligonucleotide.

The present invention provides a method for preparing a single-strand oligonucleotide preparation having type I IFN-inducing activity, comprising the steps of:

(a) identifying an oligonucleotide sequence, wherein the nucleotide sequence comprises at least 1 ribonucleotide at the 5' end, wherein the sequence of the at least 19, preferably at least 21 nucleotides at the 5' end of the oligonucleotide sequence has 100% complementarily with the sequence of the at least 19, preferably at least 21 nucleotides at the 3' end of the oligonucleotide sequence;

(b) preparing an essentially homogenous population of an oligonucleotide having the sequence identified in (a), wherein the oligonucleotide bears a 5' triphosphate on the most 5' ribonucleotide; and (c) optionally testing the type I IFN-inducing activity of the single-strand oligonucleotide.

The present invention provides a method for preparing an oligonucleotide preparation having the combined activity of target gene silencing and type I IFN inducing activity, comprising the steps of:

(a) identifying an oligonucleotide sequence, wherein the nucleotide sequence is specific for the target gene and comprises at least 1 ribonucleotide at the 5' end, wherein the sequence of the at least 19, preferably at least 21 nucleotides at the 5' end of the oligonucleotide sequence has 100% complementarity with the sequence of the at least 19, preferably at least 21 nucleotides at the 3' end of the oligonucleotide sequence;

(b) preparing an essentially homogenous population of an oligonucleotide having the sequence identified in (a), wherein the oligonucleotide bears a 5' triphosphate on the most 5' ribonucleotide;

(c) optionally testing the type I IFN-inducing activity of the single-strand oligonucleotide; and (d) optionally testing the oligonucleotide for gene-silencing activity.

The present invention further provides a method for preparing an oligonucleotide preparation having the combined activity of target gene-silencing and type I IFN-inducing activity, comprising the steps of:

(a) identifying a nucleotide sequence for a first oligonucleotide, wherein the nucleotide sequence is specific for the target gene;

(b) preparing an essentially homogenous population of the first oligonucleotide having the sequence identified in (a), (c) preparing a essentially homogenous population of a second oligonucleotide wherein the nucleotide sequence of the second oligonucleotide is 100% complementary to the nucleotide sequence of the first oligonucleotide;

(d) optionally testing the type I IFN-inducing activity of the single-strand oligonucleotide; and (e) optionally testing the oligonucleotide for gene-silencing activity;

wherein the first and/or the second oligonucleotide bears a 5' triphosphate on the most 5' ribonucleotide or on both 5' ribonucleotides; wherein the 5' triphosphate is free of any cap structure; and wherein the first and the second oligonucleotide has at least 19, preferably at least 21, more preferably at least 24 base pairs in length.

The present invention provides a method for enhancing the type I IFN-inducing activity of an oligonucleotide, wherein the oligonucleotide has at least one blunt end and comprises at least 1 ribonucleotide at the 5' end at the blunt end, wherein the blunt end bears a 5' triphosphate attached to the most 5' ribonucleotide, wherein the 5' triphosphate is free of any cap structure, and wherein the blunt end is followed by a fully double-stranded section which is at least 19, preferably at least 21 base pair (bp) in length, comprising the step of 2'-O-methylating the most 3' nucleotide which base pairs with the most 5' ribonucleotide bearing the 5' triphosphate at the blunt end.

The present invention also provides a method for reducing the type I IFN-inducing activity of an oligonucleotide, wherein the oligonucleotide has at least one blunt end and comprises at least 1 ribonucleotide at the 5' end at the blunt end, wherein the blunt end bears a 5' triphosphate attached to the most 5' ribonucleotide, wherein the 5' triphosphate is free of any cap structure, and wherein the blunt end is followed by a fully double-stranded section which is at least 19, preferably at least 21 base pair (bp) in length, comprising the step of 2'-O-methylating a nucleotide which is not the most 3' nucleotide which base pairs with the most 5' ribonucleotide bearing the 5' triphosphate at the blunt end; preferably, the nucleotide to be 2'-O-methylated is the nucleotide immediately 5' to the most 3' nucleotide which base pairs with the most 5' ribonucleotide bearing the 5' triphosphate at the blunt end.

The present invention further provides a method of determining whether a double stranded RNA (dsRNA) silences gene expression in a cell in vivo by an RNA interference (RNAi) mechanism, wherein the dsRNA comprises at least two sequences that are complementary to each other, and wherein a sense strand comprises a first sequence, and an antisense strand comprises a second sequence, which comprises a region of complementarity to an mRNA expressed in a mammal, wherein the region of complementarity is 19 to 20 nucleotides in length, and wherein the dsRNA further comprises a 5'triphosphate, the method comprising:
(i) providing an RNA sample isolated from the mammal, wherein the mammal was previously administered the dsRNA; and
(ii) performing 5'-rapid amplification of cDNA ends (5'RACE) to detect the cleavage site of the mRNA in the RNA sample;
wherein if the mRNA detectable by 5'RACE is cleaved at the predicted site, then the dsRNA is determined to silence gene expression by an RNAi mechanism.

In one embodiment of the method of determining whether a double stranded RNA (dsRNA) silences gene expression in a cell in vivo, the mRNA expressed in the mammal is a Bcl-2 mRNA.

In a further embodiment of the above method of determining whether a double stranded RNA (dsRNA) silences gene expression in a cell in vivo, the mammal is a mouse.

In a further embodiment of the above method of determining whether a double stranded RNA (dsRNA) silences gene expression in a cell in vivo, the dsRNA was administered intravenously.

In a further embodiment of the above method of determining whether a double stranded RNA (dsRNA) silences gene expression in a cell in vivo, the dsRNA comprises a 5'triphosphate on the sense strand and the antisense strand of the dsRNA.

In a further embodiment of the above method of determining whether a double stranded RNA (dsRNA) silences gene expression in a cell in vivo, the predicted cleavage site is at the nucleotide corresponding to the nucleotide ten nucleotides away from the 5' end of the antisense strand of the dsRNA.

The present invention further provides a method of determining whether a double stranded RNA (dsRNA) silences gene expression in cells in vitro by an RNA interference (RNAi) mechanism, wherein the dsRNA comprises at least two sequences that are complementary to each other, and wherein a sense strand comprises a first sequence, and an antisense strand comprises a second sequence, which comprises a region of complementarity to an mRNA expressed in the cells, wherein the region of complementarity is 19 to 20 nucleotides in length, and wherein the dsRNA further comprises a 5'triphosphate, the method comprising:
(i) providing an RNA sample isolated from the cells, wherein the cells were previously contacted with the dsRNA; and
(ii) performing 5'-rapid amplification of cDNA ends (5'RACE) to detect the cleavage site of the mRNA in the RNA sample;
wherein if the mRNA detectable by 5'RACE is cleaved at the predicted site, then the dsRNA is determined to silence gene expression by an RNAi mechanism.

In one embodiment of the method of determining whether a double stranded RNA (dsRNA) silences gene expression in cells in vitro, the mRNA expressed in the mammal is a Bcl-2 mRNA.

In a further embodiment of the above method of determining whether a double stranded RNA (dsRNA) silences gene expression in cells in vitro, the cells are B 16 melanoma cells.

In a further embodiment of the above method of determining whether a double stranded RNA (dsRNA) silences gene expression in cells in vitro, the dsRNA comprises a 5'triphosphate on the sense strand and the antisense strand of the dsRNA.

In a further embodiment of the above method of determining whether a double stranded RNA (dsRNA) silences gene expression in cells in vitro, the predicted cleavage site is at the nucleotide corresponding to the nucleotide ten nucleotides away from the 5' end of the antisense strand of the dsRNA.

B16 cells were seeded in 24-well plates at a confluency of 50%, B16 cells were transfected with the selected siRNAs at 1 μg/ml. 48 hours after transfection, protein expression of mouse Bcl-2, Mcl-1, Puma, Bcl-xL, Bim and β-actin was analysed by Western blot. One representative out of three independent experiments is shown.

Figure 24:
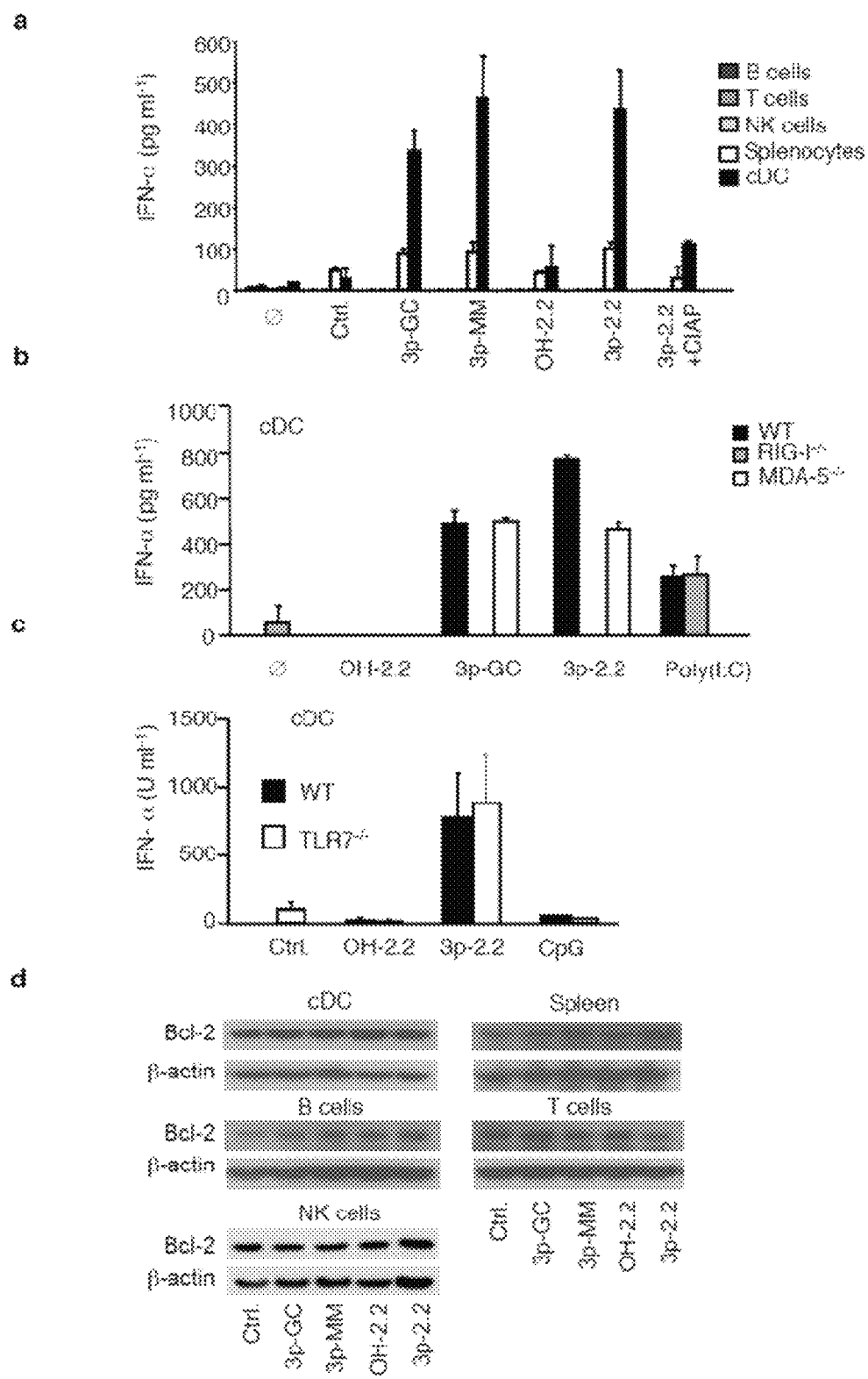

FIG. 24. Gene-silencing of Bcl-2 and IFN-α production by 5'-triphosphate siRNA is cell-type specific and requires RIG-I, but not MDA-5 or TLR7.

(a) GMCSF-derived cDCs as well as splenocytes, B cells, NK cells and T cells were transfected with the indicated siRNAs (1 μg/ml). After 24 h IFN-α production was quantified in the supernatant by ELISA. Data are shown as means±SEM of two independent experiments. (b) GMCSF-derived cDC of wild-type (WT), RIG-I- and MDA 5-deficient mice were transfected with 1 μg/ml of OH-2.2, 3p-GC, 3p-2.2, and Poly(I:C). After 24 h IFN-α production was quantified in the supernatant by ELISA. Data are shown as means±SEM of two independent experiments. (c) GMCSF-derived cDC of WT and TLR7-deficient mice were transfected with 1 μg/ml of OH-2.2, 3p-2.2 and CpG 2216 (3 μg/ml). After 24 h IFN-α production was quantified in the supernatant by ELISA. Data are expressed as mean±SEM of two independent experiments. (d) GMCSF-derived cDCs as well as splenocytes, B cells, NK cells and T cells were transfected with the indicated siRNAs (1 μg/ml). After 48 h Bcl-2 expression was analysed by Western blot. One representative Western blot out of two independent experiments is shown.

Figure 25:
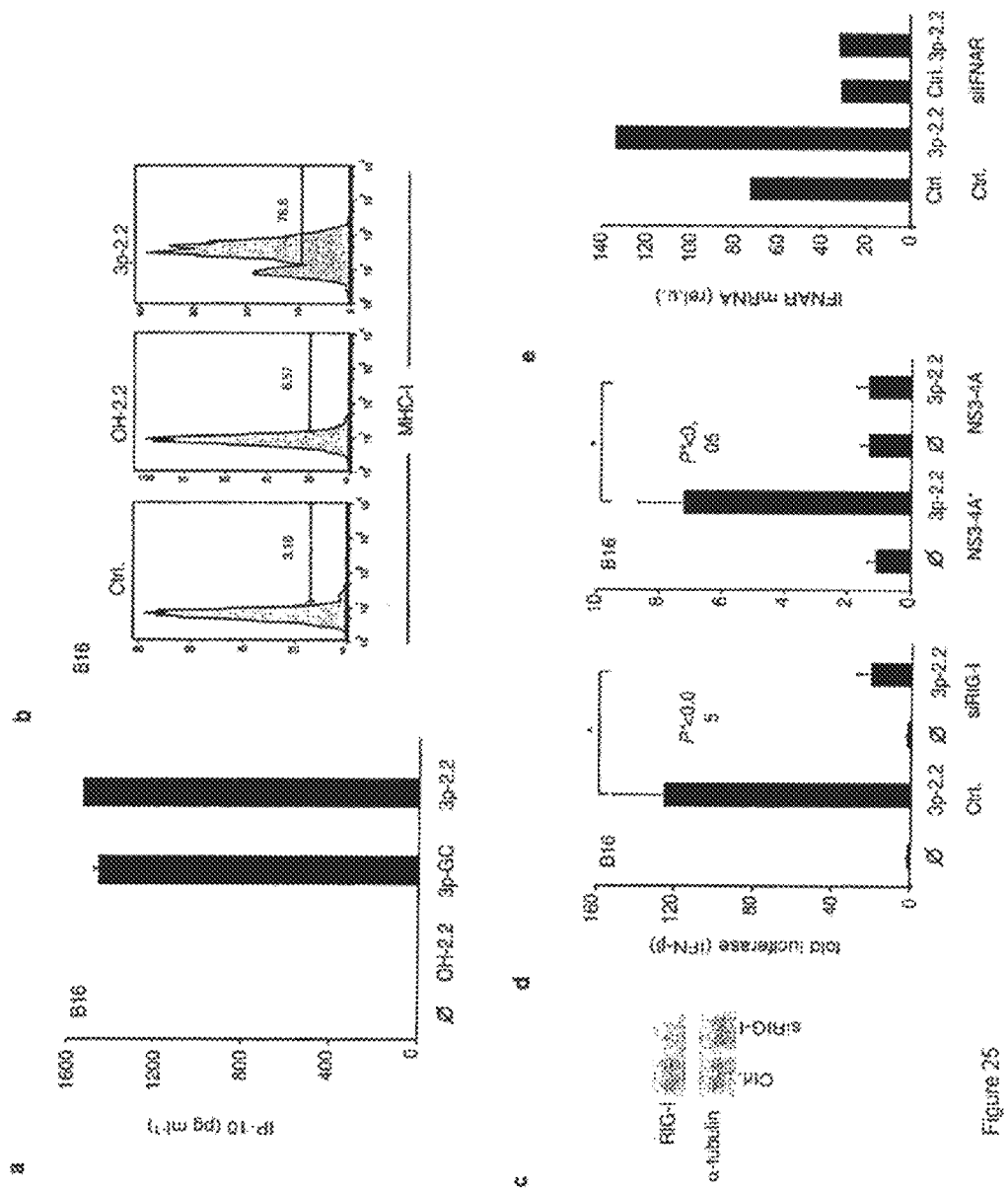

FIG. 25. 5'-triphosphate siRNA leads to RIG-I-dependent activation of B16 cells (a) B16 cells were treated with the indicated RNAs as described. IP-10 production was quantified in the supernatant by ELISA. Data are shown as means±SEM of two independent experiments. (b) B16 cells were treated with the indicated stimuli as described. After 24 h the number of MHC-I positive cells was determined by FACS-analysis. One representative histogram out of two independent experiments is shown. (c) B16 cells were transfected with a control siRNA or RIG-I siRNA at 1 μg/ml. 48 h after transfection protein expression of RIG-I was analysed by Western blot. (d) Left panel: B16 cells were co-transfected with control siRNA or RIG-I siRNA and an IFN-β promoter reporter construct driving luciferase. 24 h after transfection cells were stimulated with 3p-2.2 (1 μg/ml). 16 h after stimulation cells were analysed for IFN-β luciferase reporter activity. Data are shown as means±SEM of three independent experiments. Right panel: B16 cells were transfected with NS3-4A (encoding for a multifunctional serine protease of hepatitis C virus specifically cleaving and thereby inactivating two adaptor proteins, Cardif and Trif) or the inactive form NS3-4A*. 24 h after transfection B16 cells were stimulated with 3p-2.2 (1 μg/ml). 16 h after stimulation cells were analysed for IFN-β luciferase reporter activity. Data are shown as means±SEM of two independent experiments; P<0.05 (e) B16 cells were transfected with a control siRNA or IFNAR siRNA at 1 μg/ml. 24 h after siRNA transfection B16 cells were stimulated with 3p-2.2 (1 μg/ml) and 48 h after stimulation mRNA expression of IFNAR was analysed by quantitative RT-PCR. mRNA expression values were normalized to Hypoxanthine-phosphoribosyl-transferase (HPRT). Data are representative of two independent experiments.

Figure 26:
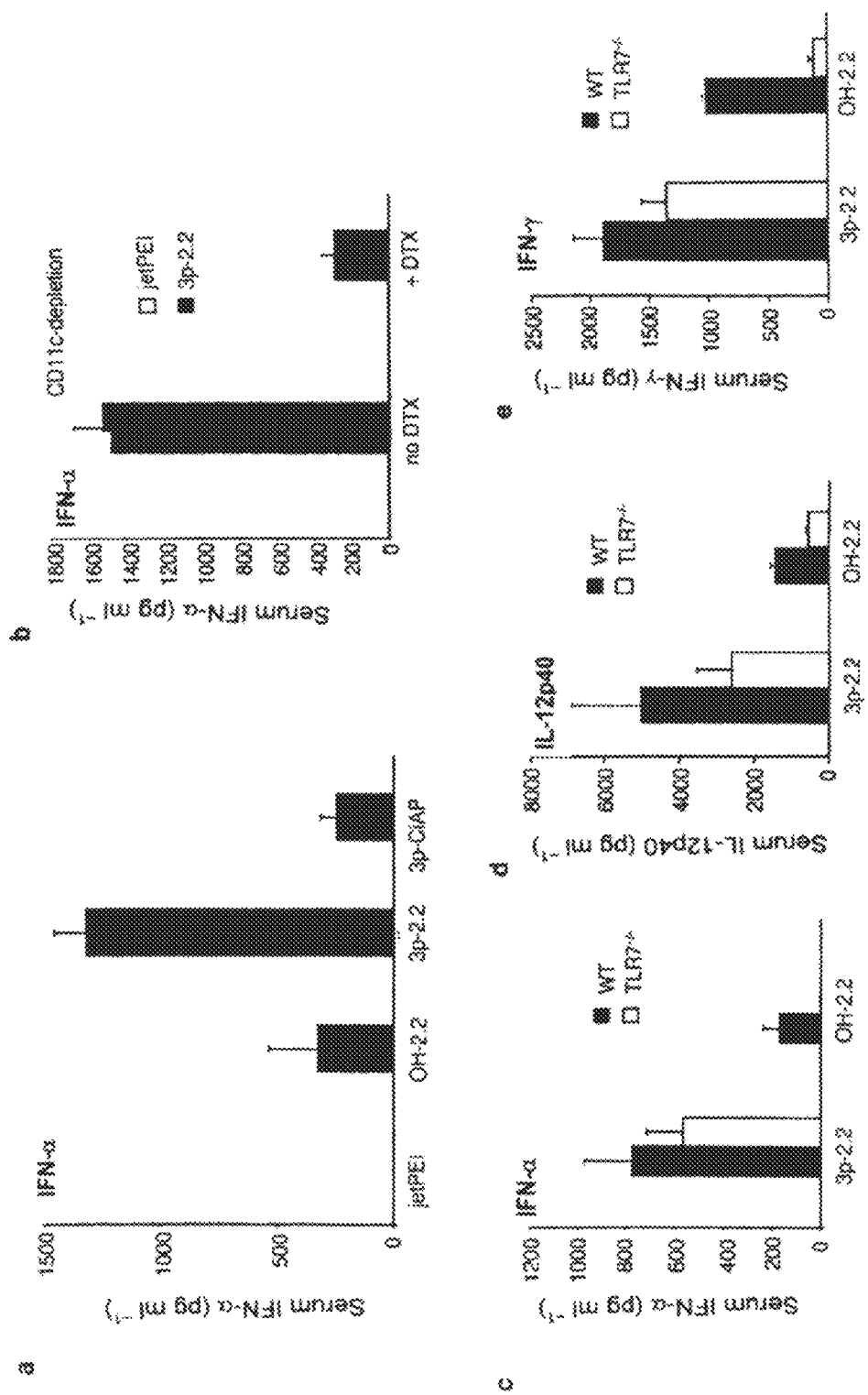

FIG. 26. 5'-triphosphate siRNA induced IFN-α secretion in vivo depends on the 5'-triphosphate end and on CD11c+ cell subsets, but is independent of TLR7

(a) C57BL/6 were administered with 50 μg of the indicated siRNAs. After 6 h mice were sacrificed and serum was analysed for IFN-α secretion. Data are shown as means±SEM of two independent experiments. (b) CD11c-DTR transgenic mice were injected i.p. with 100 ng DT or PBS (day 0). 24 h after injection mice were administered with 50 μg of 3p-2.2 or jetPEI. After 6 h mice were sacrificed and serum was analysed for IFN-α. Data are shown as means+/−SEM of two mice per group and are representative of two independent experiments. (c-e) C57BL/6 and TLR7−/− mice were treated as described in Material and Methods. After 6 h mice were sacrificed and serum was analysed for IFN-α (c), IL-12p40 (d) and IFN-γ (e) by ELISA. Data are shown as means±SEM of three independent experiments.

Figure 27:
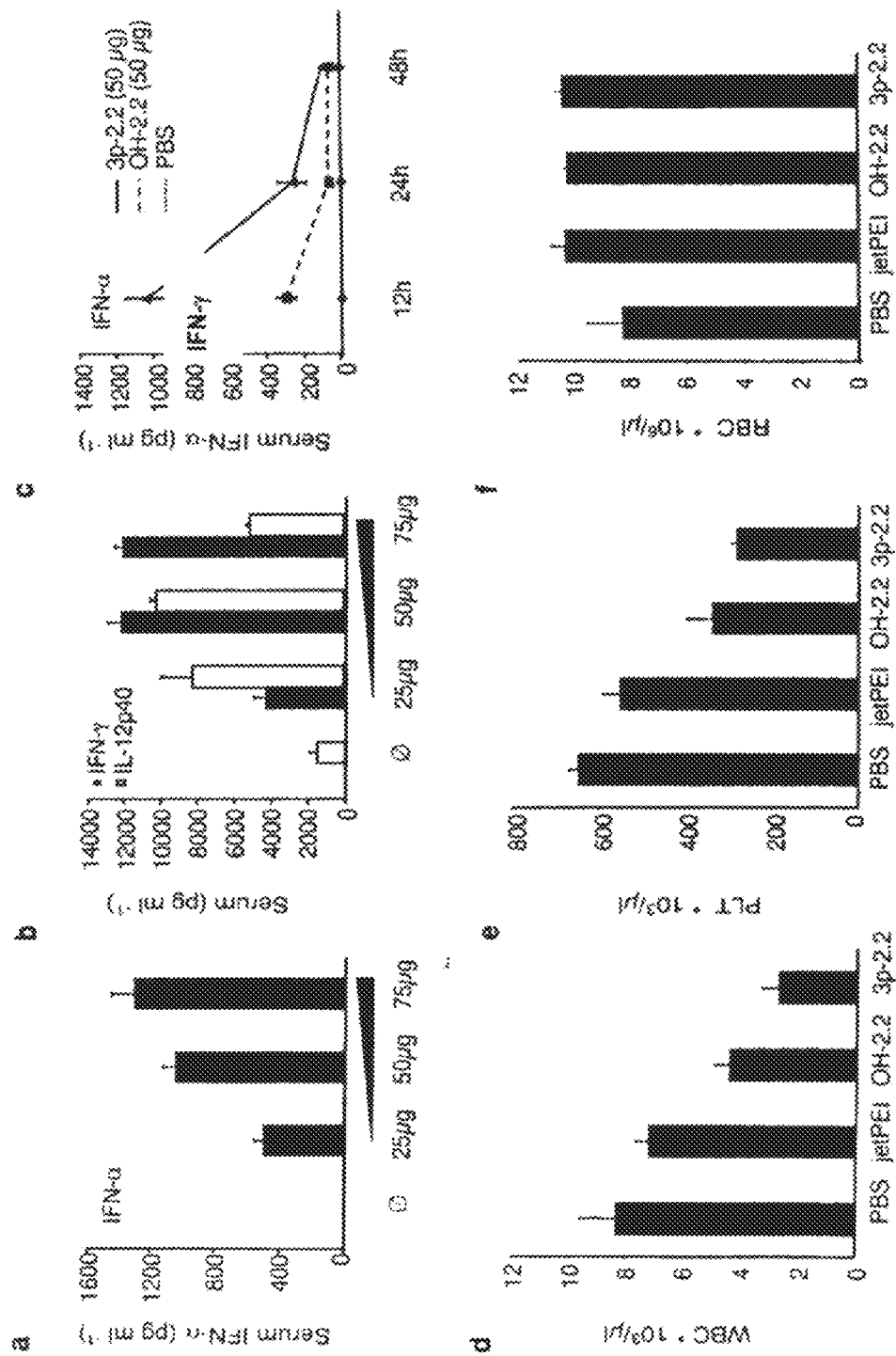

FIG. 27. 5'-triphosphate siRNA enhances the production of serum cytokines in vivo C57BL/6 mice were injected intravenously with increasing doses of 3p-2.2 (25, 50 or 75 μg/mouse). Serum was collected after 6 h. Cytokine levels of IFN-α (a) and IL-12p40 and IFN-γ (b) were determined by ELISA. (c) C57BL/6 mice were injected with 3p-2.2 and OH-2.2 and serum was collected 12 h, 24 h, and 48 h after injection. Serum cytokine levels of IFN-α were determined by ELISA. Data are shown as means±SEM of two independent experiments. (d-f) C57BL/6 mice were treated with 3p-2.2 and OH-2.2 and blood was collected after 48 h and processed as EDTA plasma for measurement of (d) leucocytes (WBC), platelets (PLT) (e) and erythrocytes (RBC) (f). Data are shown as means±SEM of two independent experiments.

Figure 28:
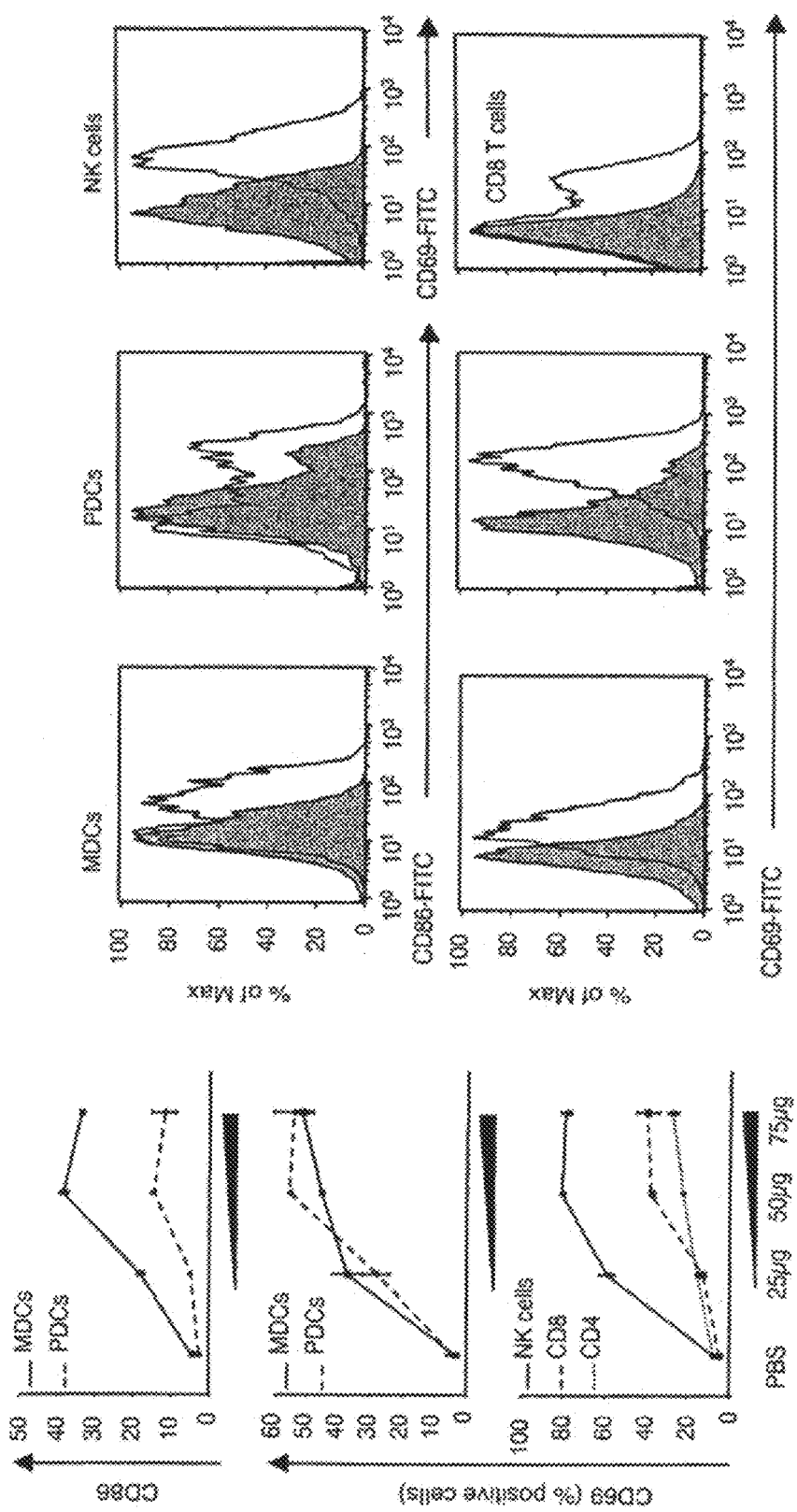

FIG. 28. 5'-triphosphate siRNA activates immune cell subsets in vivo C57BL/6 mice were injected with increasing doses of 3p-2.2 (25, 50 or 75 µg/mouse). Left panel: Spleen cells were isolated 48 h after injection and CD86 or CD69 expression was analysed on PDCs, MDCs, NK cells, CD4 T cells and CD8 T cells by flow cytometry. Data are shown as means±SEM of two independent experiments. Right panel: Histograms of one representative experiment after stimulation with 50 µg 3p-2.2 is shown (grey bar, PBS treated control mice; white bar, 3p-2.2 treated mice).

Figure 29:
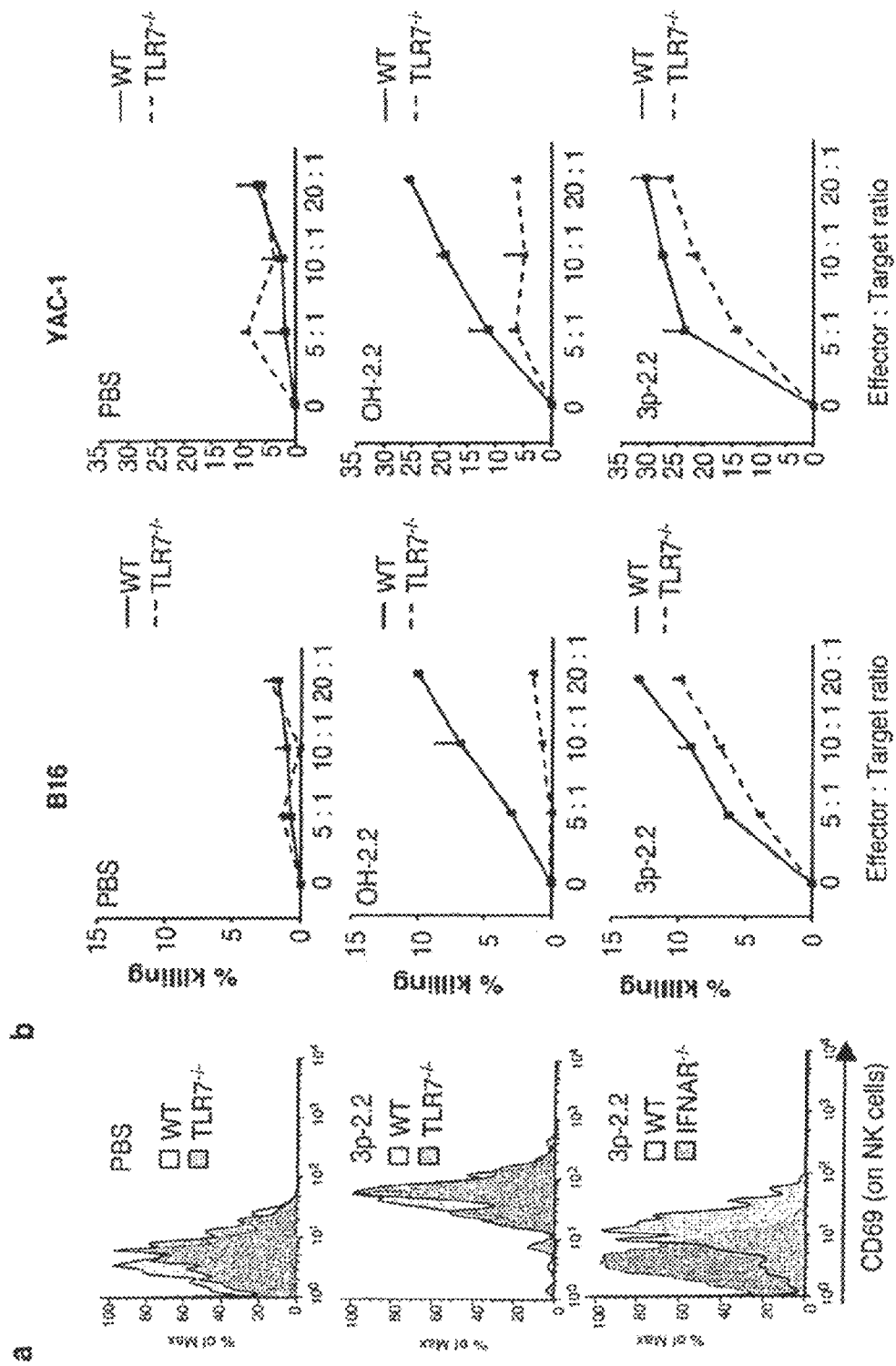

FIG. 29. 5'-triphosphate siRNA induces NK cell cytotoxicity independent of TLR7
(a) Activation of splenic NK cells isolated from 3p-2.2-injected mice strictly depends on IFNAR, but not on TLR7. Wild-type (WT), TLR7- or IFNAR-deficient mice were injected with 3p-2.2 or PBS as described. After 16 h, splenic NK cells were isolated with DX5 (anti-CD49b) microbeads and assayed for activation (CD69) by flow cytometry. (b) WT or TLR7-deficient mice were injected with OH-2.2, 3p-2.2 or PBS as described. After 16 h, NK cells were isolated from spleens using DX5 (anti-CD49b) microbeads and NK cytotoxicity against B16 cells was measured by 51Cr release assay. YAC-1 cytotoxicity of splenic NK cells was tested at the same time since YAC-1 cells are known to be targets for NK cells.

Figure 30:
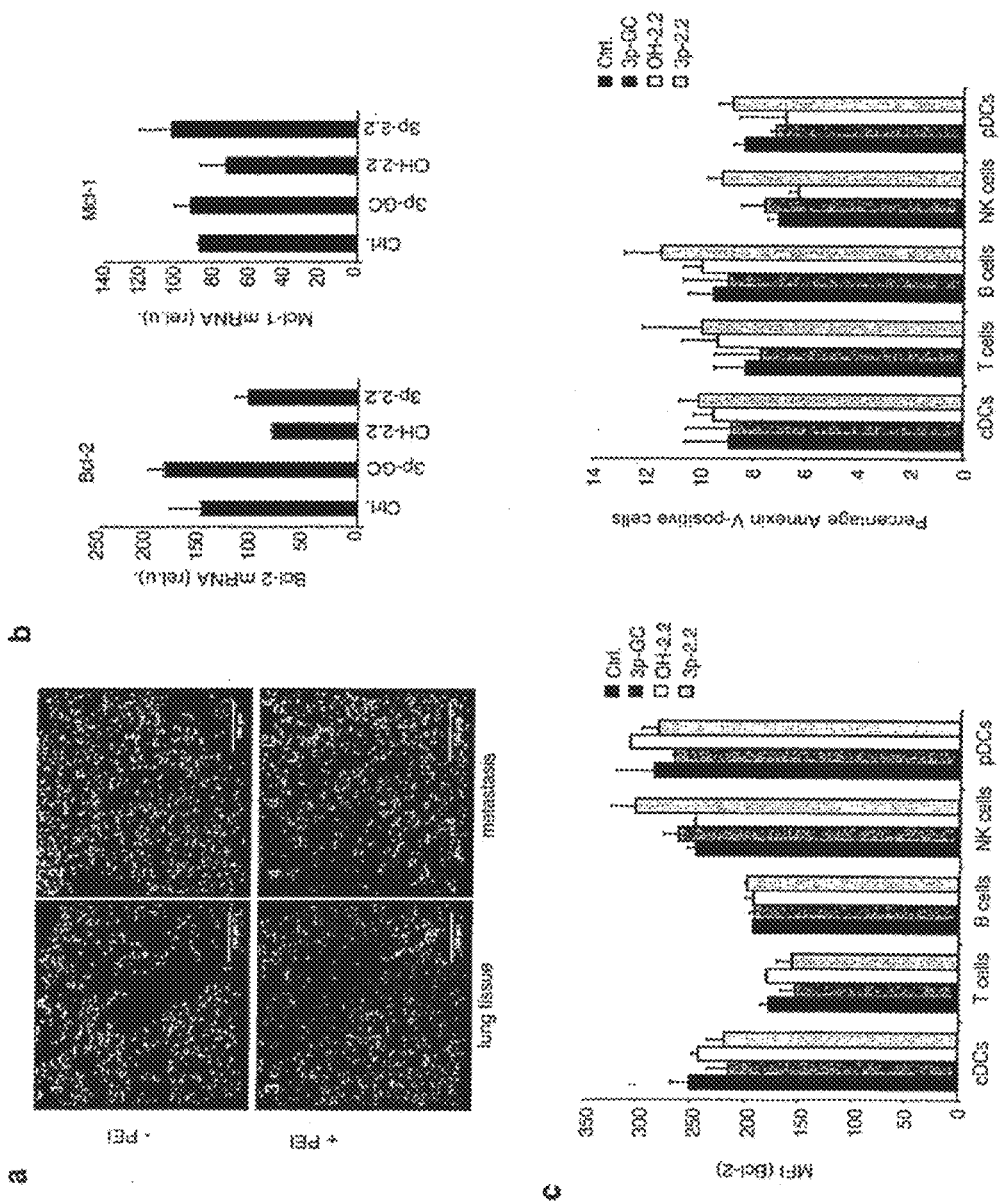

FIG. 30. Uptake of FITC-labeled siRNA in lung metastases and fate of immune cell subsets in vivo after 5'-triphosphate siRNA administration.
(a) B16 cells were intravenously injected into C57BL/6 mice and 14 days after tumor inoculation, a single dose of FITC-labeled siRNA (100 µg) was administered intravenously. After 6 h the mice were sacrificed and various tissues including lungs were excised and the uptake of FITC-labeled siRNA was analysed by confocal microscopy. One representative out of two independent experiments after injection with 100 µg FITC-labeled siRNA is shown. (b) Total RNA was extracted from metastatic lungs treated with the indicated RNAs for 24 h and analysed by quantitative RT-PCR for expression of Bcl-2 and Mcl-1. Relative gene expression was expressed as a ratio of the expression level of the gene of interest to that of hypoxanthine-phosphoribosyl-transferase (HPRT) RNA determined in the same sample. Data are presented as means+/−SD out of two mice/group. (c) C57BL/6 mice were administered with 50 µg of the indicated siRNAs. 24 h after injection spleens were excised and immune cell subsets were analysed for gene-silencing (left panel) and apoptosis (right panel) by flow cytometry. Means+/−SEM out of two independent experiments are depicted.

FIG. 31. Insertion of two mismatches in the binding site of anti-Bcl-2 siRNA
For rescue experiments two central silent mutations (C610A and A612G at amino acid (AA) position 204) were introduced in the target site of 2.2-siRNA against murine bcl-2 and subsequently sequenced for confirmation (data not shown). cDNA encoding wild-type murine bcl-2 served as template. CTATATGGCCCCAGCATGAGGCCTCTGTTT-GATTTCTCC was used as forward primer (mBcl-2 forward). The central mismatches between the anti-bcl-2 siRNA and the bcl-2 target site result in disrupted base pairing and therefore in the loss of function of the synthetic (OH-2.2) and the 5'-triphosphate siRNA (3p-2.2).

Figure 32:
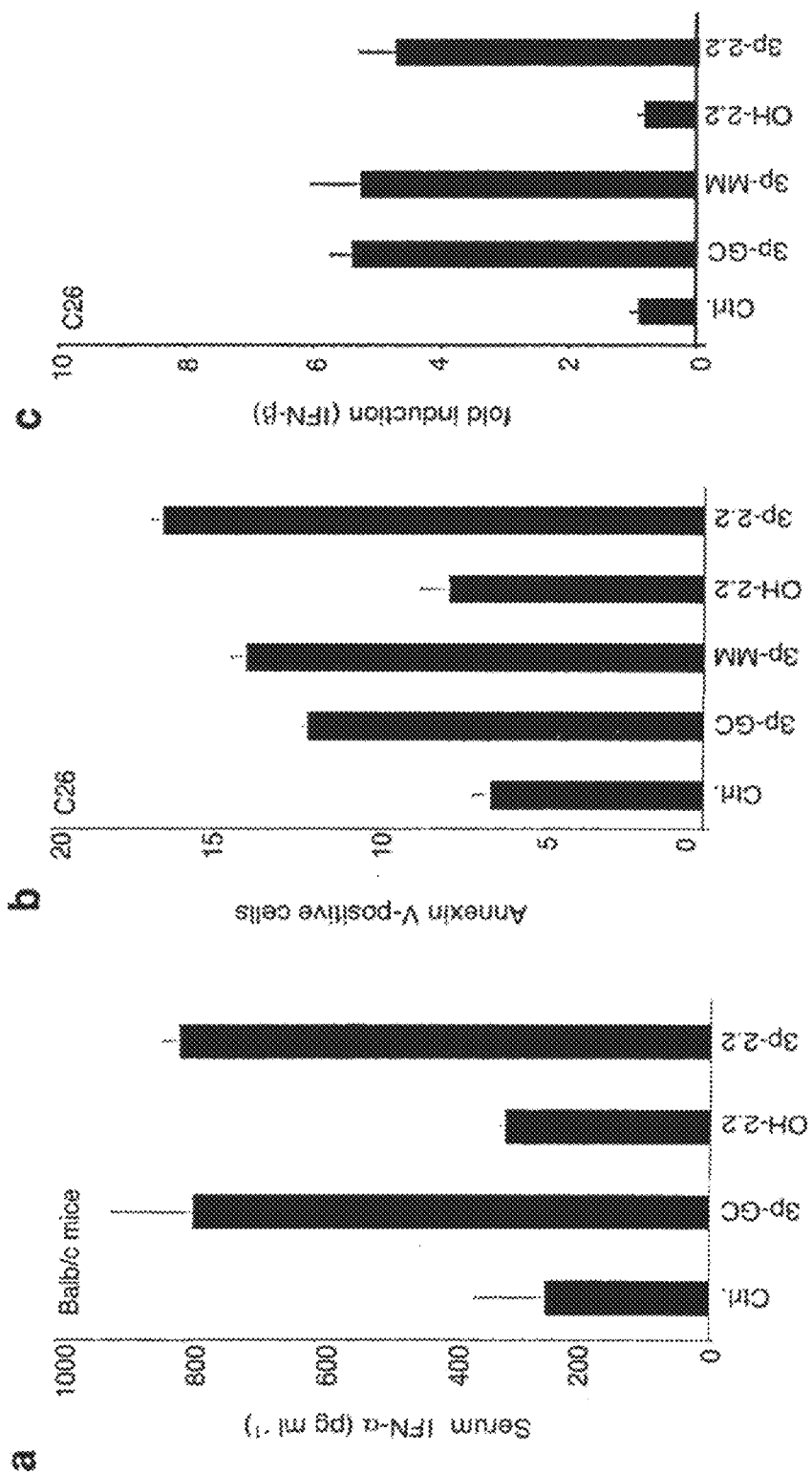

FIG. 32. 5'-triphosphate siRNA leads to RIG-I-dependent apoptosis and activation of C26 cells
(a) Groups of four tumor-bearing Balb/c mice were injected with control RNA (Ctrl.), OH-2.2, 3p-GC or 3p-2.2 (50 µg/Mouse) as described. Sera were collected after 6 h and IFN-α levels determined by ELISA. Data are shown as mean+/−SEM of four mice/group. (b) C26 cells were treated with the indicated stimuli as described. After 24 h the number of Annexin-V positive cells was determined by FACS-analysis. Data are presented as means+/−SEM out of two independent experiments. (c) C26 cells were transfected with an IFN-β promoter reporter construct driving luciferase. 24 h after transfection cells were stimulated with the indicated siRNAs (1 µg/ml). 24 h after stimulation cells were analysed for IFN-β luciferase reporter activity. Data are shown as means±SEM of three independent experiments.

Figure 33:
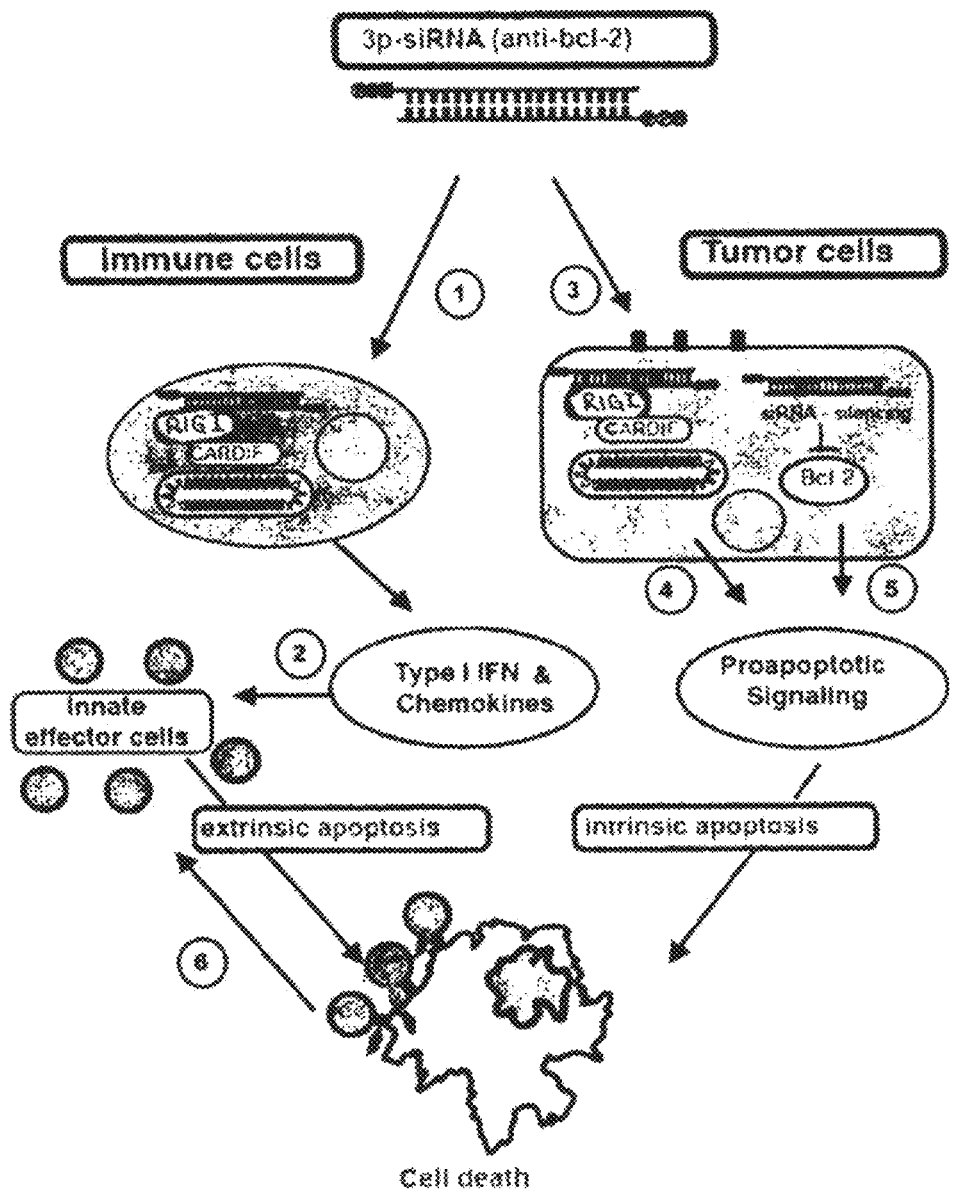

FIG. 33: Schematic diagram of the potential anti-tumor mechanism elicited by 3p-siRNA 3p-2.2 contains two clearly distinct functional properties, a) gene silencing and b) RIG-I activation. 3p-2.2 is able to trigger the following distinct anti-tumor mechanism: i) RIG-I is expressed in immune cells including tumor cells; activation of RIG-I leads to direct (1) and indirect activation (2) of immune cell subsets (NK cells, CD8 and CD4 T cells) but also provokes innate responses directly in tumor cells (type I IFNs and chemokines) (3). ii) In addition RIG-I activation directly induces apoptosis in melanoma cells (which are sensitive to RIG-I mediated apoptosis) (4) and iii) silencing of bcl-2 induces apoptosis in cells that depend on bcl-2 overexpression (5). The activation of RIG-I in tumor cells may synthesize these cells for specific destruction by innate effector cells (6).

DETAILED DESCRIPTION OF THE INVENTION

Initially, it was reported that in vitro transcribed siRNAs (small-interfering RNA) which bear 5' triphosphate, but not synthetic siRNAs which bear 5' OH, stimulated the production of type I IFN from selected cell lines[20, 21]. However, the molecular mechanism which led to the induction of type I IFN was not known.

Subsequently, it was reported that in vitro transcribed long dsRNA (equal or longer than 50 bp) was detected by RIG-I[10].

Almost at the same time, it was reported that synthetic blunt-ended short dsRNAs 21-27 bp in length and without any 5' phosphate group were ligands for RIG-I[16]. Furthermore, it was reported that 2-nucleotide 3' overhangs, and to a lesser extend, 5' overhangs, inactivated RIG-I[16]. It was postulated that blunt end was the molecular signature recognized by RIG-I Shortly thereafter, in vitro transcribed short ssRNA and dsRNA bearing 5' triphosphate were identified as the ligands for RIG-I[15, 16]. Furthermore, it was shown that in vitro transcribed short dsRNAs having the same sequences as those used in Marques T J et al. (2006)[16] stimulated IFN-α production in purified primary human monocytes to the same degree, regardless whether the dsRNA had blunt ends or 3' overhangs[15]. In other words, in the presence of 5' triphosphate, the end structure of a dsRNA oligonucleotide did not affect the IFN-α-inducing activity of the oligonucleotide; the presence of 3' overhangs did not inactivate RIG-I.

This finding confirms the notion that 5' triphosphate is a molecular signature recognized by and activates RIG-I[16, 19] and suggests that blunt end is not a molecular signature that activates RIG-I[16].

At the same time, it was reported that single-stranded genomic RNA from influenza A which bears 5' phosphates was recognized by RIG-I[26].

More recently, it was reported that the C-terminal regulatory domain RD of RIG-I was responsible for the recognition of the 5' triphosphate on in vitro transcribed ssRNA ligands[26].

Almost at the same time, it was reported that dsRNA 25-nucleotide long with a 5' monophosphate was also a ligand for RIG-I[24]. Furthermore, ssRNA bearing 5' triphosphate was confirmed to be a ligand for RIG-I[24]. Moreover, it was reported that a blunt-ended dsRNA bearing a 5' monophosphate was more potent at inducing an IFN response than that having 3' overhangs[24]. However, counterintuitively, it was also reported that 5' monophosphate in dsRNA was not required for interaction with the C-terminal domain of RIG-I whereas 5' triphosphate did interact with the C-terminal domain. In addition, it was reported that the ability of a dsRNA oligonucleotide to induce an IFN response was inversely correlated with the unwinding activity by the helicase domain, which contradicts earlier report that blunt end was not only required for the induction of an IFN response, but also for helicase activity[16].

Also very recently, it was reported that the presence of 2 or 3 G's at the 5' end of shRNAs generated by in vitro transcription obliterated the ability of the 5' triphosphate-bearing RNA to induce IFN-β production via the RIG-I pathway[30]. Notably, the shRNAs bearing two 5' G's, which had two G-U wobble base pairs at the end, i.e., a blunt end, were completely inactive in inducing an IFN response.

In summary, a number of structurally different RNA molecules have been reported to be the ligand for RIG-I and different molecular signatures have been postulated to be recognized by RIG-I. The data in the prior art were inconsistent and at times conflicting with regard to the molecular signatures that were important for activating RIG-I. In other words, there was no consensus in the prior art with regard to the critical molecular signature(s) for RIG-I recognition and activation.

Figure 1:
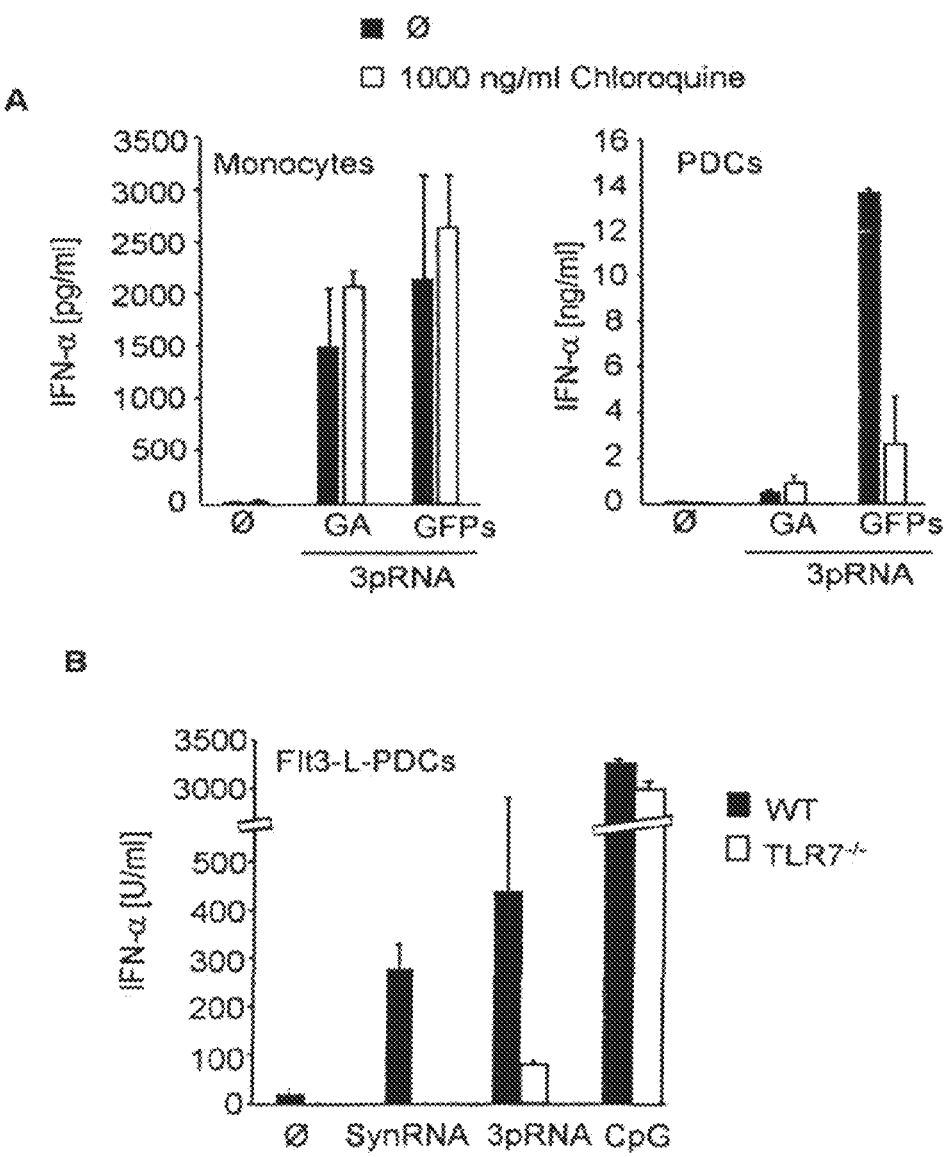
FIG. 1. Recognition of 3pRNA occurs through differential pathways in monocytes and PDCs. (A) Monocytes and PDCs were pre-incubated with 1000 ng/ml chloroquine (white bars) or left untreated (black bars). After 30 min cells were stimulated with 3pRNA GA or 3pRNA GFPs complexed with lipofectamine (as indicated) or control (no nucleic acid). Supernatants were collected 20 h post stimulation and IFN-α production was determined by ELISA. The results are representative for two experiments and mean±SEM is shown. (B) Sorted PDCs from Flt3-L-induced bone marrow cultures of wild-type (WT; black bars) and TLR7-deficient mice (TLR7$^{-/-}$; white bars) were transfected with 200 ng of SynRNA, 3pRNA and CpG ODN2216 (3 μg/ml). After 24 h, IFN-α production was determined by ELISA. Data are expressed as the mean±SEM of two independent experiments.

Even though various immune cell types, such as monocytes, plasmacytoid dendritric cells (PDCs), and myeloid dendritic cells (MDCs), are capable of producing IFN-α in response to stimulation by double-stranded RNA oligonucleotides bearing 5' triphosphate (hereinafter, "3pRNA"; unpublished data from the present inventors), the recognition of such double-stranded 3pRNA oligonucleotides appears to be mediated by different receptors in different cell types. Whereas PDCs appear to utilize TLR7 primarily, monocytes appear to utilize RIG-I primarily (Example 1; FIG. 1). In fact, PDC is the only cell type that produces a significant amount of IFN-α upon stimulation with an appropriate TLR ligand. In contrast, other immune cells, such as myeloid cells, produce cytokines other than IFN-α in response to stimulation by TLR ligands. Therefore, monocytes (without contaminating functional PDCs) are ideal for studying the mechanism of ligand recognition by and the activation of RIG-I, with IFN-α production as the readout.

Figure 2:
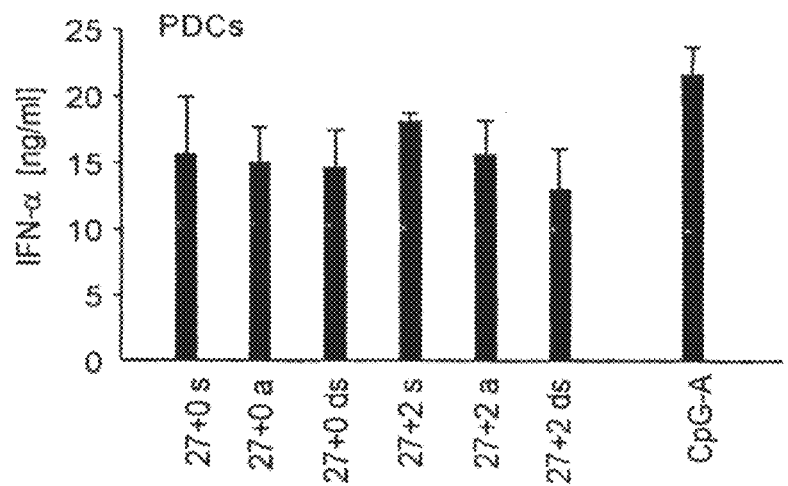
FIG. 2. Blunt end synthetic dsRNA is a poor inducer of IFN-α in monocytes. (A-B) Synthetic ssRNA and dsRNA with (27+2) or without (27+0) 2-nt overhangs were transfected into PDCs and monocytes in complex with lipofectamine 2000. CpG ODN 2216 (3 µg/ml) and 3pRNA GFPs (200 ng) were used as a positive control stimulus for TLR and RIG-I, respectively. The levels of IFN-α production were analyzed by ELISA 24 h after stimulation and are depicted as mean±SEM of two independent experiments.
Figure 2:
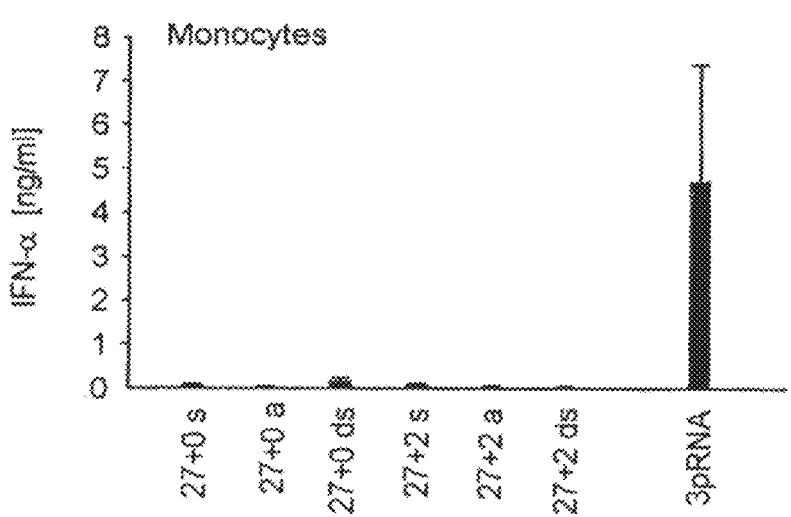
Figure 6:
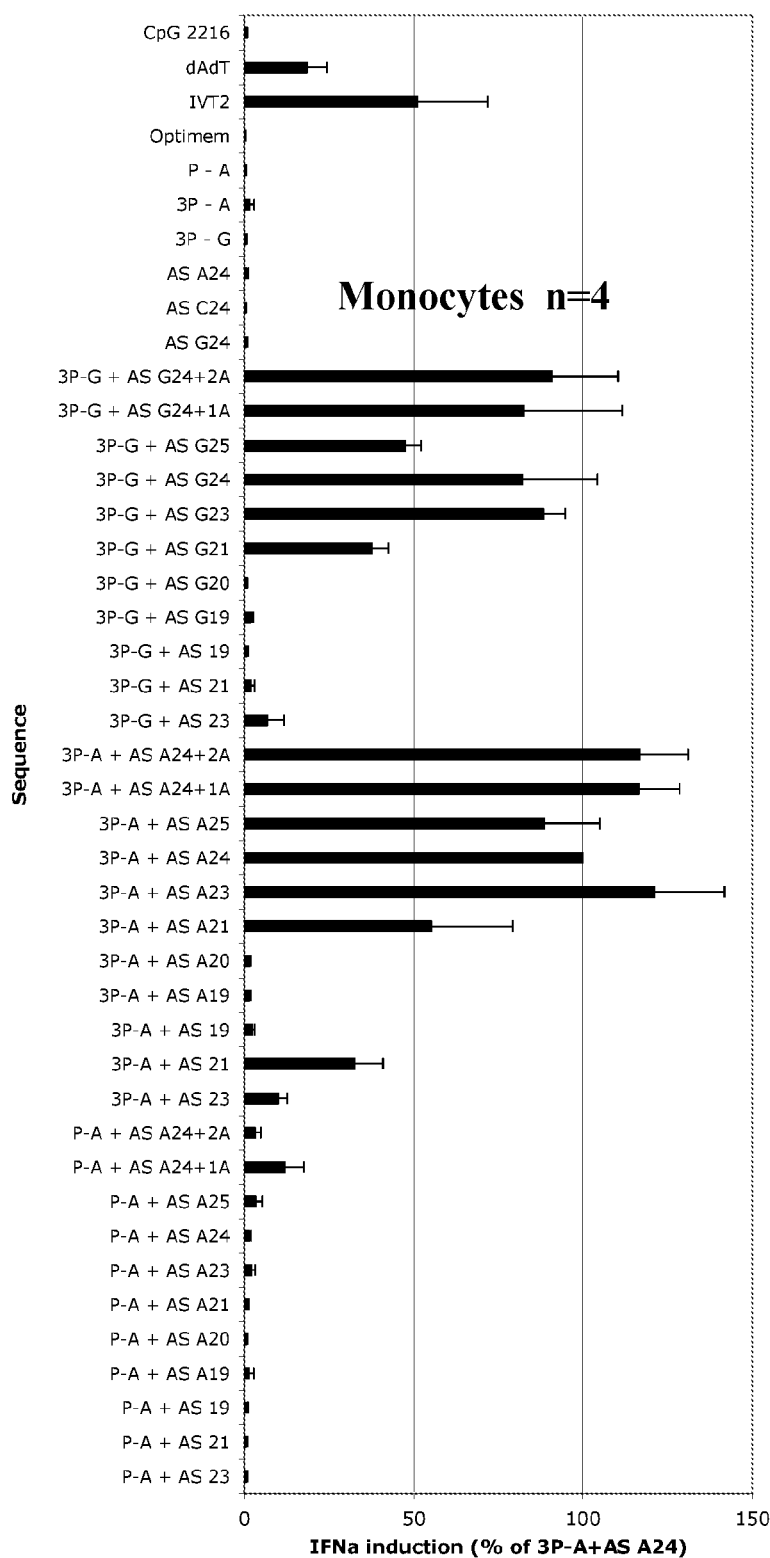

The present inventors stimulated purified primary human monocytes with the same synthetic blunt-ended short dsRNA without any 5' phosphate as that used in Marques T J et al. (2006)[16], and found surprisingly that there was no IFN-α production (Example 2; FIG. 2, sample "27+0 ds"). Furthermore, the present inventors stimulated purified primary human monocytes with a synthetic blunt-ended short dsRNA bearing a 5' phosphate similar to that used in Takahasi et al. (2008)[24], and found surprisingly that there was little or no IFN-α production (Example 3; FIG. 6, samples with "P-A" in the name). Theses findings contradict suggestions in the prior art that blunt-end was a molecular signature recognized by RIG-I and was capable of activating RIG-I in the absence of 5' triphosphate[16, 24].

Figure 4:
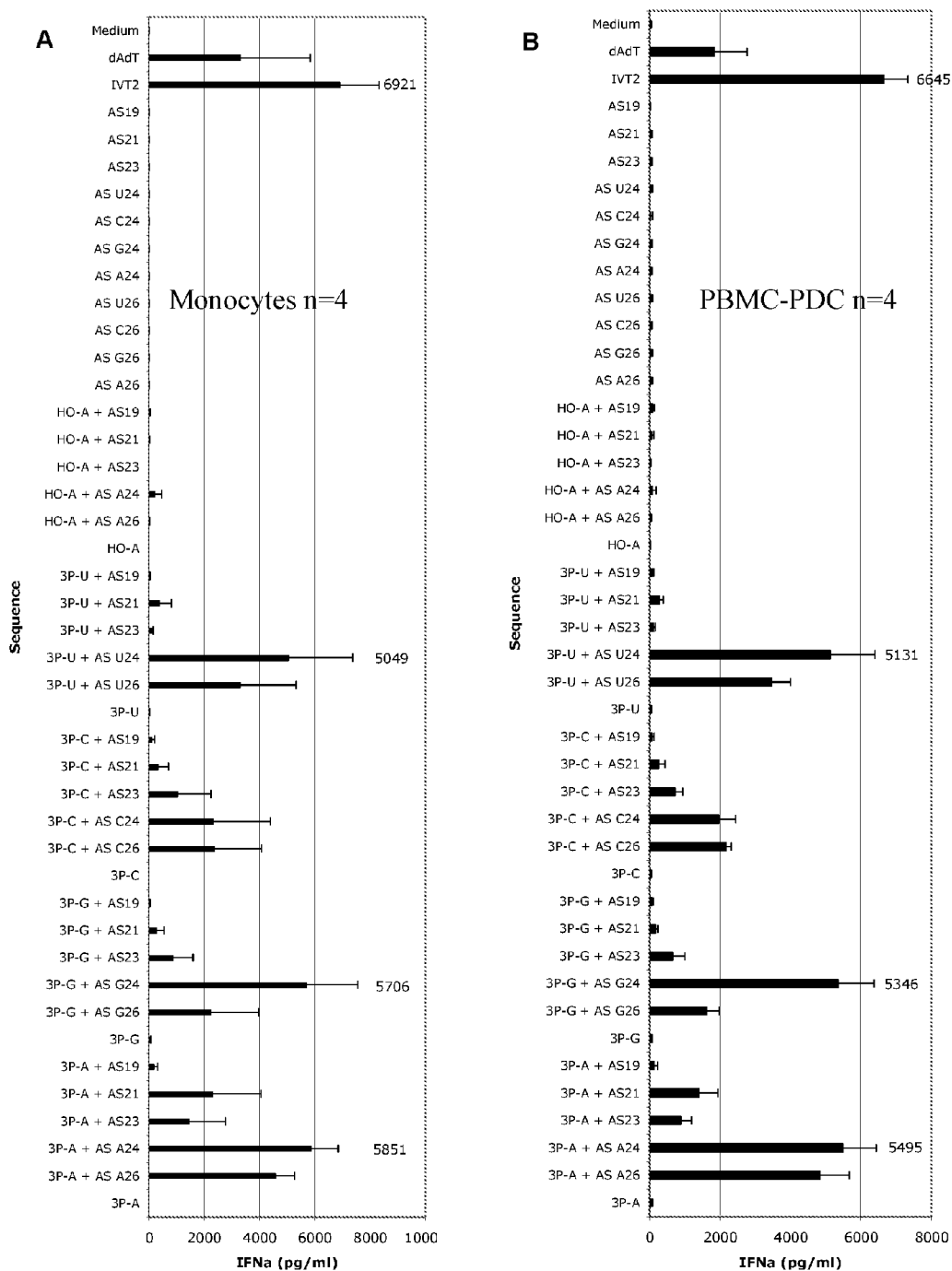
FIGS. 4-6. Blunt end at the end bearing the 5' triphosphate augments the immunostimulatory activity of synthetic double-stranded 3pRNA oligonucleotides. Purified monocytes, PDC-depleted PBMCs and PBMCs pre-treated with chloroquine were transfected with the indicated single-stranded or double-stranded synthetic RNA oligonucleotide. IFN-α production was analyzed 24 hours after stimulation. Data from three or four independent donors were summarized and are depicted as mean values±SEM.
Figure 4:
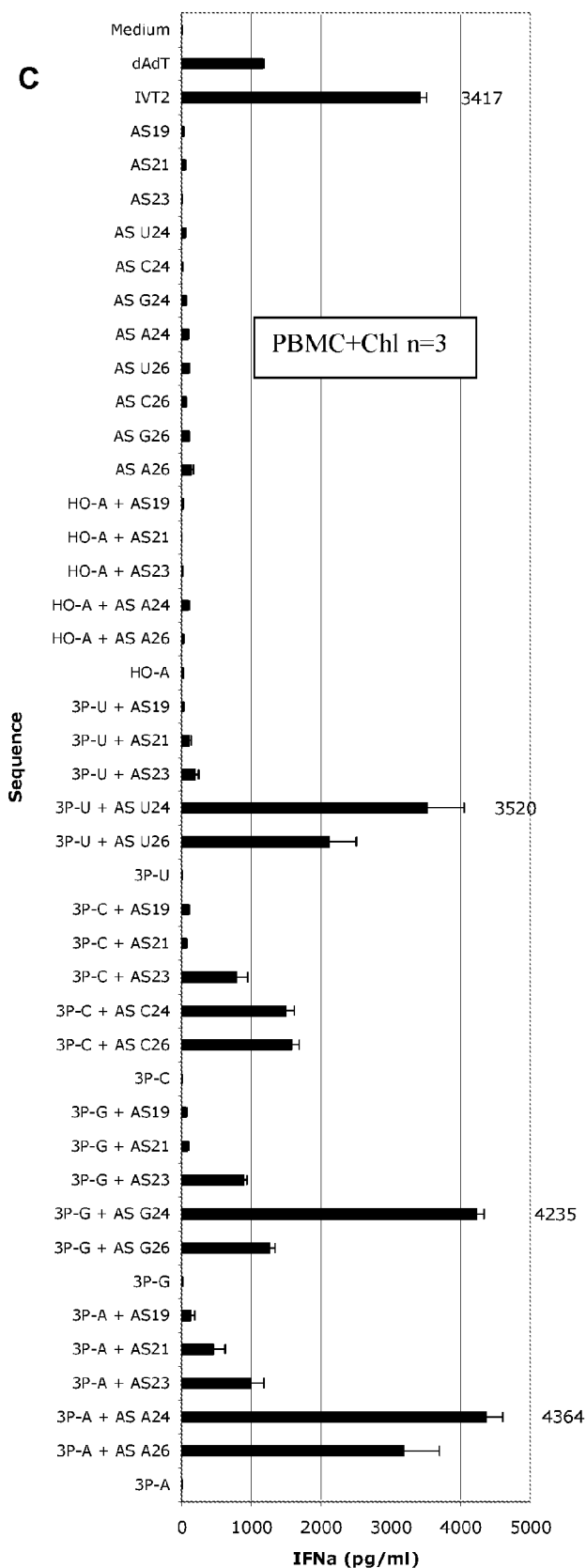
Figure 5:
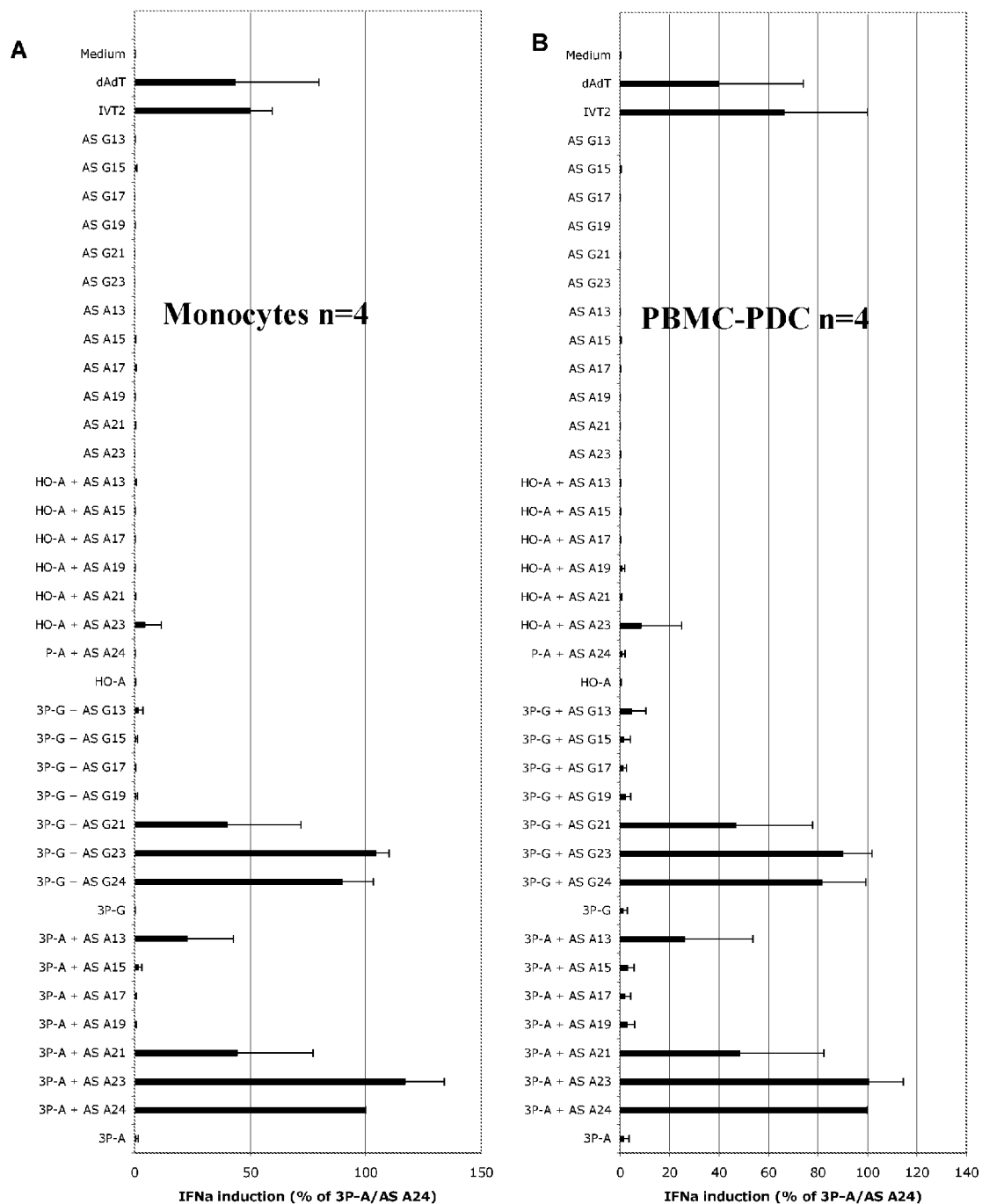
Figure 5:
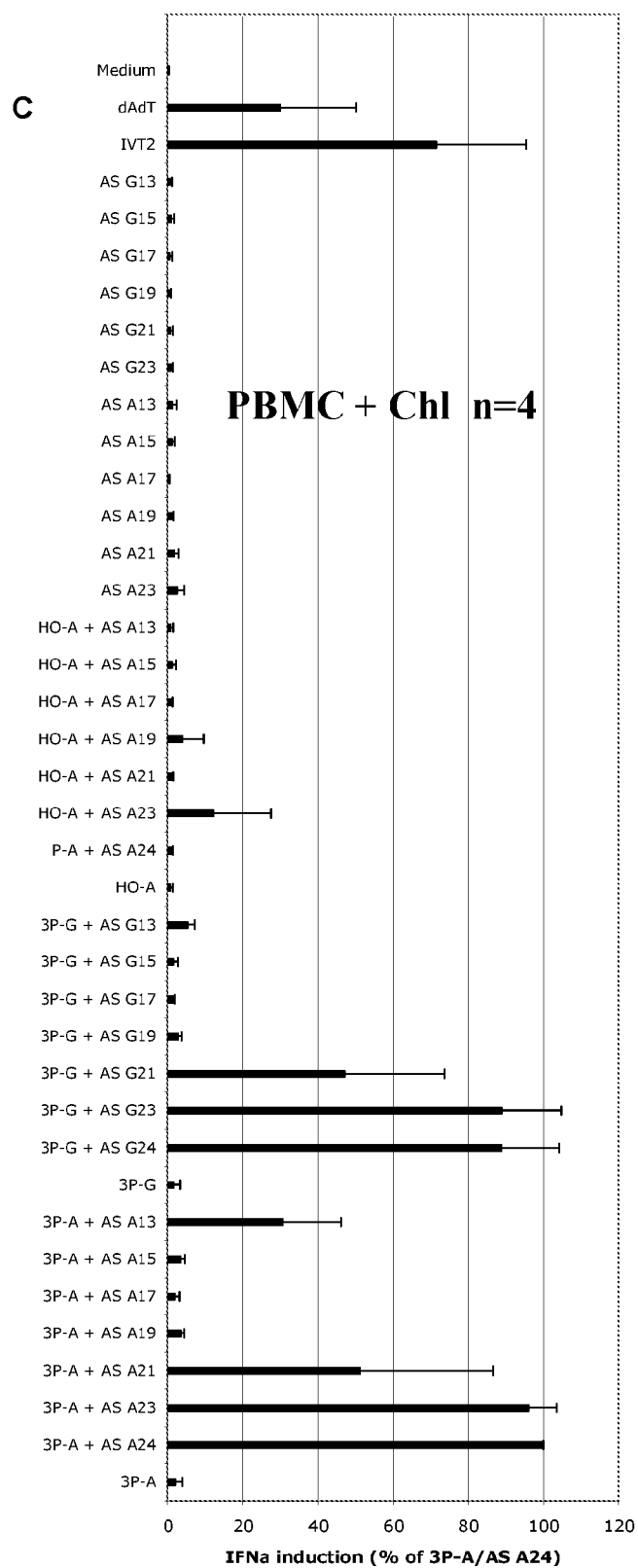

However, very surprisingly, when the present inventors stimulated purified primary human monocytes with synthetic dsRNA oligonucleotides bearing a 5' triphosphate, they found that the IFN-inducing activity of the dsRNA oligonucleotides was dramatically enhanced when the end bearing the 5' triphosphate was blunt (Example 3; FIGS. 4-6, samples "3P–X+AS X24", "3P–X+AS X24+A", "3P–X+AS X24+2A", "3P–X+AS X23"). The same results were obtained with peripheral blood mononuclear cells (PBMC) depleted of PDCs or PBMCs pre-treated with chloroquine, in which cases IFN-α production from PDCs was excluded.

This finding is surprising because it contradicts earlier report that the presence of blunt end did not enhance the IFN-inducing activity of dsRNA bearing 5' triphosphate[16]. Furthermore, this finding demonstrates for the first time that the blunt end has to be on the same side as the 5' triphosphate to be recognized by and activate RIG-I.

This surprising finding suggests that both 5' triphosphate and blunt end are molecular signatures recognized by RIG-I. Whereas 5' triphosphate is the primary molecular signature recognized by RIG-I, blunt end is a secondary one which is not capable of activating RIG-I on its own but is capable of augmenting RIG-I activation in the presence of 5' triphosphate. Furthermore, the fact that the activity-enhancing effect of the blunt end was only observed when the blunt end was the end that bore the 5' triphosphate suggests that 5' triphosphate and blunt end are recognized by functional domains or sub-domains of RIG-I which are adjacent to each other in the 3-dimensional structure. In particular, it is highly likely that 5' triphosphate and blunt end are recognized by the same domain of RIG-I, the C-terminal regulatory domain.

The present finding is surprising also because the present inventors found that dsRNA oligonucleotides as short as 21 base pairs (bp) were capable of activating RIG-I and inducing significant IFN-α, production when they bore 5' triphosphate and a blunt end, which is in contrast to the suggestion of Marques et al. (2006) that a length of 25 bp was required for consistent RIG-I activation[16].

Moreover, the present inventors found that the RIG-I-activating and IFN-α-inducing activity of a dsRNA bearing 5' triphosphate and blunt end depended on the identity of the 5' nucleotide bearing the 5' triphosphate. Whereas a dsRNA having a 5' adenosine (A) was more potent than one having a 5' guanosine (G) or one having a 5' uridine (U), they were all more potent than one having a 5' cytidine (C).

Without being bound by any theory, it is hypothesized that chemically synthesized dsRNA oligonucleotides are essentially homogenous populations, wherein the oligonucleotides in each population are chemically well-defined and have essentially the same length, sequence and end structures. In contrast, dsRNA oligonucleotides obtained via in vitro transcription have variable lengths and end structures.

The present inventors have thus identified synthetic dsRNA oligonucleotides bearing at least one 5' triphosphate and at least one blunt end at the same end as the 5' triphosphate, with a reference for A as the 5' triphoshpatebearing nucleoside, as highly potent agents for activating RIG-I and inducing type I IFN production from RIG-I-expressing cells.

In addition, it has been reported that certain nucleoside modifications of the RNA, which occur during eukaryotic post-transcriptional processing of endogenous RNA, abrogated the IFN-α-inducing activity of 5' triphosphate-bearing RNA molecules[15, 19]. One of these modifications was 2'-O-methylation.

However, surprisingly, the present inventors found that when the most 3' nucleotide which base pairs with the most 5' ribonucleotide bearing the 5' triphosphate at the blunt end was 2'-O-methylated, the IFN-α-inducing activity of the oligonucleotide was not only not abrogated, but enhanced, providing yet another molecule signature which enhances the type I IFN-inducing activity of an oligonucleotide. At the same time, 2'-O-methlyation of a nucleotide at any position other than the above-mentioned position resulted in a decrease in the type I IFN-inducing activity of the oligonucleotide. This finding opens up the possibility of modulating the type I IFN-inducing activity of an oligonucleotide bearing a 5' triphosphate by 2'-O-methylation at specific positions. Whereas the type I IFN-inducing activity of a 5' triphosphate-bearing olignucleotide may be enhanced by 2'-O-methylation of a most 3' nucleotide which base pairs with a most 5' ribonucleotide bearing a 5' triphosphate at a blunt end, the type I IFN-inducing activity may be reduced by 2'-O-methylation of any other nucleotide, especially the second most 3' nucleotide which is just 5' of the most 3' nucleotide which base pairs with a most 5' ribonucleotide bearing a 5' triphosphate at a blunt end.

Furthermore, the present inventors found that the double stranded oligonucleotides with 5'-triphosphate ends having gene-silencing activity are particularly useful against melanoma, especially anti-bcl-2 siRNA with 5'-triphosphate ends (3p-siRNA).

Recognition of 5'-triphosphate by the cytosolic antiviral helicase retinoic-acid-induced-protein-1 (RIG-I) activated innate immune cells such as dendritic cells and directly induced interferon and apoptosis in tumor cells. These RIG-1-mediated activities synergized with siRNA-mediated gene silencing, especially bcl-2 silencing to provoke massive apoptosis of tumor cells in lung metastases in vivo. The therapeutic activity required NK cells and interferon, as well as silencing of bcl-2 as evidenced by rescue with a mutated bcl-2 target, by site-specific cleavage of bcl-2 mRNA in lung metastases and downregulation of bcl-2 protein in tumor cells in vivo. Together, 3p-siRNA represents a single molecule-based approach in which RIG-I activation on both the immune- and tumor cell level corrects immune ignorance and in which gene silencing governs key molecular events.

Through the mechanism of RNA interference (RNAi) these short double-stranded RNAs can be designed to target mRNAs encoding key regulators of tumor survival[48, 48]. A distinct and independent biological property of RNA oligonucleotides can be the activation of immunoreceptors specialized for the detection of viral nucleic acids. The ubiquitously expressed helicase RIG-I is one of two immunoreceptors that signal the presence of viral RNA in the cytosol of cells[11]. Specifically, RIG-I detects RNA with a triphosphate group at the 5'-end[15, 47]. Formation of such 5'-triphosphate RNA by RNA polymerases in the cytosol of cells is characteristic for most negative strand RNA viruses[48].

Since recognition of 3p-RNA by RIG-I is largely independent of RNA sequence, and gene silencing is not inhibited by the presence of a 5'-triphosphate, both biological activities can be combined in one short dsRNA molecule.

Such a short dsRNA molecule with triphosphate groups at the 5'-end (3p-siRNA) can be designed to target the mRNA of any key tumor survival factor. In the case of melanoma, such a molecule is Bcl-2. Bcl-2 was originally found in B cell lymphomas and is involved in the regulation of apoptosis. Overexpression of Bcl-2 is considered to be responsible for the extraordinary resistance of melanoma cells to chemotherapy[49-51].

Therefore the present invention is directed to oligonucleotide preparations having both immunoreceptor activation ability and gene-silencing activity. Preferably, the oligonucleotide preparations of the invention have Bcl-2-silencing and RIG-I activation ability.

Definitions

The articles "a" and "an" are used herein to refer to one or to more than one (i.e., at least one) of the grammatical object of the article. By way of example, "an element" means one element or more than one element.

All terms used herein bear the meanings that are established in the art unless otherwise noted. Techniques disclosed herein can be performed by a person skilled in the art following the present description and/or established protocols, such as those disclosed in Molecular Cloning: A Laboratory Manual (Sambrook et al., 1989, Cold Spring Harbour Laboratory, New York), Current Protocols in Molecular Biology (Ausubel et al., 2007, John Wiley & Sons, New York), and Current Protocols in Immunology (Coligan et al., 2007, John Wiley & Sons, New York).

The expressions "an RNA oligonucleotide bearing 5' triphosphate", "triphosphate RNA oligonucleotide" and "3pRNA oligonucleotide" are used interchangeably.

The expressions "structural motif" and "molecular signature" are used interchangeably.

Oligonucleotides

In the first aspect, the present invention provides an oligonucleotide preparation which comprises an essentially homogenous population of an oligonucleotide and which is capable of activating RIG-I and inducing an anti-viral response, in particular, a type I IFN response, more specifically, an IFN-α response.

The oligonucleotide has at least one blunt end and comprises at least 1 ribonucleotide at the 5' end at the blunt end, wherein the blunt end bears a 5' triphosphate attached to the most 5' ribonucleotide, wherein the 5' triphosphate is free of any cap structure, and wherein the blunt end is followed by a fully double-stranded section which is at least 19, preferably at least 21 base pair (bp) in length. In other words, the blunt end is an/the end of the fully double-stranded section.

By "fully double-stranded", it is meant that the double-stranded section is not interrupted by any single-stranded structures. An oligonucleotide section is fully double-stranded when the two stretches of nucleic acid forming the section have the same length and have sequences which are 100% complementary to each other. As established in the art, two nucleotides are said to be complementary to each other if they can form a base pair, either a Waston-Crick base pair (A-U, G-C) or a wobble base pair (U-G, U-A, I-A, I-U, I-C).

The double-stranded section is preferably at least 20 bp, 21 bp, more preferably at least 22 bp, 23 bp, even more preferably at least 24 bp, 25 bp in length. The double-stranded section is preferably at most 60 bp, more preferably at most 50 bp, even more preferably at most 40 bp, most preferably at least 30 bp in length.

The oligonucleotide has preferably at least 2, 3, 4, 5, 6, more preferably at least 7, 8, 9, 10, 11, 12, even more preferably, at least 13, 14, 15, 16, 17, 18, most preferably, at least 19 ribonucleotides at the 5' end of the strand bearing the 5' triphosphate. In the most preferred embodiment, the fully double-stranded section is composed solely of ribonucleotides.

In one embodiment, the oligonucleotide is an RNA oligonucleotide. In another embodiment, the oligonucleotide is an RNA-DNA hybrid.

By "an essentially homogenous population", it is meant that the oligonucleotides contained in the preparation have essentially the same chemical identity (or chemical composition), including the same nucleotide sequence, backbone, modifications, length, and end structures. In other words, the oligonucleotides contained in the preparation are chemically defined and are essentially identical to each other. In particular, it is meant that at least 85%, preferably at least 90%, more preferably at least 95%, even more preferably at least 96%, 97%, 98%, most preferably at least 99% of the oligonucleotides in the preparation have the same chemical identity (or chemical composition), including the same nucleotide sequence, backbone, modifications, length, and end structures. In other words, the preparation is at least 85%, preferably at least 90%, more preferably at least 95%, even more preferably at least 96%, 97%, 98%, most preferably at least 99% pure. The purity and the chemical identity (or chemical composition) of an oligonucleotide preparation can be readily determined by a person skilled in the art using any appropriate methods, such as gel electrophoresis (in particular, denaturing gel electrophoresis), HPLC, mass spectrometry (e.g., MALDI-ToF MS), and sequencing.

In one embodiment, the oligonucleotide is a double-strand oligonucleotide.

As established in the art and used herein, "a double-strand oligonucleotide" refers to an oligonucleotide which is composed of two single strands of oligonucleotide.

Specifically, the double-strand oligonucleotide is one wherein at least one of the strands comprises at least 1, preferably at least 3, more preferably at least 6 ribonucleotide(s) at the 5' end, wherein at least one of the strands that comprise at least 1 ribonucleotide at the 5' end has a triphosphate attached to the most 5' ribonucleotide, wherein the triphosphate is free of any cap structure, wherein at least one of the ends that bear a 5' triphosphate is a blunt end, and wherein at least one of the blunt ends bearing a 5' triphosphate is followed by a fully double-stranded section which is at least 19, preferably at least 21 base pair (bp) in length.

In one embodiment, the double-strand oligonucleotide is fully double-stranded. In this case, the oligonucleotide is composed of two single-stranded oligonucleotides which have the same length and which have sequences that are 100% complementary to each other.

In one embodiment, the double-strand oligonucleotide is partially double-stranded. In this case, the two strands forming the oligonucleotide have different lengths, sequences which are not 100% complementary to each other, or both. In other words, the at least one fully double-stranded section of the oligonucleotide is connected with a single-stranded structure at one or both ends.

In one embodiment, the double-strand oligonucleotide has one blunt end bearing the 5' triphosphate and one 5' overhang of 1, 2, 3 or more nucleotide(s) at the other end which may or may not bear a 5' triphosphate. In another embodiment, the double-strand oligonucleotide has one blunt end bearing the 5' triphosphate and one 3' overhang of 1, 2, 3 or more nucleotide(s) at the other end which may or may not bear a 5' triphosphate. In yet another embodiment, the double-strand oligonucleotide has one blunt end bearing the 5' triphosphate and a second blunt end which may or may not bear a 5' triphosphate. In a further embodiment, the double-strand oligonucleotide has two blunt ends each bearing a 5' triphosphate. In certain embodiments, the 5' or 3' overhang has 3 or fewer, preferably 2 or fewer, nucleotides.

In one embodiment, the double-strand oligonucleotide has one 5' triphosphate. In another embodiment, the double-strand oligonucleotide has two 5' triphosphates. In a preferred embodiment, the second 5' triphosphate is also attached to a 5' ribonucleotide.

In a preferred embodiment, the double-strand oligonucleotide is fully double-stranded or partially double-stranded, comprising only one fully double-stranded section which is at least 19, preferably at least 21 bp in length. In a more preferred embodiment, the oligonucleotide is partially double-stranded and contains one 5' triphosphate attached to the most 5' ribonucleotide at the blunt end and a 3' overhang of 1 nt at the other end which is not blunt and does not bear a 5' triphosphate.

In the case of a fully double-stranded oligonucleotide or a partially double-stranded oligonucleotide comprising only one fully double-stranded section, the oligonucleotide is at least 19, preferably at least 21 bp in length, wherein the length refers to the number of base pairs of the continuous section of the oligonucleotide that is fully double-stranded. In other words, the length of the overhang is excluded from "the length of the double-strand oligonucleotide". By "continuous", it is meant that the section of the oligonucleotide that is fully double-stranded and is not interrupted by any single-stranded structures. Preferably, the double-strand oligonucleotide is at least 20, 21 bp, more preferably at least 22, 23 bp, and most preferably at least 24, 25 bp in length. Preferably, the double-strand oligonucleotide is at most 60 bp, more preferably at most 50 bp, even more preferably at most 40 bp, and most preferably at most 30 bp in length.

In one embodiment, the double-strand oligonucleotide is a homoduplex. By "homoduplex", it is meant that the two strands forming the oligonucleotide have exactly the same length and sequence in the 5' to 3' orientation. A homoduplex can be formed when each strand forming the double-strand oligonucleotide has a sequence that is 100% self-complementary, meaning that the sequence of the 5' half is 100% complementary to that of the 3' half.

Various methods for producing oligonucleotides are known in the art. However, in order to obtain an essentially homogeneous population of a double-strand oligonucleotide, chemical synthesis is the preferred method of preparation. The particular method or process of chemical synthesis is not important; it is only important that the synthesized oligonucleotide is purified and quality-controlled such that the oligonucleotide preparation contains essentially a homogenous population of oligonucleotides having essentially the same chemical identity (or chemical composition), including the same nucleotide sequence, backbone, modifications, length, and end structures. The oligonucleotides can be purified by any standard methods in the art, such as capillary gel electrophoresis and HPLC. Synthetic oligonucleotides, either single-strand or double-strand, obtained from most commercial sources contain 5' OH. These synthetic oligonucleotides can be modified at the 5' end to bear a 5' triphosphate by any appropriate methods known in the art. The preferred method for 5' triphosphate attachment is that developed by Janos Ludwig and Fritz Eckstein[27].

Alternatively, in vitro transcription can be employed. However, in order to obtain the single strands to prepare the a double-strand oligonucleotide by in vitro transcription, measures need to be taken to ensure that each in vitro transcribed single strand is indeed single-stranded and has the desired sequence. Aberrant transcripts may be generated in vitro using an RNA polymerase. For example, it is hypothesized that an RNA transcript generated by an RNA polymerase in vitro may fold back onto itself and prime RNA-dependent RNA synthesis, leading to the generation of aberrant transcripts of undefined and/or non-uniform lengths and sequences. Therefore, in principle, any measure that would prevent RNA synthesis primed by the RNA transcript itself can be employed.

For example, a single stranded oligonculeotide is designed to have a sequence $X_1$-$X_2$-$X_3$- ... $X_{m-2}$-$X_{m-1}$-$X_m$, wherein m is the length of the oligonucleotide, wherein the sequence has no or minimal self complementarity, wherein $X_1$, $X_2$, $X_3$, ..., $X_m$ are chosen from 1, 2 or 3 of the 4 conventional nucleotides A, U, C and G, wherein at least one of the nucleotides that are complementary to any of $X_{m-2}$, $X_{m-1}$, and $X_m$, i.e., $Y_{m-2}$, $Y_{m-1}$, and $Y_m$, is not among the 1, 2, or 3 nucleotides chosen for $X_1$, $X_2$, $X_3$, ..., $X_m$.

An appropriate DNA template for generating such an ssRNA oligonucleotide can be generated using any appropriate methods known in the art. An in vitro transcription reaction is set up using the DNA template and a nucleotide mixture which does not contain the complementary nucleotide(s) which is(are) not comprised in $X_1$-$X_2$-$X_3$- ... $X_{m-2}$-$X_{m-1}$-$X_m$. Any appropriate in vitro transcription conditions known in the art can be used. Due to the absence of the complementary nucleotide, no aberrant RNA-primed RNA synthesis can take place. As a result, a single-stranded population of $X_1$-$X_2$-$X_3$- ... -$X_m$ can be obtained. The resulting ssRNA preparation can be purified by any appropriate methods known in the art and an equal amount of two purified ssRNA preparations with complementary sequence can be annealed to obtain an essentially homogenous population of a double-strand RNA oligonucleotide of desired sequence.

For example, the ssRNA oligonucleotide may be GACACACACACACACACACACA (SEQ ID NO: 44) and the in vitro transcription may be carried out in the presence of ATP, CTP and GTP, i.e., in the absence of UTP.

It is also possible to synthesize the two strands forming the double-strand oligonucleotide using different methods. For example, one strand can be prepared by chemical synthesis and the other by in vitro transcription. Furthermore, if desired, an in vitro transcribed ssRNA can be treated with a phosphatase, such as calf intestine phosphotase (CIP), to remove the 5' triphosphate.

In another embodiment, the oligonucleotide is a single-strand oligonucleotide having a stem-and-loop structure. As established in the art and used herein, "a single-strand oligonucleotide" refers to an oligonucleotide which is composed of one single strand of oligonucleotide. As established in the art and used herein, a stem-and-loop structure contains a stem, which is a fully double-stranded section made up of two stretches of nucleic acids which have complementary sequences and the same length, and a loop which is a single-stranded section.

Specifically, the single-strand oligonucleotide has a triphosphate at the 5' end and contains at least one stem-and-loop structure, wherein the stem of at least one of the stem-and-loop structures is composed of the 5' and the 3' end of the single-strand oligonucleotide, is fully double-stranded (i.e., not interrupted by any single-stranded structures), and is at least 19 bp, preferably at least 21 bp in length, and wherein the end of the stem which is formed by the very 5' and 3' ends of the oligonucleotide and which is not connect to the loop is blunt. In other words, at least 19, preferably at least 21 nucleotides at the very 5' end and at least 21 nucleotides at the very 3' end of the oligonucleotide have 100% complementarity.

The stem bearing the 5' triphosphate and the blunt end is preferably at least 20, 21 bp, more preferably at least 22, 23 bp, and most preferably at least 24, 25 bp in length. The stem is preferably at most 60 bp, more preferably at most 50 bp, even more preferably at most 40 bp, and most preferably at most 30 bp in length.

The exact size and the sequence of the loop is not critical; it is only critical that the loop does not adversely affect the formation and the stability of the stem and does not interfere (e.g., sterically hinder) the interaction between the blunt end and the 5' triphosphate with RIG-I. The formation of a stem-and-loop structure can be readily predicted by a person skilled in the art on the basis of the nucleotide sequence of the oligonucleotide and experimentally verified by methods known in the art. For example, a ssRNA oligonculeotide can be digested with a single-strand-specific RNase and analysed on a denaturing gel. Binding between an oligonucleotide and RIG-I can be readily determined using any appropriate methods known in the art, such as immunoprecipitation[15], fluorescence anisotropy measurement[26], and gel shift assay[24].

In one embodiment, the single-strand oligonucleotide contains only one stem-and-loop structure.

The single-strand oligonucleotide preparation can be obtained by chemically synthesis or in vitro transcription. The particular method or process of preparation is not important; it is only important that the oligonucleotide can be purified and quality-controlled such that the oligonucleotide preparation contains essentially a homogenous population of oligonucleotides having essentially the same chemical identity (or chemical composition), including the same nucleotide sequence, backbone, modifications, length, and end structures. If the oligonucleotide is chemically synthesized and bears a 5' OH, a 5' triphosphate can be added by any appropriate methods known in the art, preferably the method developed by Janos Ludwig and Fritz Eckstein[27].

Without being bound by any theory, it is hypothesized that when the 5' and the 3' nucleotides of a single-strand oligonucleotide have 100% complementarity and the stem has a blunt end, single-strand RNA oligonucleotides having a stem-and-loop (or hairpin) structure and a blunt end with defined sequence, length and end structure can be faithfully obtained by in vitro transcription because of the absence of aberrant RNA-primed, RNA-dependent transcription.

Even though as defined above, the at least one fully double-stranded section which is at least 19, preferably at least 21 bp in length, which has a blunt end and which bears a 5' triphosphate at the blunt end is continuously fully double-stranded, i.e., not interrupted by any single-stranded structure, this does not have to be the case for an oligonucleotide which is capable of activating RIG-I and inducing an anti-viral response, in particular, a type I IFN response, more specifically, an IFN-α response. One or more mismatch(es) may be tolerated in the two stretches of nucleic acids which form the double-stranded section in that the IFN-inducing activity of the oligonucleotide is not significantly reduced. In other words, the "fully" double-stranded section may be discontinuous, i.e., interrupted by one or more single-stranded (or loop) structure(s). An oligonucleotide preparation which comprises an essentially homogenous population of such an oligonucleotide is also encompassed by the present invention.

The single-stranded (or loops) structure may occur in one or both of the two stretches of nucleic acids which form the double-stranded section.

Preferably, the "fully" double-stranded section is interrupted by at most 3, more preferably at most 2, even more preferably at most 1 single-stranded (or loop) structure(s).

The loops which occur in one or both of the two stretches of nucleic acids which form the double-stranded section may have the same or different length. Preferably, the loop is at most 8, 7 nucleotides (nt), more preferably at most 6, 5 nt, even more preferably at most 4, 3 nt, most preferably at most 2, 1 nt in length. The length of the loop refers to the number of nucleotides in one stretch of nucleic acid which are between two adjacent fully stranded-structures and which do not base pair with nucleotides on the other stretch of nucleic acid.

The mismatch is preferably at least 3, 4, 5, 6 bp, more preferably at least 7, 8, 9, 10, 11, 12 bp, even more preferably at least 13, 14, 15, 16, 17, 18 bp away from the blunt end bearing the 5' triphosphate. The distance between a mismatch and the blunt end refers to the number of nucleotides between the blunt end and the first nucleotide which does not form a base pair and which is closest to the blunt end.

Figure 16:
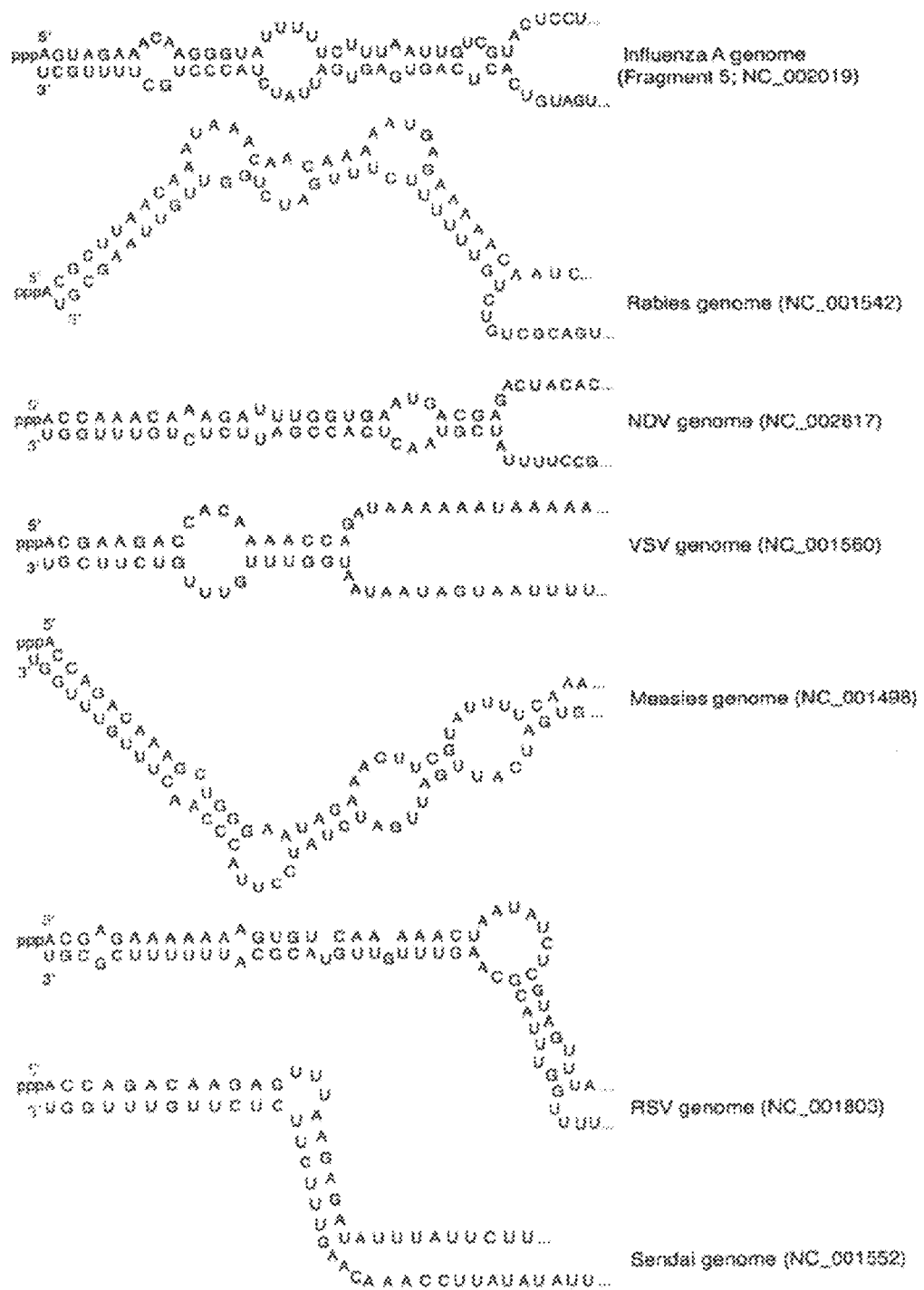
FIG. 16. Panhandle configuration of negative strand RNA viruses. In silico hybridizations[3] of the 5' and the 3' end of different negative strand RNA viruses. The 5' nucleoside is adenosin.

Reference is made to FIG. 16 to illustrate the above terms. In the case of the Sendai viral genome, the double-stranded structure formed by the 5' and 3' ends of the genomic RNA is interrupted by a loop of 3 nt (5'-UUU-3') in the stretch of nucleic acid at the 5' end and not interrupted by any loop structure in the stretch of nucleic acid at the 3' end. In the case of the Rabies viral genome, the double-stranded structure formed by the 5' and 3' ends of the genomic RNA is interrupted by a loop of 5 nt (5'-AUAAA-3'), followed by a loop of 1 nt (A) followed by a loop of 5 nt (5'-AAUGA-3') in the stretch of nucleic acid at the 5' end, and interrupted by a loop of 1 nt (G) and a loop of 3 nt (3'-CUA-5') and a loop of 1 nt (C)) in the stretch of nucleic acid at the 3' end.

In one embodiment, the double- or single-strand RNA oligonucleotide contains one or more GU wobble base pair(s) instead of GC or UA base pairing.

In a preferred embodiment, the double- or single-strand oligonucleotide comprises at least 1, 2, 3, 4, 5, preferably at least 6, 7, 8, 9, 10, more preferably at least 11, 12, 13, 14, 15, even more preferably at least 16, 17, 18, 19, 20 inosine (I). In another preferred embodiment, at least 1, 2, 3, 4, 5%, preferably at least 10, 15, 20, 25, 30%, more preferably at least 35, 40, 45, 50, 55, 60%, even more preferably at least 70, 80, or 90% of the adenosine (A) and/or guanosine (G) in the oligonucleotide is replaced with inosine (I).

The 5' ribonucleotide bearing the at least one 5' triphosphate is preferably A, followed by G, followed by U, followed by C, in the order of descending preference.

In preferred embodiments, the sequence of the first 4 ribonucleotides at the 5' end of the double- or single-strand oligonucleotide bearing the 5' triphosphate is selected from: AAGU (No. 1), AAAG (No. 2), AUGG (No. 3), AUUA (No. 4), AACG (No. 5), AUGA (No. 6), AGUU (No. 7), AUUG (No. 8), AACA (No. 9), AGAA (No. 10), AGCA (No. 11), AACU (No. 12), AUCG (No. 13), AGGA (No. 14), AUCA (No. 15), AUGC (No. 16), AGUA (No. 17), AAGC (No. 18), AACC (No. 19), AGGU (No. 20), AAAC (No. 21), AUGU (No. 22), ACUG (No. 23), ACGA (No. 24), ACAG (No. 25), AAGG (No. 26), ACAU (No. 27), ACGC (No. 28), AAAU (No. 29), ACGG (No. 30), AUUC (No. 31), AGUG (No. 32), ACAA (No. 33), AUCC (No. 34), AGUC (No. 35), wherein the sequence is in the 5'→3' direction. In more preferred embodiments, the sequence of the first 4 ribonucleotides at the 5' end of the oligonucleotide bearing the 5' triphosphate is selected from Nos. 1-19, more preferably from Nos. 1-9, even more preferably from Nos. 1-4. In certain embodiments, the first nucleotide of the above-listed 5' 4-nucleotide sequences is a G, U or C, in the order of descending preference, instead of A.

In certain embodiments, the double- or single-strand oligonucleotide contains one or more structural motif(s) or molecular signature(s) which is(are) recognized by the TLRs, in particular, TLR3, TLR7 and TLR8.

In one embodiment, the double-strand oligonucleotide or a stem of the single-strand oligonucleotide is at least 30 bp in length and is recognized by TLR3[2].

In another embodiment, the double-strand oligonucleotide or a stem of the single-strand oligonucleotide contains defined sequence motifs recognized by TLR7[3, 4, 5, 22, 29]. In one preferred embodiment, the double-strand oligonucleotide or a stem of the single-strand oligonucleotide comprises at least one, preferably at least two, more preferably at least three, even more preferably at least four, even more preferably at least five, and most preferably at least six, of the 4-nucleotide (4mer) motifs selected from the group consisting of:

GUUC (No. 101), GUCA (No. 102), GCUC (No. 103), GUUG (No. 104), GUUU (No. 105), GGUU (No. 106), GUGU (No. 107), GGUC (No. 108), GUCU (No. 109), GUCC (No. 110), GCUU (No. 111), UUGU (No. 112), UGUC (No. 113), CUGU (No. 114), CGUC (No. 115), UGUU (No. 116), GUUA (No. 117), UGUA (No. 118), UUUC (No. 119), UGUG (No. 120), GGUA (No. 121), GUCG (No. 122), UUUG (No. 123), UGGU (No. 124), GUGG (No. 125), GUGC (No. 126), GUAC (No. 127), GUAU (No. 128), UAGU (No. 129), GUAG (No. 130), UUCA (No. 131), UUGG (No. 132), UCUC (No. 133), CAGU (No. 134), UUCG (No. 135), CUUC (No. 136), GAGU (No. 137), GGUG (No. 138), UUGC (No. 139), UUUU (No. 140), CUCA (No. 141), UCGU (No. 142), UUCU (No. 143), UGGC (No. 144), CGUU (No. 145), CUUG (No. 146), UUAC (No. 147),
wherein the nucleotide sequences of the motifs are 5'→3'.

Preferably, the 4mer motifs are selected from the group consisting of Nos. 101-119, Nos. 101-118, Nos. 101-117, Nos. 101-116, more preferably, Nos. 101-115, Nos. 101-114, Nos. 101-113, Nos. 101-112, more preferably, Nos. 101-111, Nos. 110-110, Nos. 101-109, No. 101-108, Nos. 101-107, even more preferably, Nos. 101-106, Nos. 101-105, Nos. 101-104, Nos. 101-103, most preferably, Nos. 101-102 of the 4mer motifs. The oligonucleotide may comprise one or more copies of the same 4mer motif or one or more copies of one or more different 4mer motifs.

In yet another embodiment, the double-strand oligonucleotide has one blunt end which bears a 5' triphosphate and one end with a 5' or 3' overhang, wherein the 5' or 3' overhang contains defined sequence motifs recognized by TLR8[4, 18, 22, 28]. In a further embodiment, a loop of the single-strand oligonucleotide contains defined sequence motifs recognized by TLR8. In certain embodiments, the 5' or 3' overhang of the double-strand oligonucleotide or the loop of the single-stranded oligonucleotide is at least 4, preferably at least 6, more preferably at least 12, most preferably at least 18 nucleotides in length. In preferred embodiments, the 5' or 3' overhang of the double-strand oligonucleotide or the loop of the single-strand oligonucleotide comprises at least one, preferably at least two, more preferably at least three, even more preferably at least four, even more preferably at least five, and most preferably at least six, of the 4-nucleotide (4mer) motifs selected from the group consisting of:

UCGU (No: 201), GUUG (No. 202), UGGU (No. 203), UGGC (No. 204), GGUA (No. 205), UGAU (No. 206), UGCU (No. 207), UUGC (No. 208), UUGU (No. 209), UAGU (No. 210), GGUU (No. 211), GUUU (No. 212), UGUG (No. 213), GUGU (No. 214), UGCC (No. 215), GUAU (No. 216), GUGC (No. 217), UGUA (No. 218), UGUC (No. 219), CUGU (No. 220), UGAC (No. 221), UGUU (No. 222), UAAU (No. 223), GUAG (No. 224), UCUU (No. 225), UUGG (No. 226), UUUG (No. 227), GGAU (No. 228), UUUU (No. 229), CGUU (No. 230), UUAU (No. 231), GUUC (No. 232), GUGG (No. 233), GGUG (No. 234), UAUU (No. 235), UCUG (No. 236), GUAC (No. 237), UAGG (No. 238), UCUC (No. 239), UAGC (No. 240), UAUC (No. 241), CUAU (No. 242), UACU (No. 243), CGGU (No. 244), UGCG (No. 245), UUUC (No. 246), UAUG (No. 247), UAAG (No. 248), UACC (No. 249), UUAG (No. 250), GCUU (No. 251), CAGU (No. 252), UGAG (No. 253), GAUU (No. 254), GAGU (No. 255), GUUA (No. 256), UGCA (No. 257), UUCU (No. 258), GCCU (No. 259), GGUC (No. 260), GGCU (No. 261), UUAC (No. 262), UCAU (No. 263), GCGU (No. 264), GCAU (No. 265), GAUG (No. 266), GUCU (No. 267), CGUA (No. 268), CGAU (No. 269), wherein the nucleotide sequences of the motifs are 5'→3', Preferably, the 4mer motifs are selected from the group consisting of Nos. 201-211, more preferably Nos. 201-210, Nos. 201-209, Nos. 201-208, even more preferably Nos. 201-207, Nos. 201-206, Nos. 201-205, Nos. 201-204, even more preferably Nos. 201-203, Nos. 201-202 of the above-listed 4mer motifs. Most preferably, the 4mer motif is UCGU (No. 201). The oligonucleotide may comprise one or more copies of the same 4mer motif or one or more copies of one or more different 4mer motifs.

In a further embodiment, the double-strand oligonucleotide has one blunt end which bears a 5' triphosphate and one end with a 5' or 3' overhang, wherein the 5' or 3' overhang is composed of deoxyribonucleotides and contains defined sequence motifs recognized by TLR9[6]. In another embodiment, a loop of the single-strand oligonucleotide is composed of deoxyribonucleotides and contains defined sequence motifs recognized by TLR9. In preferred embodiments, the 5' or 3' overhang of the double-strand oligonucleotide or the loop of the single-strand oligonucleotide comprises one or more unmethylated CpG dinucleotides.

The double- or single-strand oligonucleotide may contains one or more of the same or different structural motif(s) or molecular signature(s) recognized by TLR3, TLR7, TLR8 and TLR9 described above.

The double- or single-strand oligonucleotide may contain any naturally-occurring, synthetic, modified nucleotides, or a mixture thereof, as long as the synthetic and/or modified nucleotides do not compromise (i.e., reduce) the type I IFN-inducing activity of the oligonucleotide.

In one embodiment, the oligonucleotide does not contain any modification such as pseudouridine, 2-thiouridine, 2'-Fluorine-dNTP, in particular 2'-fluorine-dCTP, 2'-fluorine-dUTP.

In another embodiment, the nucleotides of the oligonucleotide, except the most 3' nucleotide(s) which base pairs with the most 5' ribonucleotide(s) bearing the 5' tripshosphate(s), is(are) free of 2'-O-methylation.

In a preferred embodiment, at least one most 3' nucleotide which base pairs with a most 5' ribonucleotide bearing a 5' triphosphate at the blunt end is 2'-O-methylated. More preferably, said most 3' nucleotide is 2'-O-methylated UTP.

In one embodiment, the oligonucleotide is a single-strand oligonucleotide and contains one 3' end and thus one most 3' nucleotide. In one embodiment, the oligonucleotide is a double-strand oligonucleotide and contains two 3' ends. In one embodiment, the double-strand oligonucleotide contains one 5' triphosphate at one blunt end, and the most 3' nucleotide which base pairs with the most 5' ribonucleotide bearing a 5' triphosphate at the blunt end is 2'-O-methylated. In one embodiment, the double-strand oligonucleotide contains two 5' triphosphates at two blunt ends, and one, preferably both of the most 3' nucleotides at the two blunt ends is/are 2'-O-methylated.

The double- or single-strand oligonucleotide may contain any naturally-occurring, synthetic, modified internucleoside linkages, or a mixture thereof, as long as the linkages do not compromise the type I IFN-inducing activity of the oligonucleotide. In one embodiment, the oligonucleotide comprises at least one phosphorothioate linkage and/or at least one pyrophosphate linkage.

The 5' triphosphate group of the double- or single-strand oligonucleotide may be modified as long as the modification does not compromise the type I IFN-inducing activity of the oligonucleotide. For example, one or more of the oxygen (O) in the triphosphate group may be replaced with a sulfur (S); the triphosphate group may be modified with the addition of one or more phosphate group(s).

The double- or single-strand oligonucleotide may be modified covalently or non-covalently to improve its chemical stability, resistance to nuclease degradation, ability to across cellular and/or subcellular membranes, target (organ, tissue, cell type, subcellular compartment)-specificity, pharmacokinetic properties, biodistribution, or any combinations thereof. For example, phosphorothioate linkage(s) and/or pyrophosphate linkage(s) may be introduced to enhance the chemical stability and/or the nuclease resistance of an RNA oligonucleotide. In another example, the oligonucleotide may be covalently linked to one or more lipophilic group(s) or molecule(s), such as a lipid or a lipid-based molecule, preferably, a cholesterol or a derivative thereof. The lipophilic group or molecule is preferably not attached to the blunt end bearing the 5' triphosphate. Preferably, the modification does not comprise the type I IFN-inducing activity of the oligonucleotide. Alternatively, a reduction in the type I IFN-inducing activity of the oligonucleotide caused by the modification is off-set by an increase in the stability and/or delivery and/or other properties as described above.

The double- or single-strand oligonucleotide may bear any combination of any number of features described above. A preferred double-strand oligonucleotide is an RNA oligonucleotide having one blunt end with one 5' triphosphate attached to a 5' A and a length of between 21 and 30 bp. A more preferred double-strand oligonucleotide is an RNA oligonucleotide having one blunt end bearing one 5' triphosphate attached to a 5' A, a 5' overhang of 1 or 2 nt at the other end which does not bear a 5' triphosphate, and a length of between 21 and 30 bp. A preferred single-strand oligonucleotide has one stem-and-loop structure with a stem that is between 21 and 30 bp in length. Even more preferably, at least one most 3' ribonucleotide which base pairs with the most 5' ribonucleotide(s) bearing the 5' triphosphate(s) at the blunt end(s) is 2'-O-methylated in the above-mentioned oligonucleotides.

In the second aspect, the present invention provides an oligonucleotide preparation which comprises an essentially homogenous population of a single-strand oligonucleotide, wherein the oligonucleotide has a nucleotide sequence which is 100% complementary to at least 19, preferably at least 21 nucleotides at the very 5' end of the genomic RNA of a negative single-strand RNA virus.

Preferably, the oligonucleotide has a nucleotide sequence which is 100% complementary to at least 20, 21, preferably 22, 23, more preferably 24, 25 nucleotides at the very 5' end of the genomic RNA of the negative single-strand RNA virus.

Negative single-strand RNA viruses include, but are not limited to, influenza A virus, Rabies virus, Newcastle disease virus (NDV), vesicular stomatitis virus (VSV), Measles virus, mumps virus, respiratory syncytial virus (RSV), Sendai virus, Ebola virus, and Hantavirus.

Without being bound by any theory, such a single-strand oligonucleotide forms a fully double-stranded structure with a blunt end with the 5' end of the viral genomic RNA which bears a 5' triphosphate, thereby providing a more potent RIG-I ligand than the partially double-stranded structure comprising stem-and-loop structures formed by the 5' and 3' end of the viral genomic RNA.

The oligonucleotide preparation of the invention can be used, either alone or in combination with one or more immunostimulatory agent(s) to induce an anti-viral response, in particular, an type I IFN, more specifically, an IFN-α response, against a negative single strand RNA virus in a virus-specific manner. The oligonucleotide preparation of the invention can be used, either alone or in combination with one or more immunostimulatory agent(s) and/or anti-viral agent(s) to prevent and/or treat a viral infection, in particular, an infection by a negative single-strand RNA virus.

In the third aspect, the present invention provides an oligonucleotide preparation which comprises an essentially homogenous population of a single-strand oligonucleotide, wherein the oligonucleotide has a nucleotide sequence which is 100% complementary to the nucleotide sequence at the 5' end of the genomic RNA of a negative single-strand RNA virus between nucleotides 2+m and 2+m+n, wherein m and n are independently positive integers, wherein m equals to or is greater than 1 and is less than or equals to 5, and wherein n equals to or is greater than 12, preferably 13, 14, 15, more preferably 16, 17, 18, even more preferably 19, 20, 21.

Preferably, n equals to or is greater than 20, 21, more preferably 22, 23, even more preferably 24, 25. Preferably, n is less than or equals to 60, 50, more preferably 40, even more preferably, 30.

Without being bound by any theory, such a single-strand oligonucleotide forms a fully double-stranded structure with a 5' overhang of 2-6 nt with the 5' end of the viral genomic RNA which bears a 5' triphosphate, thereby providing an inactive RIG-I ligand. Since the oligonucleotide has a higher degree of complemetarity to the 5' end of the genomic viral RNA than the 3' end of the genomic viral RNA, it displaces the 3' end of the genomic viral RNA in the double-stranded structure formed between the 5' and the 3' ends of the genomic viral RNA, thereby converting an active RIG-I ligand into an inactive RIG-I ligand.

The oligonucleotide preparation of the present invention can be used, either alone or in combination with one or more immunosuppressant, to reduce or even abolish an anti-viral response, in particular, a type I IFN, more specifically, an IFN-α response, against a negative single-strand RNA virus in a virus-specific manner to prevent and/or inhibit (i.e., reduce and/or eliminate) detrimental effects caused by the over-production of type I IFN and/or other components of the anti-viral response.

siRNA Oligonucleotides

In another embodiment, the invention features a short interfering 5'-3p-oligonucleotide (3p-siRNA) that down-regulates the expression of a target gene or that directs cleavage of a target RNA, comprising a sense region and an antisense region, wherein the antisense region comprises a nucleotide sequence that is complementary to a nucleotide sequence of RNA encoded by the target gene or a portion thereof and the sense region comprises a nucleotide sequence that is complementary to the antisense region.

By "complementarity" is meant that a nucleic acid can form hydrogen bond(s) with another nucleic acid sequence by either traditional Watson-Crick including G-U-wobble base pairing or other non-traditional types as described herein. In one embodiment, a double stranded nucleic acid molecule of the invention, such as an siRNA molecule, where one strand comprises nucleotide sequence that is referred to as the sense region and the other strand comprises a nucleotide sequence that is referred to as the antisense region, wherein each strand is between 15 and 30 nucleotides in length, comprises between about 10% and about 100% (e.g., about 10%, 20%, 30%, 40%, 50%, 60%, 70%, 80%, 90%, or 100%) complementarity between the sense region and the antisense region of the double stranded nucleic acid molecule. In reference to the nucleic oligonucleotides of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al., 1987, CSH Symp. Quant. Biol. LII pp. 123-133; Frier et al., 1986, Proc. Nat. Acad. Sci. USA 83:9373-9377; Turner et al., 1987, J. Am. Chem. Soc. 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary respectively). In one embodiment, a siRNA molecule of the invention has perfect complementarity between the sense strand or sense region and the antisense strand or antisense region of the siRNA oligonucleotide. In one embodiment, a siRNA oligonucleotide of the invention is perfectly complementary to a corresponding target nucleic acid molecule. "Perfectly complementary" means that all the contiguous residues of a nucleic acid sequence will hydrogen bond with the same number of contiguous residues in a second nucleic acid sequence. In one embodiment, a siRNA oligonucleotide of the invention comprises about 15 to about 30 or more (e.g., about 15, 16, 17, 18, 19, 20, 21, 22, 23, 24, 25, 26, 27, 28, 29, or 0.30 or more) nucleotides that are complementary to one or more target nucleic acid molecules or a portion thereof. In one embodiment, a siRNA molecule of the invention has partial complementarity (i.e., less than 100% complementarity) between the sense strand or sense region and the antisense strand or antisense region of the siRNA oligonucleotide or between the antisense strand or antisense region of the siRNA oligonucleotide and a corresponding target nucleic acid molecule. For example, partial complementarity can include various mismatches or non-based paired nucleotides (e.g., 1, 2, 3, 4, 5 or more mismatches or non-based paired nucleotides) within the siRNA structure which can result in bulges, loops, or overhangs that result between the between the sense strand or sense region and the antisense strand or antisense region of the siRNA molecule or between the antisense strand or antisense region of the siRNA oligonucleotide and a corresponding target nucleic acid molecule.

In certain embodiments, the double- or single-strand oligonucleotide described above has gene-silencing activity. As used herein, the term "gene-silencing activity" refers to the capability of the oligonucleotide to downregulate the expression of a gene, preferably via RNA interference (RNAi). In a preferred embodiment, the oligonucleotide is an siRNA (small interfering RNA) or an shRNA (small hairpin RNA).

In certain embodiments, the double- or single-strand oligonucleotide described above has apoptose-inducing activity. As used herein, the term "apoptose inducing activity" refers to the capability of the oligonucleotide to induce programmed cell-death, preferably via activation of RIG-I in tumor cells, preferably via RNA interference (RNAi) in tumor cells, preferably via type-I IFN pathway in tumor cells or in other cells such as immune cells indirectly contributing to apoptosis induction via the type I IFN receptor expressed in tumor cells. In a preferred embodiment, the oligonucleotide is an siRNA (short interfering RNA) or an shRNA (short hairpin RNA).

In one embodiment, the invention features an (3p-siRNA) oligonucleotide that inhibits, downregulates, or reduces the expression of a target gene or that directs cleavage of a target RNA, for example, wherein the target gene or RNA comprises protein encoding sequence. In one embodiment, the invention features a 3p-siRNA oligonucleotide that downregulates expression of a target gene or that directs cleavage of a target RNA, for example, wherein the target gene or RNA comprises non-coding sequence or regulatory elements involved in target gene expression (e.g., non-coding RNA, miRNA, stRNA etc.). In any of the embodiments herein, the 3p-siRNA oligonucleotide of the invention modulates expression of one or more targets via RNA interference or the inhibition of RNA interference. The RNA interference can be RISC-mediated cleavage of the target (e.g., siRNA-mediated RNA interference). The RNA interference can be translational inhibition of the target (e.g., miRNA-mediated RNA interference). In a preferred embodiment, the RNA interference is transcriptional inhibition of the target (e.g., siRNA-mediated transcriptional silencing). The RNA interference generally takes place in the cytoplasm. In one embodiment, the RNA interference can also take place in the nucleus.

In a particularyl preferred embodiment the siRNA oligonucleotied has a "combined activity". As used herein the term "combined activity" refers to the capability of an oligonucleotide to activate RIG-I and to have gene-silencing activity. In other words "combined activity" refers to an oligonucleotide which is both a) capable of activating RIG-I and/or inducing an anti-viral, in particular, an IFN, response in cells expressing RIG-I and b) downregulating expression of a target gene. The term "combined" means that the same oligonucleotide exhibits the combined activities.

In one embodiment, a siRNA oligonucleotide of the invention comprises modified nucleotides while maintaining the ability to mediate RNAi. The modified nucleotides can be used to improve in vitro or in vivo characteristics such as stability, activity, toxicity, immune response, and/or bioavailability. For example, a siRNA oligonucleotide of the invention can comprise modified nucleotides as a percentage of the total number of nucleotides present in the siRNA oligonucleotide. As such, a siRNA oligonucleotide of the invention can generally comprise about 5% to about 100% modified nucleotides (e.g., about 5%, 10%, 15%, 20%, 25%, 30%, 35%, 40%, 45%, 50%, 55%, 60%, 65%, 70%, 75%, 80%, 85%, 90%, 95% or 100% modified nucleotides). For example, in one embodiment, between about 5% to about 100% (e.g., about 5%, 10%, 15%, 20%, 25%, 30%, 35%, 40%, 45%, 50%, 55%, 60%, 65%, 70%, 75%, 80%, 85%, 90%, 95% or 100% modified nucleotides) of the nucleotide positions in a siRNA oligonucleotide of the invention comprise a nucleic acid sugar modification, such as a 2'-sugar modification, e.g., 2'-O-methyl nucleotides, 2'-deoxy-2'-fluoro nucleotides, 2'-deoxy-2'-fluoroarabino, 2'-O-methoxyethyl nucleotides, 2'-O-trifluoromethyl nucleotides, 2'-O-ethyl-trifluoromethoxy nucleotides, 2'-O-difluoromethoxy-ethoxy nucleotides, or 2'-deoxy nucleotides. In another embodiment, between about 5% to about 100% (e.g., about 5%, 10%, 15%, 20%, 25%, 30%, 35%, 40%, 45%, 50%, 55%, 60%, 65%, 70%, 75%, 80%, 85%, 90%, 95% or 100% modified nucleotides) of the nucleotide positions in a siRNA oligonucleotide of the invention comprise a nucleic acid base modification, such as inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), or propyne modifications. In another embodiment, between about 5% to about 100% (e.g., about 5%, 10%, 15%, 20%, 25%, 30%, 35%, 40%, 45%, 50%, 55%, 60%, 65%, 70%, 75%, 80%, 85%, 90%, 95% or 100% modified nucleotides) of the nucleotide positions in a siRNA oligonucleotide of the invention comprise a nucleic acid backbone modification. In another embodiment, between about 5% to about 100% (e.g., about 5%, 10%, 15%, 20%, 25%, 30%, 35%, 40%, 45%, 50%, 55%, 60%, 65%, 70%, 75%, 80%, 85%, 90%, 95% or 100% modified nucleotides) of the nucleotide positions in a siRNA oligonucleotide of the invention comprise a nucleic acid sugar, base, or backbone modification or any combination thereof (e.g., any combination of nucleic acid sugar, base, backbone or non-nucleotide modifications). In one embodiment, a siRNA oligonucleotide of the invention comprises at least about 20%, 25%, 30%, 35%, 40%, 45%, 50%, 55%, 60%, 65%, 70%, 75%, 80%, 85%, 90%, 95% or 100% modified nucleotides. The actual percentage of modified nucleotides present in a given siRNA oligonucleotide will depend on the total number of nucleotides present in the siRNA oligonucleotide. If the siRNA oligonucleotide is single stranded, the percent modification can be based upon the total number of nucleotides present in the single stranded siRNA oligonucleotides. Likewise, if the siRNA oligonucleotide is double stranded, the percent modification can be based upon the total number of nucleotides present in the sense strand, antisense strand, or both the sense and antisense strands.

In one embodiment, the invention features a method of modulating the expression of a target gene in a subject or organism comprising: (a) synthesizing a siRNA oligonucleotide of the invention, which can be chemically-modified, wherein one of the siRNA strands comprises a sequence complementary to RNA of the target gene; and (b) introducing the siRNA oligonucleotide into the subject or organism under conditions suitable to modulate (e.g., inhibit) the expression of the target gene in the subject or organism.

In one embodiment, the invention features a method of modulating the expression of a target gene within a cell, comprising: (a) synthesizing a siRNA oligonucleotide of the invention, which can be chemically-modified, wherein the siRNA comprises a single stranded sequence having complementarity to RNA of the target gene; and (b) introducing the siRNA oligonucleotide into a cell under conditions suitable to modulate (e.g., inhibit) the expression of the target gene in the cell.

"Modulation" means, in the context of the invention the inhibition, down-regulation, or reduction of the expression of a target gene. By "inhibit", "down-regulate", or "reduce", it is meant that the expression of the gene, or level of RNA molecules or equivalent RNA molecules encoding one or more proteins or protein subunits, or activity of one or more proteins or protein subunits, is reduced below that observed in the absence of the nucleic acid molecules (e.g., siRNA) of the invention. In one embodiment, inhibition, down-regulation or reduction with an siRNA oligonucleotide is below that level observed in the presence of an inactive or attenuated molecule. In another embodiment, inhibition, down-regulation, or reduction with siRNA oligonucleotides is below that level observed in the presence of, for example, an siRNA oligonucleotide with scrambled sequence or with mismatches. In another embodiment, inhibition, down-regulation, or reduction of gene expression with a nucleic acid molecule of the instant invention is greater in the presence of the nucleic acid molecule than in its absence. In one embodiment, inhibition, down regulation, or reduction of gene expression is associated with post transcriptional silencing, such as RNAi mediated cleavage of a target nucleic acid molecule (e.g. RNA) or inhibition of translation.

By "gene", or "target gene" or "target DNA", is meant a nucleic acid that encodes an RNA, for example, nucleic acid sequences including, but not limited to, structural genes encoding a polypeptide. By "target nucleic acid" or "target polynucleotide" is meant any nucleic acid sequence (e.g, any target and/or pathway target sequence) whose expression or activity is to be modulated. The target nucleic acid can be DNA or RNA. In one embodiment, a target nucleic acid of the invention is target RNA or DNA.

Given the coding sequence of a gene, a person skilled in the art can readily design siRNAs and shRNAs using publicly available algorithms such as that disclosed in Reynolds et al.[23] and design engines such as "BD-RNAi design" (Beckton Dickinson) and "Block-iT RNAi" (Invitrogen). Even though conventional siRNAs usually are 19 bp in length and have two 2-nucleotide 3' overhangs (i.e., each single strand is 21 nucleotides in length), a person skilled in the art can readily modify the sequence of the siRNAs designed by the known algorithms or design engines and obtain double-strand oligonucleotides which have the structural characteristics of those described above. Furthermore, a person skilled in the art can readily modify the sequence of shRNA designed to obtain single-strand oligonucleotides which have the structural characteristics of those described above. Moreover, a person skilled in the art can readily test the gene-silencing efficacy of the oligonucleotides using methods known in the art such as Northern blot analysis, quantitative or semi-quantitative RT-PCR, Western blot analysis, surface or intracellular FACS analysis. One exemplary method for designing siRNA oligonucleotides is outlined below.

The following non-limiting steps can be used to carry out the selection of siNAs targeting a given gene sequence or transcript.

1. The target sequence is parsed in silico into a list of all fragments or subsequences of a particular length, for example 23 nucleotide fragments, contained within the target sequence. This step is typically carried out using commercial sequence analysis programs such as Oligo, MacVector, or the GCG Wisconsin Package.

2. In some instances the siRNAs may correspond to more than one target sequence; such would be the case for example in targeting different transcripts of the same gene, targeting different transcripts of more than one gene, or for targeting both the human gene and an animal homolog. In this case, a subsequence list of a particular length is generated for each of the targets, and then the lists are compared to find matching sequences in each list. The subsequences are then ranked according to the number of target sequences that contain the given subsequence in order to find subsequences that are present in most or all of the target sequences. Alternately, the ranking can identify subsequences that are unique to a target sequence, such as a mutant target sequence. Such an approach would enable the use of siRNA to target specifically the mutant sequence and not effect the expression of the normal sequence.

3. In some instances the siRNA subsequences are absent in one or more sequences while present in the desired target sequence; such would be the case if the siRNA targets a gene with a paralogous family member that is to remain untargeted. As in paragraph 2 above, a subsequence list of a particular length is generated for each of the targets, and then the lists are compared to find sequences that are present in the target gene but are absent in the untargeted paralog.

4. The ranked siRNA subsequences can be further analyzed and ranked according to GC content. A preference can be given to sites containing 30-70% GC, with a further preference to sites containing 40-60% GC.

5. The ranked siRNA subsequences can be further analyzed and ranked according to self-folding and internal hairpins. Weaker internal folds are preferred; strong hairpin structures are to be avoided.

6. The ranked siRNA subsequences can be further analyzed and ranked according to whether they have runs of GGG or CCC in the sequence. GGG (or even more Gs) in either strand can make oligonucleotide synthesis problematic and can potentially interfere with RNAi activity, so it is avoided whenever better sequences are available. CCC is searched in the target strand because that will place GGG in the antisense strand.

7. The ranked siRNA subsequences can be further analyzed and ranked according to whether they have the dinucleotide UU (uridine dinucleotide) on the 3'-end of the sequence, and/or AA on the 5'-end of the sequence (to yield 3' UU on the antisense sequence). These sequences allow one to design siRNA oligonucleotides with terminal TT thymidine dinucleotides.

8. Four or five target sites are chosen from the ranked list of subsequences as described above. For example, in subsequences having 23 nucleotides, the right 21 nucleotides of each chosen 23-mer subsequence are then designed and synthesized for the upper (sense) strand of the siRNA duplex, while the reverse complement of the left 21 nucleotides of each chosen 23-mer subsequence are then designed and synthesized for the lower (antisense) strand of the siRNA duplex. If terminal TT residues are desired for the sequence (as described in paragraph 7), then the two 3' terminal nucleotides of both the sense and antisense strands are replaced by TT prior to synthesizing the oligos.

9. The siRNA oligonucleotides are screened in an in vitro, cell culture or animal model system to identify the most active siRNA oligonucleotide or the most preferred target site within the target RNA sequence.

In a preferred embodiment, the siRNA is at least 19 bp, preferably at least 21 bp in length; the sense strand bears a 5' triphosphate; the end that bears the 5' triphosphate is a blunt end and the other end is a blunt end, a 3' overhang of 1 or 2 nucleotide(s), or a 5' overhang of 1 or 2 nucleotide(s). Preferably, the end that does not bear 5' triphosphate is a blunt end or a 3' overhang of 1 or 2 nucleotide(s), more preferably a 3' overhang of 1 or 2 nucleotide(s).

In preferred embodiments, the siRNA or shRNA is specific for a disease/disorder-associated gene. As widely used in the art, the term "a disease/disorder-related gene" refers to a gene that is expressed in a cell in a disease/disorder but not expressed in a normal cell or a gene that is expressed at a higher level in a cell in a disease/disorder than in a normal cell. In a preferred embodiment, the expression of the disease/disorder-associated gene causes or contributes to the establishment and/or progression of the disease/disorder.

In one embodiment, the disease/disorder is a tumor or a cancer and the disease/disorder-associated gene is an oncogene. Examples of oncogenes include wild-type and/or mutant Bcl-2, c-Myc, c-Ras, c-Met, Her2, EGFR, PDGFR, VEGFR, Edg4, Edg7, S1P, Raf, ERK WNT, Survivin, HGF, cdk2, cdk4, MITF, cyclin D1, GRO and mcl-1. A particular preferred oncogene is Bcl-2.

In another embodiment, the disease/disorder is a viral infection and the disease/disorder-associated gene is a gene which is or the product of which is required for host cell recognition, host cell entry, viral replication, viral partical assembly, and/or viral transmission. The disease/disorder-associated gene may be a viral gene or a host gene. An example of a viral gene is HbsAg of HBV.

Pharmaceutical Composition

The present invention provides a pharmaceutical composition comprising at least one of the oligonucleotide preparation of the invention described above and a pharmaceutically acceptable carrier.

By "at least one", it is meant that one or more oligonucleotide preparation(s) of the same or different oligonucleotide(s) can be used together.

In a preferred embodiment, the pharmaceutical composition further comprises an agent which facilitates the delivery of the oligonucleotide into a cell, in particular, into the cytosol of the cell.

In one embodiment, the delivery agent is a complexation agent which forms a complex with the oligonucleotide and facilitates the delivery of the oligonucleotide into cells. Complexation agents are also referred to as "transfection agents" in the art. Any complexation agent which is compatible with the intended use of the pharmaceutical composition can be employed. Examples of complexation agents include polymers and biodegradable microspheres. The polymer is preferably a cationic polymer, more preferably a cationic lipid. Examples of cationic lipids include DOTAP (Roche) and Lipofectamine (Invitrogen). An other example of a lipid-based complexation agent is FuGene (Roche). Examples of a polymer include polyethylenimine (PEI) such as in vivo-jetPEI™ (PolyPlus) and collagen derivatives. Examples of biodegradable microspheres include liposomes, virosomes, SMARTICLES® (Novosom, Halle), stable-nucleic-acid-lipid particles (SNALPs), SICOMA-TRIX® (CSL Limited), and poly (D,L-lactide-co-glycolide) copolymer (PLGA) microspheres.

In another embodiment, the delivery agent is a virus, preferably a replication-deficient virus. The oligonucleotide to be delivered is contained in the viral capsule and the virus may be selected based on its target specificity. Examples of useful viruses include polymyxoviruses which target upper respiratory tract epithelia and other cells, hepatitis B virus which targets liver cells, influenza virus which targets epithelial cells and other cells, adenoviruses which targets a number of different cell types, papilloma viruses which targets epithelial and squamous cells, herpes virus which targets neurons, retroviruses such as HIV which targets CD4$^+$ T cells, dendritic cells and other cells, modified Vaccinia Ankara which targets a variety of cells, and oncolytic viruses which target tumor cells. Examples of oncolytic viruses include naturally occurring wild-type Newcastle disease virus, attenuated strains of reovirus, vesicular stomatitis virus (VSV), and genetically engineered mutants of herpes simplex virus type 1 (HSV-1), adenovirus, poxvirus and measles virus.

In addition to being delivered by a delivery agent, the oligonucleotide and/or the pharmaceutical composition can be delivered into cells via physical means such as electroporation, shock wave administration, ultrasound triggered transfection, and gene gun delivery with gold particles.

The pharmaceutical composition may further comprise another agent such as an agent that stabilizes the oligonucleotide. Examples of a stabilizing agent include a protein that complexes with the oligonucleotide to form an iRNP, chelators such as EDTA, salts, and RNase inhibitors.

In certain embodiments, the pharmaceutical composition, in particular, the pharmaceutical composition comprising an oligonucleotide preparation according to the first and the second aspect of the invention, further comprises one or more pharmaceutically active therapeutic agent(s). Examples of a pharmaceutically active agent include immunostimulatory agents, anti-viral agents, antibiotics, anti-fungal agents, anti-parasitic agents, anti-tumor agents, cytokines, chemokines, growth factors, anti-angiogenic factors, chemotherapeutic agents, antibodies and gene silencing agents. Preferably, the pharmaceutically active agent is selected from the group consisting of an immunostimulatory agent, an anti-viral agent and an anti-tumor agent. The more than one pharmaceutically active agents may be of the same or different category.

In certain embodiments, the pharmaceutical composition, in particular, the pharmaceutical composition comprising an oligonucleotide preparation according to the first and the second aspect of the invention, further comprises an antigen, an anti-viral vaccine, an anti-bacterial vaccine, and/or an anti-tumor vaccine, wherein the vaccine can be prophylactic and/or therapeutic.

In certain embodiments, the pharmaceutical composition, in particular, the pharmaceutical composition comprising an oligonucleotide preparation according to the first and the second aspect of the present invention, further comprise retinoid acid, IFN-α and/or IFN-β. Without being bound by any theory, retinoid acid, IFN-α and/or IFN-β are capable of sensitizing cells for IFN-α production, possibly through the upregulation of RIG-I expression.

The pharmaceutical composition may be formulated in any way that is compatible with its therapeutic application, including intended route of administration, delivery format and desired dosage. Optimal pharmaceutical compositions may be formulated by a skilled person according to common general knowledge in the art, such as that described in Remington's Pharmaceutical Sciences (18th Ed., Gennaro A R ed., Mack Publishing Company, 1990).

The pharmaceutical composition may be formulated for instant release, controlled release, timed-release, sustained release, extended release, or continuous release.

The pharmaceutical composition may be administered by any route known in the art, including, but not limited to, topical, enteral and parenteral routes, provided that it is compatible with the intended application. Topic administration includes, but is not limited to, epicutaneous, inhalational, intranasal, vaginal administration, enema, eye drops, and ear drops. Enteral administration includes, but is not limited to, oral, rectal administration and administration through feeding tubes. Parenteral administration includes, but is not limited to, intravenous, intraarterial, intramuscular, intracardiac, subcutaneous, intraosseous, intradermal, intrathecal, intraperitoneal, transdermal, transmucosal, and inhalational administration.

In a preferred embodiment, the pharmaceutical composition is for local (e.g., mucosa, skin) applications, such as in the form of a spray (i.e., aerosol) preparation.

The pharmaceutical composition may be use for prophylactic and/or therapeutic purposes. For example, a spray (i.e., aerosol) preparation may be used to strengthen the anti-viral capability of the nasal and the pulmonary mucosa.

The optimal dosage, frequency, timing and route of administration can be readily determined by a person skilled in the art on the basis of factors such as the disease or condition to be treated, the severity of the disease or condition, the age, gender and physical status of the patient, and the presence or absence of previous treatment.

In Vitro Applications

The present application provides the in vitro use of the oligonucleotide preparation of the invention described above. In particular, the present application provides the use of at least one oligonucleotide preparation for inducing an anti-viral response, in particular, a type I IFN response, more specifically, an IFN-α response, in vitro. The present application also provides the use of at least one oligonucleotide preparation or at least one siRNA oligonucleotides as described above for inducing apoptosis of a tumor cell in vitro.

The present invention provides an in vitro method for stimulating an anti-viral response, in particular, a type I IFN response, more specifically, an IFN-α response in a cell, comprising the steps of:
  (a) mixing at least one oligonucleotide of the invention described above with a complexation agent; and
  (b) contacting a cell with the mixture of (a), wherein the cell expresses RIG-I.

The cells may express RIG-I endogenously and/or exogenously from an exogenous nucleic acid (RNA or DNA). The exogenous DNA may be a plasmid DNA, a viral vector, or a portion thereof. The exogenous DNA may be ingerated into the genome of the cell or may exisit extra-chromosomally. The cells include, but are not limited to, primary immune cells, primary non-immune cells, and cell lines. Immune cells include, but are not limited to, peripheral blood mononuclear cells (PBMC), plasmacytoid dendritric cells (PDC), myeloid dendritic cells (MDC), macrophages, monocytes, B cells, natural killer cells, granulocytes, CD4+ T cells, CD8+ T cells, and NKT cells. Non-immune cells include, but are not limited to, fibroblasts, endothelial cells, epithelial cells, and tumor cells. Cell lines may be derived from immune cells or non-immune cells.

The present invention provides an in vitro method for inducing apoptosis of a tumor cell, comprising the steps of:
  (a) mixing at least one oligonucleotide of the invention described above with a complexation agent; and
  (b) contacting a tumor cell with the mixture of (a).

The tumor cell may be a primary tumor cell freshly isolated from a vertebrate animal having a tumor or a tumor cell line.

Preferably, the oligonucleotide preparation is according to the first aspect of the invention described above.

In Vivo Applications

The present application provides the in vivo use of the oligonucleotide preparation or the siRNA oligonucleotide of the invention described above.

In particular, the present application provides at least one oligonucleotide preparation for inducing an anti-viral response, in particular, a type I IFN response, more specifically, an IFN-α response, in a vertebrate animal, in particular, a mammal. The present application further provides at least one oligonucleotide preparation for inducing apoptosis of a tumor cell in a vertebrate animal, in particular, a mammal. The present application additionally provides at least one oligonucleotide preparation for preventing and/or treating a disease and/or disorder in a vertebrate animal, in particular, a mammal, in medical and/or veterinary practice. The invention also provides at least one oligonucleotide preparation for use as a vaccine adjuvant.

Furthermore, the present application provides the use of at least one oligonucleotide preparation for the preparation of a pharmaceutical composition for inducing an anti-viral response, in particular, a type I IFN response, more specifically, an IFN-α response, in a vertebrate animal, in particular, a mammal. The present application further provides the use of at least one oligonucleotide preparation or at least one siRNA oligonucleotide as described above for the preparation of a pharmaceutical composition for inducing apoptosis of a tumor cell in a vertebrate animal, in particular, a mammal. The present application additionally provides the use of at least one oligonucleotide preparation for the preparation of a pharmaceutical composition for preventing and/or treating a disease and/or disorder in a vertebrate animal, in particular, a mammal, in medical and/or veterinary practice.

Preferably, the oliognucleotide preparation is according to the first aspect of the invention described above.

The diseases and/or disorders include, but are not limited to, infections, tumors/cancers, and immune disorders.

Infections include, but are not limited to, viral infections, bacterial infections, anthrax, parasitic infections, fungal infections and prion infection.

Viral infections include, but are not limited to, infections by hepatitis C, hepatitis B, influenza virus, herpes simplex virus (HSV), human immunodeficiency virus (HIV), respiratory syncytial virus (RSV), vesicular stomatitis virus (VSV), cytomegalovirus (CMV), poliovirus, encephalomyocarditis virus (EMCV), human papillomavirus (HPV) and smallpox virus. In one embodiment, the infection is an upper respiratory tract infection caused by viruses and/or bacteria, in particular, flu, more specifically, bird flu.

Bacterial infections include, but are not limited to, infections by streptococci, staphylococci, *E. Coli*, and *pseudomonas*. In one embodiment, the bacterial infection is an intracellular bacterial infection which is an infection by an intracellular bacterium such as mycobacteria (tuberculosis), *chlamydia, mycoplasma, listeria*, and an facultative intracelluar bacterium such as *staphylococcus aureus*.

Parasitic infections include, but are not limited to, worm infections, in particular, intestinal worm infection.

In a preferred embodiment, the infection is a viral infection or an intracellular bacterial infection. In a more preferred embodiment, the infection is a viral infection by hepatitis C, hepatitis B, influenza virus, RSV, HPV, HSV1, HSV2, and CMV.

In a further preferred embodiment, the present application provides the use of at least one oligonucleotide preparation or the siRNA oligonucleotide as described above for the preparation of a pharmaceutical composition for inducing apoptosis. In a further preferred embodiment, the present application provides the use of at least one oligonucleotide preparation for the preparation of a pharmaceutical composition for both (a) inducing an anti-viral response, in particular, a type I IFN response, more specifically, an IFN-α response, and b) downregulation of a tumor target gene, in particular Bcl-2, in a vertebrate animal, in particular, a mammal. The present application further provides the use of at least one oligonucleotide preparation for the preparation of a pharmaceutical composition for inducing apoptosis of a tumor cell in a vertebrate animal, in particular, a mammal.

Tumors include both benign and malignant tumors (i.e., cancer).

Cancers include, but are not limited to biliary tract cancer, brain cancer, breast cancer, cervical cancer, choriocarcinoma, colon cancer, endometrial cancer, esophageal cancer, gastric cancer, intraepithelial neoplasm, leukemia, lymphoma, liver cancer, lung cancer, melanoma, myelomas, neuroblastoma, oral cancer, ovarian cancer, pancreatic cancer, prostate cancer, rectal cancer, sarcoma, skin cancer, testicular cancer, thyroid cancer and renal cancer, preferably the cancer is melanoma.

In certain embodiments, the cancer is selected from hairy cell leukemia, chronic myelogenous leukemia, cutaneous T-cell leukemia, chronic myeloid leukemia, non-Hodgkin's lymphoma, multiple myeloma, follicular lymphoma, malignant melanoma, squamous cell carcinoma, renal cell carcinoma, prostate carcinoma, bladder cell carcinoma, breast carcinoma, ovarian carcinoma, non-small cell lung cancer, small cell lung cancer, hepatocellular carcinoma, basaliom, colon carcinoma, cervical dysplasia, and Kaposi's sarcoma (AIDS-related and non-AIDS related).

Immune disorders include, but are not limited to, allergies, autoimmune disorders, and immunodeficiencies.

Allergies include, but are not limited to, respiratory allergies, contact allergies and food allergies.

Autoimmune diseases include, but are not limited to, multiple sclerosis, diabetes mellitus, arthritis (including rheumatoid arthritis, juvenile rheumatoid arthritis, osteoarthritis, psoriatic arthritis), encephalomyelitis, myasthenia gravis, systemic lupus erythematosis, autoimmune thyroiditis, dermatisis (including atopic dermatitis and eczematous dermatitis), psoriasis, Siogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis.

Immunodeficiencies include, but are not limited to, spontaneous immunodeficiency, acquired immunodeficiency (including AIDS), drug-induced immunodeficiency or immunosuppression (such as that induced by immunosuppressants used in transplantation and chemotherapeutic agents used for treating cancer), and immunosuppression caused by chronic hemodialysis, trauma or surgical procedures.

In a preferred embodiment, the immune disorder is multiple sclerosis.

In certain preferred embodiments, the oligonucleotide has gene silencing activity. The oligonucleotide thus has two functionalities, gene silencing and immune stimulating, combined in one molecule. In preferred embodiments, the oligonucleotide has gene-silencing activity that is specific for a disease/disorder-associated gene, such as an oncogene or a gene required for viral infection and/or replication.

In certain embodiments, the oligonucleotide is used in combination with one or more pharmaceutically active agents such as immunostimulatory agents, anti-viral agents, antibiotics, anti-fungal agents, anti-parasitic agents, anti-tumor agents, cytokines, chemokines, growth factors, anti-angiogenic factors, chemotherapeutic agents, antibodies and gene silencing agents. Preferably, the pharmaceutically active agent is selected from the group consisting of an immunostimulatory agent, an anti-viral agent and an anti-tumor agent. The more than one pharmaceutically active agents may be of the same or different category.

In one embodiments, the oligonucleotide is used in combination with an antigen, an anti-viral vaccine, an anti-bacterial vaccine, and/or an anti-tumor vaccine, wherein the vaccine can be prophylactic and/or therapeutic. The oligonucleotide can serve as an adjuvant.

In another embodiment, the oligonucleotide is used in combination with retinoic acid and/or type I IFN (IFN-α and/or IFN-β). Without being bound by any theory, retinoid acid, IFN-α and/or IFN-β are capable of sensitizing cells for IFN-α production, possibly through the upregulation of RIG-I expression.

In other embodiments, the pharmaceutical composition is for use in combination with one or more prophylactic and/or therapeutic treatments of diseases and/or disorders such as infection, tumor, and immune disorders. The treatments may be pharmacological and/or physical (e.g., surgery, radiation).

Vertebrate animals include, but are not limited to, fish, amphibians, birds, and mammals. Mammals include, but are not limited to, rats, mice, cats, dogs, horses, sheep, cattle, cows, pigs, rabbits, non-human primates, and humans. In a preferred embodiment, the mammal is human.

The present application provides at least one oligonucleotide preparation according to the second aspect of the invention described above for inducing an anti-viral response, in particular, a type I IFN response, more specifically, an IFN-α response, in a vertebrate animal, in particular, a mammal which is infected with a negative single-strand RNA virus. The present application also provides at least one oligonucleotide preparation according to the second aspect of the invention described above for preventing and/or treating an infection by a negative single-strand RNA virus in a vertebrate animal, in particular, a mammal, in medical and/or veterinary practice.

Furthermore, the present application provides the use of at least one oligonucleotide preparation according to the second aspect of the invention described above for the preparation of a pharmaceutical composition for inducing an anti-viral response, in particular, a type I IFN response, more specifically, an IFN-α response, in a vertebrate animal, in particular, a mammal which is infected with a negative single-strand RNA virus. The present application also provides the use of at least one oligonucleotide preparation according to the second aspect of the invention described above for the preparation of a pharmaceutical composition for preventing and/or treating an infection by a negative single-strand RNA virus in a vertebrate animal, in particular, a mammal, in medical and/or veterinary practice.

In certain embodiments, the oligonucleotide is used in combination with one or more pharmaceutically active agents such as immunostimulatory agents, anti-viral agents, cytokines, chemokines, growth factors, antibodies and gene silencing agents. Preferably, the pharmaceutically active agent is selected from an immunostimulatory agent or an anti-viral agent. The more than one pharmaceutically active agents may be of the same or different category.

In one embodiments, the oligonucleotide is used in combination with an anti-viral vaccine, wherein the vaccine can be prophylactic and/or therapeutic.

In another embodiment, the oligonucleotide is used in combination with retinoic acid and/or type I IFN (IFN-α and/or IFN-β). Without being bound by any theory, retinoid acid, IFN-α and/or IFN-β are capable of sensitizing cells for IFN-α production, possibly through the upregulation of RIG-I expression.

In other embodiments, the pharmaceutical composition is for use in combination with one or more prophylactic and/or therapeutic treatments of a viral infection.

The present invention provides at least one oligonucleotide preparation according to the third aspect of the invention described above for preventing and/or inhibiting an anti-viral, in particular, an type I IFN, more specifically an IFN-α response against a negative single-strand RNA virus in a mammal. The present invention also provides the use of at least one oligonucleotide preparation according to the third aspect of the invention described above for the preparation of a pharmaceutical composition for preventing and/or inhibiting an anti-viral, in particular, an type I IFN, more specifically an IFN-α response against a negative single-strand virus in a mammal.

In one embodiment, the oligonucleotide preparation may be used for treating virus-induced hemorrhagic fever. Virus-induced hemorrhagic fever includes, but is not limited to, hemorrhagic fever induced by Ebola virus, Marburg virus, Lassa fever virus, the New World arenaviruses (Guanarito, Machupo, Junin, and Sabia), Rift Valley fever virus, and Crimean Congo hemorrhagic fever viruses.

The oligonucleotide preparation may be used alone or in combinations with one or more immunosuppressant.

Negative single-strand RNA viruses include, but are not limited to, influenza A virus, Rabies virus, Newcastle disease virus (NDV), vesicular stomatitis virus (VSV), Measles virus, mumps virus, respiratory syncytial virus (RSV), Sendai virus, Ebola virus, and Hantavirus.

Methods for Preparing an Oligonucleotide Preparation

The present invention provides a method for preparing an oligonucleotide preparation of the first aspect of the invention described above.

Specifically, the present invention provides a method for preparing a double-strand oligonucleotide preparation having immunostimulatory, in particular, type I IFN-inducing, more specifically IFN-α-inducing activity, comprising the steps of:
(a) identifying two oligonucleotide sequences, wherein at least one of the nucleotide sequences comprises at least 1 ribonucleotide at the 5' end, wherein the sequence of the at least 19, preferably at least 21 nucleotides at the 5' end of the at least one oligonucleotide sequence which comprises at least 1 ribonucleotide at the 5' end has 100% complementarily with the sequence of the at least 19, preferably at least 21 nucleotides at the 3' end of the other oligonucleotide sequence, thereby forming a blunt end;
(b) preparing two essentially homogenous populations of two oligonucleotides having the sequences identified in (a), wherein the at least one oligonucleotide which comprises at least 1 ribonucleotide at the 5' end which forms the blunt end bears a 5' triphosphate on the most 5' ribonucleotide;
(c) preparing an essentially homogenous population of a double-strand oligonucleotide from the two oligonucleotides prepared in (b); and
(d) optionally testing the type I IFN-inducing activity of the double-strand oligonucleotide.

In one embodiment, the oligonucleotide contained in the oligonucleotide preparation prepared by the above method has one blunt end bearing one 5' triphosphate or two blunt ends each bearing one 5' triphosphate. In one embodiment, the oligonucleotide contained in the oligonucleotide preparation prepared by the above method has one blunt end bearing one 5' triphosphate and one 5' overhang of 1 or 2 nucleotides which does not bear any 5' triphosphate.

Furthermore, the present invention provides a method for preparing a single-strand oligonucleotide preparation having immunostimulatory, in particular, type I IFN-inducing, more specifically IFN-α-inducing activity, comprising the steps of:
(a) identifying an oligonucleotide sequence, wherein the nucleotide sequence comprises at least 1 ribonucleotide at the 5' end, wherein the sequence of the at least 19, preferably at least 21 nucleotides at the 5' end of the oligonucleotide sequence has 100% complementarily with the sequence of the at least 19, preferably at least 21 nucleotides at the 3' end of the oligonucleotide sequence;
(b) preparing an essentially homogenous population of an oligonucleotide having the sequence identified in (a), wherein the oligonucleotide bears a 5' triphosphate on the most 5' ribonucleotide; and
(c) optionally testing the type I IFN-inducing activity of the single-strand oligonucleotide.

In a preferred embodiment, the at least one ribonucleotide at the 5' end, which forms the blunt end, of the oligonucleotide sequence identified in the above methods is an A.

In further preferred embodiments, the sequence of the first 4 ribonucleotides at the 5' end, which forms the blunt end, of the oligonucleotide sequence identified in the above methods is selected from: AAGU (No. 1), AAAG (No. 2), AUGG (No. 3), AUUA (No. 4), AACG (No. 5), AUGA (No. 6), AGUU (No. 7), AUUG (No. 8), AACA (No. 9), AGAA (No. 10), AGCA (No. 11), AACU (No. 12), AUCG (No. 13), AGGA (No. 14), AUCA (No. 15), AUGC (No. 16), AGUA (No. 17), AAGC (No. 18), AACC (No. 19), AGGU (No. 20), AAAC (No. 21), AUGU (No. 22), ACUG (No. 23), ACGA (No. 24), ACAG (No. 25), AAGG (No. 26), ACAU (No. 27), ACGC (No. 28), AAAU (No. 29), ACGG (No. 30), AUUC (No. 31), AGUG (No. 32), ACAA (No. 33), AUCC (No. 34), AGUC (No. 35), wherein the sequence is in the 5'→3' direction. In more preferred embodiments, the sequence of the first 4 ribonucleotides is selected from Nos. 1-19, more preferably from Nos. 1-9, even more preferably from Nos. 1-4.

In an embodiment, the methods further comprises the step of 2'-O-methylating the most 3' nucleotide which base pairs with the most 5' ribonucloetide which bears the 5' triphosphate and which forms the blunt end.

The present invention further relates to a method for preparing an oligonucleotide preparation having the combined activity of target gene-silencing and type I IFN-inducing activity, comprising the steps of: (a) identifying an oligonucleotide sequence, wherein the nucleotide sequence is specific for the target gene and comprises at least 1 ribonucleotide at the 5' end, wherein the sequence of the at least 19, preferably at least 21 nucleotides at the 5' end of the oligonucleotide sequence has 100% complementarily with the sequence of the at least 19, preferably at least 21 nucleotides at the 3' end of the same oligonucleotide sequence; (b) preparing an essentially homogenous population of an oligonucleotide having the sequence identified in (a), wherein the oligonucleotide bears a 5' triphosphate on the most 5' ribonucleotide; bears a 5' triphosphate at both most 5' ribonucleotide, or just one at the one or the other 5'-end of a double strand RNA oligonucleotide (c) optionally testing the type I IFN-inducing activity of the single-strand oligonucleotide; and (d) optionally testing the oligonucleotide for gene-silencing activity.

The present invention further relates to a method for preparing an oligonucleotide preparation having the combined activity of target gene-silencing and type I IFN-inducing activity, comprising the steps of: (a) identifying a nucleotide sequence for a first oligonucleotide, wherein the nucleotide sequence is specific for the target gene; (b) preparing an essentially homogenous population of the first oligonucleotide having the sequence identified in (a), (c) preparing a essentially homogenous population of a second oligonucleotide wherein the nucleotide sequence of the second oligonucleotide is 100% complementary to the nucleotide sequence of the first oligonucleotide; (d) optionally testing the type I IFN-inducing activity of the single-strand oligonucleotide; and (e) optionally testing the oligonucleotide for gene-silencing activity; wherein the first and/or the second oligonucleotide bears a 5' triphosphate on the most 5' ribonucleotide or on both 5' ribonucleotides; wherein the 5' triphosphate is free of any cap structure; and wherein the first and the second oligonucleotide has at least 19, preferably at least 21, more preferably at least 24 base pairs in length.

Methods for Modulating the Immunostimulatory Activity of an Oligonucleotide

The present invention provides a method for enhancing the immunostimulatory, in particular, type I IFN-inducing, more specifically IFN-α-inducing activity of an oligonucleotide, wherein the oligonucleotide has at least one blunt end and comprises at least 1 ribonucleotide at the 5' end at the blunt end, wherein the blunt end bears a 5' triphosphate attached to the most 5' ribonucleotide, wherein the 5' triphosphate is free of any cap structure, and wherein the blunt end is followed by a fully double-stranded section which is at least 19, preferably at least 21 base pair (bp) in length, comprising the step of 2'-O-methylating the most 3' nucleotide which base pairs with the most 5' ribonucleotide bearing the 5' triphosphate at the blunt end.

The present invention also provides a method for reducing the immunostimulatory, in particular, type I IFN-inducing, more specifically IFN-α-inducing activity of an oligonucleotide, wherein the oligonucleotide has at least one blunt end and comprises at least 1 ribonucleotide at the 5' end at the blunt end, wherein the blunt end bears a 5' triphosphate attached to the most 5' ribonucleotide, wherein the 5' triphosphate is free of any cap structure, and wherein the blunt end is followed by a fully double-stranded section which is at least 19, preferably at least 21 base pair (bp) in length, comprising the step of 2'-O-methylating a nucleotide which is not the most 3' nucleotide which base pairs with the most 5' ribonucleotide bearing the 5' triphosphate at the blunt end.

In a preferred embodiment, the nucleotide to be 2'-O-methylated is the nucleotide immediately 5' to the most 3' nucleotide which base pairs with the most 5' ribonucleotide bearing the 5' triphosphate at the blunt end.

The present invention is illustrated by the following Examples.

The Examples are for illustration purposes only and are by no means to be construed to limit the scope of the invention.

EXAMPLES

Materials and Methods
1. Cells

Human PBMC were prepared from whole blood donated by young healthy donors by Ficoll-Hypaque density gradient centrifugation (Biochrom, Berlin, Germany). PDC were isolated by MACS using the blood dendritic cell Ag (BCDA)-4 dendritic cell isolation kit from Miltenyi Biotec (Bergisch-Gladbach, Germany). Briefly, PDC were labelled with anti-BDCA-4 Ab coupled to colloidal paramagnetic microbeads and passed through a magnetic separation column twice (LS column, then MS column; Miltenyi Biotec). The purity of isolated PDC (lineage-negative, MHC-II-positive and CD123-positive cells) was above 95%. Before isolation of monocytes, PDC were depleted by MACS (LD column; Miltenyi Biotec) and then monocytes were isolated using the monocyte isolation kit II (Miltenyi Biotec). MDCs were purified from PBMC by immunomagnetic sorting with anti-CD1c beads (CD1c (BDCA-1)+Dendritic Cell Isolation Kit, human, Miltenyi Biotec). Viability of all cells was above 95%, as determined by trypan blue exclusion. Unless indicated otherwise, cells were cultured in 96-well plates for stimulation experiments. MDCs (0.5×10⁶/ml) were kept in RPMI 1640 containing 10% FCS, 1.5 mM L-glutamine, 100 U/ml penicillin and 100 μg/ml streptomycin. PDCs (0.25× 10⁶/ml) were cultured in the same medium supplemented with 10 ng/ml IL-3 (R&D Systems GmbH). Monocytes (0.5×10⁶/ml) were resuspended in RPMI medium with 2% AB serum (BioWhittaker, Heidelberg, Germany), 1.5 mM L-glutamine, 100 U/ml penicillin and 100 μg/ml streptomycin. All compounds were tested for endotoxin contamination prior to use.

2. Mice

TLR7-deficient (TLR7⁻/⁻) mice were kindly provided by S. Akira[3]. Female C57BLJ6 mice were purchased from Harlan-Winkelmann (Borchen, Germany). Mice were 6-12 weeks of age at the onset of experiments. Animal studies were approved by the local regulatory agency (Regierung von Oberbayern, Munich, Germany).

3. RNAs

Chemically synthesized RNA oligonucleotides were purchased from Eurogentec (Leiden, Belgium), MWG-BIO-TECH AG (Ebersberg, Germany), biomers.net GmbH (Ulm, Germany), and optionally modified by Janos Ludwig (Rockefeller Univ., USA). In vitro transcribed RNAs were prepared using the Megashort Script Kit (Ambion, Huntingdon, UK) following the manufacture's instructions. In vitro transcription was carried out overnight at 37° C. The DNA template was digested using DNase I (Ambion). RNAs were purified by phenol:chloroform extraction and alcohol precipitation Excess salts and NTPs were removed by passing the RNAs through a Mini Quick Spin™ Oligo Column (Roche). Size and integrity of RNAs was checked via gel electrophoresis. CpG-ODN was purchased from Coley Pharmaceutical Group (Wellesley, USA) or Metabion (Martinsried, Germany). The 2'-O-methylated oligonucleotides were obtained from biomers.net GmbH.

4. Cell Stimulation (Transfection)

Unless otherwise indicated, 200 ng of the purified RNA oligonucleotides were transfected into cells using 0.5 μl of Lipofectamine 2000 (Invitrogen) in each well of a 96-well plate according to the manufacturer's protocol. CpG ODN was used at a final concentration of 3 μg/ml. For transfection with the polycationic polypeptide poly-L-arginine (Sigma, P7762), 200 ng nucleic acid diluted in PBS (PAA Laboratories GmBH) were mixed with 280 ng poly-L-arginine and incubated for 20 min prior to stimulation. In some experiments, cells were pre-treated with 1 or 2.5 μg/ml chloroquine (Sigma) for 30 min prior to stimulation. 24 h post-stimulation/transcription, tissue culture supernatants were collected and assayed for IFN-α production.

5. IFN-α ELISA

Human IFN-α was assessed in cell culture supernatants harvested 24 hours after stimulation/transfection using the IFN-α module set (Bender MedSystems, Graz, Austria) according to manufacturer's recommendations. Murine IFN-α was measured according to the following protocol: monoclonal rat anti-mouse IFN-α (clone RMMA-1) was used as the capture Ab, polyclonal rabbit anti-mouse IFN-α serum was used for detection (both PBL Biomedical Laboratories), and HRP-conjugated donkey anti-rabbit IgG was used as the secondary reagent (Jackson ImmunoResearch Laboratories). Mouse rIFN-α (PBL Biomedical Laboratories) was used as the standard (IFN-α concentration in IU/ml).

RESULTS

Example 1. RNA Oligonucleotides Bearing 5' Triphosphate are Recognized by Different Receptors in Monocytes and PDCs PDCs, MDCs and monocytes were all found to be able to respond to stimulation of RNA oligonucleotides bearing 5' triphosphate (3pRNA) by producing IFN-α (data not shown). To identify the receptors involved in the recognition of 3pRNA in these different immune cell populations, in vitro transcribed 3pRNA (Table 1) were transfected into these cells in the presence and absence of chloroquine, a potent inhibitor of TLR7, TLR8 and TLR9-mediated nucleic aid recognition.

TABLE 1

RNA and DNA oligonucleotide sequences.

| name | sequence | type | SEQ ID NO |
|---|---|---|---|
| GA | 5'-pppGGGGGGGGGGGAAAAAAAAAAA-3' | RNA, in vitro transcribed | 1 |
| GFPs | 5'-pppGGGGCUGACCCUGAAGUUCAUCUU-3' | RNA, in vitro transcribed | 2 |
| SynRNA | 5'-oHGGGGCUGACCCUGAAGUUCAUCUU-3' | RNA, synthetic | 2 |
| 3pRNA | 5'-pppGGGGCUGACCCUGAAGUUCAUCUU-3' | RNA, in vitro transcribed | 2 |
| CpG | 5'-GGGGGACGATCGTCGGGGGG-3' | DNA, synthetic | 3 |

(ppp: triphosphate; under lined letters: phosphorothioate linkage 3' of the base; bold letters, CpG dinucleotides)

As shown in FIG. 1A, whereas 3pRNA-induced IFN-α production from monocytes was not affected by the addition of chloroquine, 3pRNA-induced IFN-α production from PDCs was greatly diminished by the addition of chloroquine.

Furthermore, as shown in FIG. 1A, the ability of 3pRNA to induce IFN-α from PDCs depended on the presence of U in the sequence which is known to be a molecular signature recognized by TLR7.

Moreover, as shown in FIG. 1B, whereas PDCs from wild-type mice responded to stimulation by 3pRNA by producing IFN-α, this response was dramatically diminished, if not completely absent, in PDCs from TLR7-deficient (TLR7$^{-/-}$) mice.

Taken together, these results suggest that whereas the recognition of 3pRNA in PDCs is primarily mediated by TLR7 in a nucleotide sequence-dependent manner, the recognition of 3pRNA in monocytes is primarily, if not entirely, mediated by RIG-I and is nucleotide sequence-independent.

Example 2. IFN-α Induction in Monocytes Strictly Requires the Presence of a 5' Triphosphate Synthetic RNA oligonucleotides bearing 5' monophosphate (Table 2) were transfected into purified primary human monocytes. An in vitro transcribed RNA bearing 5' triphosphate was used as a positive control. The level of IFN-α secretion was determined 24 hours after transfection/stimulation.

TABLE 2

RNA oligonucleotide sequences.

| name | sequence | type | SEQ ID NO |
|---|---|---|---|
| 27+0 s | 5'-OHAAGCUGACCCUGAAGUUCAUCUGCACC-3' | RNA, synthetic | 4 |
| 27+0 a | 5'-OHGGUGCAGAUGAACUUCAGGGUCAGCUU-3' | RNA, synthetic | 5 |
| 27+0 ds | 5'-OHAAGCUGACCCUGAAGUUCAUCUGCACC-3'<br>3'-UUCGACUGGGACUUCAAGUAGACGUGGOH-5' | RNA, synthetic | |
| 27+2 s | 5'-OHGCUGACCCUGAAGUUCAUCUGCACCACUU-3' | RNA, synthetic | 6 |
| 27+2 a | 5'-OHGUGGUGCAGAUGAACUUCAGGGUCAGCUU-3' | RNA, synthetic | 7 |
| 27+2 ds | 5'-OHGCUGACCCUGAAGUUCAUCUGCACCACUU-3'<br>3'-UUCGACUGGGACUUCAAGUAGACGUGGUGOH-5' | RNA, synthetic | |
| 3pRNA | 5'-pppGGGGCUGACCCUGAAGUUCAUCUU-3' | RNA, in vitro transcribed | 2 |
| CpG-A | 5'-GGGGGACGATCGTCGGGGGG-3' | DNA | 3 |

(p: monophosphate; ppp: triphosphate; under lined letters: phosphorothioate linkage 3' of the base; bold letters, CpG dinucleotides)

As shown in FIG. 2B, regardless of the presence or the absence of a 5' triphosphate, all RNA oligonucleotides tested were capable of inducing IFN-α production from PDCs which primarily use TLR7 for short dsRNA recognition (see Example 1).

As shown in FIG. 2B, whereas in vitro transcribed RNA oligonucleotide, 3pRNA, bearing 5' triphosphate, induced a significant amount of IFN-α, synthetic RNA oligonucleotides bearing 5' OH failed to induce any IFN-α production from monocytes, regardless whether the oligonucleotide had blunt ends or 3' overhangs.

These results indicate that 5' triphosphate is strictly required for IFN-α induction in monocytes. Since RNA recognition and IFN-α induction is primarily mediated by RIG-I in monocytes (see Example 1), this data suggest that blunt end is not recognized by RIG-I, at least not in the absence of 5' triphosphate.

Example 3. Blunt End Augments the Immunostimulatory Activity of Synthetic Double-Stranded Oligonucleotides Bearing 5' Triphosphate Since 3pRNA oligonucleotides are capable of inducing IFN-α production from PDCs via a TLR7-dependent pathway (see Example 1), in order to study RIG-I-dependent induction of IFN-α, RNA oligonucleotides (FIG. 3 & Table 3) were transfected into purified monocytes, PDC-depleted PBMCs (PBMC-PDC) or chloroquine-treated PBMCs (PBMC+Chl).

Figure 3:
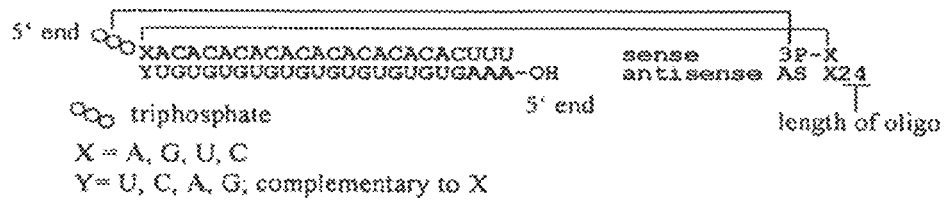
FIG. 3. Experimental design: synthetic RNA oligonucleotides used to test the effect of end structure on the immunostimulatory activity of double-stranded 3pRNA.

The design and the designation of the RNA oligonucleotides are shown in FIG. 3 and the sequences of the oligonucleotides are shown in Table 3.

TABLE 3

RNA and DNA oligonucelotide sequences

| Name | Sequence | 5' end | Type | SEQ ID NO |
|---|---|---|---|---|
| 3P-A | AACACACACACACACACACUUU | 3P | RNA, syn | 8 |
| ivt3P-G | GACACACACACACACACACUUU | 3P | RNA, ivt | 9 |
| 3P-G | GACACACACACACACACACUUU | 3P | RNA, syn | 9 |
| 3P-C | CACACACACACACACACACUUU | 3P | RNA, syn | 10 |
| 3P-U | UACACACACACACACACACUUU | 3P | RNA, syn | 11 |
| HO-A | AACACACACACACACACACUUU | OH | RNA, syn | 8 |
| P-A | AACACACACACACACACACUUU | P | RNA, syn | 8 |
| AS A26 | AAAGUGUGUGUGUGUGUGUGUUGU | OH | RNA, syn | 12 |
| AS A25 | AAAGUGUGUGUGUGUGUGUGUUG | OH | RNA, syn | 13 |
| AS A24+2A | AAAAAGUGUGUGUGUGUGUGUGUU | OH | RNA, syn | 14 |
| AS A24+A | AAAAGUGUGUGUGUGUGUGUGUU | OH | RNA, syn | 15 |
| AS A24 | AAAGUGUGUGUGUGUGUGUGUU | OH | RNA, syn | 16 |
| AS A23 | AAGUGUGUGUGUGUGUGUGUU | OH | RNA, syn | 17 |
| AS A21 | GUGUGUGUGUGUGUGUGUU | OH | RNA, syn | 18 |
| AS A20 | UGUGUGUGUGUGUGUGUU | OH | RNA, syn | 19 |
| AS A19 | GUGUGUGUGUGUGUGUU | OH | RNA, syn | 20 |
| AS A17 | GUGUGUGUGUGUGUU | OH | RNA, syn | 21 |
| AS A15 | GUGUGUGUGUGUU | OH | RNA, syn | 22 |
| AS A13 | GUGUGUGUGUU | OH | RNA, syn | 23 |
| AS G26 | AAAGUGUGUGUGUGUGUGUGUCGU | OH | RNA, syn | 24 |
| AS G25 | AAAGUGUGUGUGUGUGUGUGUCG | OH | RNA, syn | 25 |
| AS G24+2A | AAAAAGUGUGUGUGUGUGUGUGUC | OH | RNA, syn | 26 |
| AS G24+A | AAAAGUGUGUGUGUGUGUGUGUC | OH | RNA, syn | 27 |
| AS G24 | AAAGUGUGUGUGUGUGUGUGUC | OH | RNA, syn | 28 |
| AS G23 | AAGUGUGUGUGUGUGUGUGUC | OH | RNA, syn | 29 |
| AS G21 | GUGUGUGUGUGUGUGUGUC | OH | RNA, syn | 30 |
| AS G20 | UGUGUGUGUGUGUGUGUC | OH | RNA, syn | 31 |

TABLE 3-continued

RNA and DNA oligonucelotide sequences

| Name | Sequence | 5' end | Type | SEQ ID NO |
|------|----------|--------|------|-----------|
| AS G19 | GUGUGUGUGUGUGUGUGUGUC | OH | RNA, syn | 32 |
| AS G17 | GUGUGUGUGUGUGUGUC | OH | RNA, syn | 33 |
| AS G15 | GUGUGUGUGUGUGUC | OH | RNA, syn | 34 |
| AS G13 | GUGUGUGUGUGUC | OH | RNA, syn | 35 |
| AS C26 | AAAGUGUGUGUGUGUGUGUGUGGU | OH | RNA, syn | 36 |
| AS C24 | AAAGUGUGUGUGUGUGUGUGUG | OH | RNA, syn | 37 |
| AS U26 | AAAGUGUGUGUGUGUGUGUGUAGU | OH | RNA, syn | 38 |
| AS U24 | AAAGUGUGUGUGUGUGUGUGUA | OH | RNA, syn | 39 |
| AS23 | AAAGUGUGUGUGUGUGUGUGU | OH | RNA, syn | 40 |
| AS21 | AAAGUGUGUGUGUGUGUGU | OH | RNA, syn | 41 |
| AS19 | AAAGUGUGUGUGUGUGU | OH | RNA, syn | 42 |
| IVT2 | GACGACGACGACGACGACGACGACGAC | 3P | RNA, ivt | 43 |
| dAdT | (AT)$_{200-4000}$ | P | DNA, syn | |

(syn: synthetic; ivt: in vitro transcribed)

As shown in FIGS. 4A, 5A and 6A, a minimal length of 21 nucleotides was required for a double-stranded 3pRNA oligonucleotide to induce IFN-α from monocytes. Furthermore, the highest IFN-α-inducing activity was seen when the double-stranded 3pRNA oligonucleotide had a blunt end at the same end bearing the 5' triphosphate. Blunt end formation at the non-triphosphate end appears not to be preferred as double-stranded oligonucleotides bearing a 1 nt 3' overhang at the non-triphosphate end had higher IFN-α-inducing activity than those having a blunt end at the non-triphosphate end (FIGS. 5A and 6, compare 3P-A+AS A23 and 3P-A+AS A24, or 3P-G+AS G23 and 3P-G+AS G24). Moreover, dsRNA oligonucleotides with an A at the 5' end bearing the 5' triphosphate were more potent in inducing IFN-α than those with a G or U at the same position; dsRNA oligonucleotides with a C at the 5' end bearing the 5' triphosphate was the least potent. Similar results were obtained with PDC-depleted PBMCs and chloroquine-treated PBMCs (FIGS. 4-6, B & C).

In contrast, double-stranded oligonucleotides bearing a 5' monophosphate were not effective at inducing IFN-α, regardless of the end structures (FIG. 6).

These data suggest 5' triphosphate is required for RIG-I recognition. Furthermore, blunt end is a molecular signature recognized by RIG-I; it augments the potency of a synthetic double-stranded RNA oligonucleotide bearing 5' triphosphate at the same end in inducing IFN-α via the RIG-I pathway.

Example 4. Single-Stranded RNA Transcripts can be Generated by In Vitro Transcription Both synthetic dsRNA bearing 5' triphosphate and in vitro transcribed ssRNA have been shown to be able to activate RIG-I[15, 25]. The present inventors found that double-stranded configuration is required for RIG-I activation[19]. It was hypothesized that ssRNA obtained by in vitro transcription was capable of activating RIG-I probably due to the presence of aberrant RNA transcripts which had a double-stranded configuration.

Figure 7:
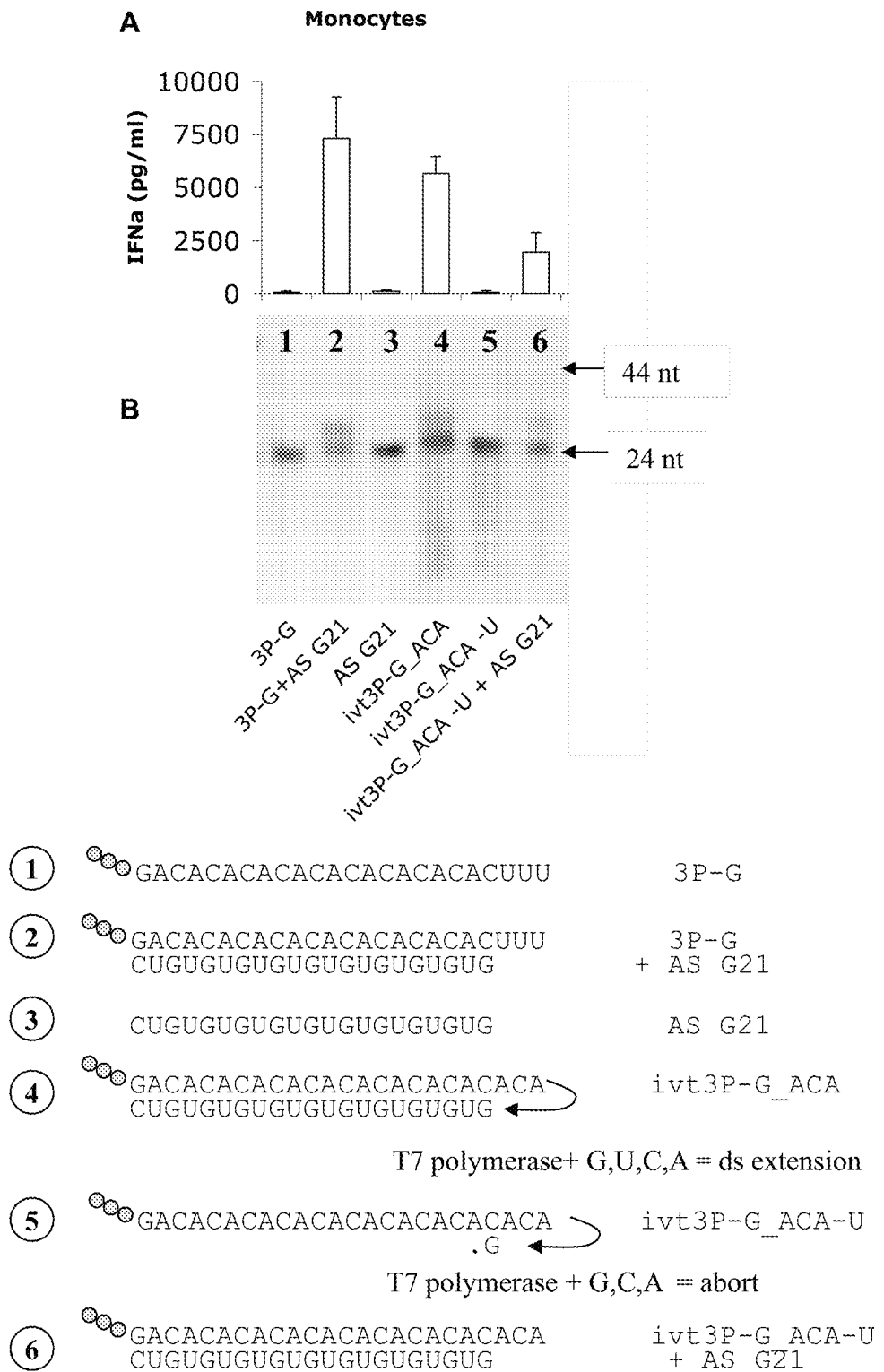
FIG. 7. Single-stranded RNA oligonucleotide can be obtained by in vitro transcription. (A) In vitro transcribed, synthetic or mixed double-stranded or single-stranded oligonucleotides were transfected into purified monocytes. IFN-α production was analyzed 24 hours after stimulation. (B) Urea polyacrylamide gel electrophoresis. (C) Sequence of the oligonucleotides tested.
Figure 8:
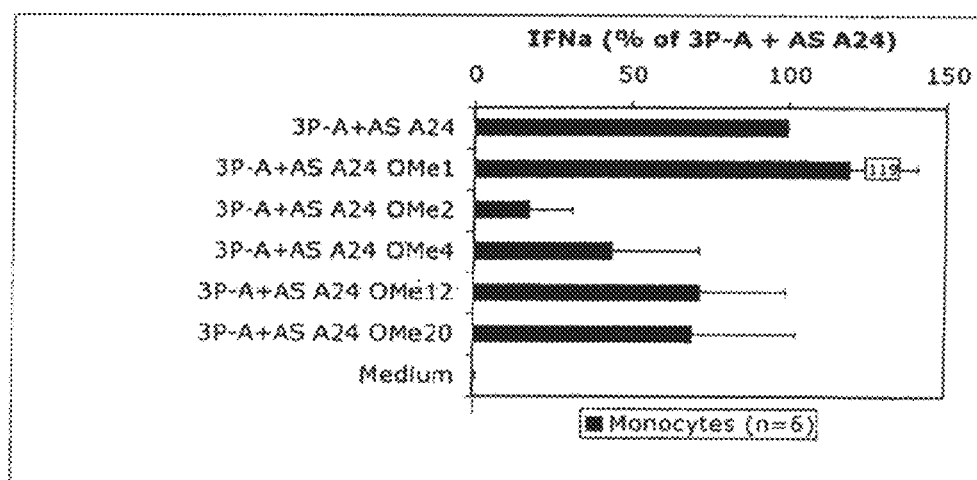
FIG. 8. The effect of 2'-O-methylation on the IFN-α-inducing activity of a blunt ended RNA olignucleotide bearing 5' triphosphate is position-dependent. Purified monocytes were stimulated with 0.8 µg/ml of the indicated double-stranded oligonucleotides. IFN-α production was analyzed 24 hours after stimulation. Data from six independent donors were summarized and are depicted as mean values±SEM.

Indeed, when ssRNA was transcribed in vitro in the presence of all 4 NTP's (i.e., ATP, UTP, GTP, CTP) and run on a urea polyacrylamide gel, two bands were observed, indicating the presence double-stranded species (FIG. 7C, sample 4, "ivt3P-G_ACA").

TABLE 4

Sequence of RNA oligonucleotides.

| name | sequence | type | SEQ ID NO |
|------|----------|------|-----------|
| 3P-G | 5'-pppGACACACACACACACACACACUUU-3' | RNA, synthetic | 9 |
| AS-G21 | 5'-OHGUGUGUGUGUGUGUGUGUGUC-3' | RNA, synthetic | 30 |
| inv3P-G_ACA | 5'-pppGACACACACACACACACACACA-3' | RNA, in vitro transcribed | 44 |

Subsequently, in vitro transcription was carried out in the absence of UTP. Surprisingly, the upper band disappeared from the gel and the transcript did not induce any IFN-α induction from purified primary human monocytes (FIG. 7A-C, sample 5, "ivt3P-G_ACA-U").

The addition of a synthetic complementary strand (AS G21) to such an in vitro transcribed single-strand RNA oligonucleotide (ivt3P-G_ACA-U) which by itself has no IFN-inducing activity restored the IFN-inducing activity (FIG. 1A-C, sample 6, "ivt3P-G_ACA-U+AS G21").

This result suggests that it is possible to obtain an ssRNA without double strand formation and without IFN-inducing activity from in vitro transcription. Such an in vitro transcribed ssRNA can become an active RIG-I ligand only upon double strand formation with a complementary strand.

Example 5. The Effect of 2'-O-Methylation on the IFN-α-Inducing Activity of a Blunt Ended RNA Olignucleotide Bearing 5' Triphosphate is Position-Dependent Monocytes were purified from healthy donors and stimulated with 0.8 μg/ml of the indicated double-stranded oligonucleotides (FIG. 8) complexed with 2 μl of Lipofectamine. The strand with the 5' triphosphate-bearing 5' A (i.e., 3P-A) is hereinafter referred to as the "sense strand" and its complementary strand (AS A24 with and without modifications), the "antisense strand".

2'-O-methylation of U at various positions, positions 2, 4, 12 and 20 from the 3' end, in the antisense strand decreased the IFN-α-inducing activity of the double-stranded 3P oligonucleotide (FIG. 8). The observation appears consistent with previous report that nucleoside modifications which occur during eukaryotic post-transcriptional RNA processing abrogated the IFN-inducing activity of RNA oligonucleotides[15, 19]. The activity-decreasing effect was most the pronounced when the 2'-O-methylation occurred at position 2 from the 3' end of the antisense strand.

Surprisingly, the most 3' U of the antisense strand was 2'-O-methylated, the IFN-inducing activity of the double-stranded olignucleotide was not only not reduced, but enhanced approximately 20% (FIG. 8).

These results suggest the possibility of modulating the IFN-inducing activity of a 3P oligonucleotide by 2'-O-methylation at specific positions. Whereas the IFN-inducing activity of a 3P olignucleotide may be enhanced by 2'-O-methylation of a most 3' nucleotide which base pairs with a most 5' ribonucleotide bearing a 5' triphosphate at a blunt end, the IFN-inducing activity may be reduced by 2'-O-methylation of any other nucleotide, especially the second most 3' nucleotide which is just 5' of the most 3' nucleotide which base pairs with a most 5' ribonucleotide bearing a 5' triphosphate at a blunt end.

Example 6. Molecular Motifs Recognized by and Activating RIG-I

Materials and Methods

Chemical Synthesis of Triphosphate Oligoribonucleotides

Oligoribonucleotides containing a free 5'-OH terminus were synthesized on an ABI 392 synthesizer using commercial 5'-Silyl 2'ACE protected amidites from Dharmacon. Solid phase triphosphorylation was performed using an improved version of the protocol developed by Ludwig and Eckstein[27]. End products were precipitated as sodium salt from Ethanol. MALDI-ToF analysis was performed by Metabion (Martinsried, Germany).

Monophosphate RNA, Non-Modified RNA and In Vitro Transcribed RNA

Monophosphate RNA and non-modified RNA oligoribonucleotides (ORN) were synthesized by commercial providers (Metabion, Martinsried, Germany and Biomers, Ulm, Germany, respectively). The sequences are listed in Table 1. Ivt3P-G and Ivt3P-Gaca were generated by in vitro transcription (IVT) with a commercial In vitro T7-Transcription Kit (Epicentre). For generation of DNA template dependent in vitro transcribed RNA, the T7-promoter region CAGTAATAGGACTCACTATAG was hybridized with the promoter+template strand (Ivt3P-G:

```
3'-GTC ATT ATG CTG AGT GAT ATC TGT GTG TGT GTG TGT
GTG TGA AA-5';

Ivt3P-Gaca:
T-GTC ATT ATG CTG AGT GAT ATC TGT GTG TGT GTG TGT
GTG TGT GT-5';

IVT2:
3'-GTC ATT ATG CTG AGT GAT ATC TGC TGC TGC TGC TGC
TGC TGC TGC TGC TG-5')
``` and directly used as a template for the in vitro transcription reaction. For generation of ivt3P-G w/o U and ivt3P-Gaca w/o U the in vitro transcription was performed in the absence of UTP.

Cell Culture

Human PBMCs were isolated from whole human blood of healthy, voluntary donors by Ficoll-Hypaque density gradient centrifugation (Biochrom Berlin, Germany). Plasmacytoid dendritic cells (PDC) were positively depleted using magnetically labelled anti-CD304 antibody (Miltenyi Biotec). Untouched monocytes were obtained by negative depletion from PBMCs according to the manufacturers instructions (Human Monocyte Isolation Kit II, Miltenyi Biotec). Viability of all cells was above 95%, as determined by trypan blue exclusion. If not indicated otherwise, 400,000 cells (PBMCs) or 200,000 cells (monocytes) were cultured in 96-well plates for stimulation experiments. Cells were kept in RPMI 1640 containing 10% FCS, 1.5 mM L-glutamine, 100 U/ml penicillin and streptomycin 100 μg/ml. All compounds were tested for endotoxin contamination prior to use.

Detection of Cytokines

The amount of IFN-α production was determined using the IFN-α module set from Bender MedSystems (Vienna, Austria). The ELISA assay was performed according to the manufacturer's protocol. The concentration of cytokines was determined by the standard curve obtained using known amounts of recombinant cytokines.

Flow Cytometry

Cell purity was assessed by FACS analysis of cell surface antigens using a FACS LSRII (BD Biosciences, Heidelberg, Germany). Human monocytes were stained with antibody against CD14-FITC or CD14-APC and cell purity was between 83% and 99%. Human PDCs were positively labelled with antibody against CD123-PE, HLA-DR-PerCp and negatively for CD11c-APC and a cocktail to lineage markers (FITC). Antibodies were purchased from BD PharMingen. Data analysis was performed on viable cells using CellQuest (BD Biosciences) and Flowjo (Treestar).

Protein Purification and Analysis $(His_6)$-Flag-tagged RIG-I (HF-RIG-I) was transiently overexpressed in 293T cells and lysed in a CHAPS containing lysis buffer (150 mM NaCl, 50 mM Tris/HCl pH7,4, 2 mM $MgCl_2$, 1 mM DTT, 1% CHAPS) including protease inhibitor cocktail (Roche). The lysate was incubated over night at 4° C. with ANTI-FLAG beads (Sigma). Anti-FLAG beads were washed subsequently with lysis buffer and high salt wash buffer (300 mM NaCl, 50 mM Tris/HCl pH7,4, 5 mM MgCl$_2$, 1 mM DTT, 0.1% CHAPS). RIG-I-FLAG was eluted by addition of FLAG-peptide (300 ug/ml) solution to the beads. Purity of recombinant RIG-I was determined by SDS-PAGE separation and subsequent Coomassie blue stain (FIG. 4G).

ATPase Assay

The ATPase assay was performed in assay buffer (50 mM KCl, 55 mM HEPES (pH 7.0) 3 mM MgCl$_2$, 0.5 mM DTT, 0.1 mM ATP). In order to calculate EC50, the RNA was titrated in a range from 6 fM to 4 µM. After 30 min of incubation at 37° C., occurrence of ADP was measured using a very sensitive FRET based competitive immunoassay (HTRF® Transcreener™ ADP, Cisbio, Bedford, USA) according to the manufacturers protocol. FRET was measured using an EnVision® Multilabel Reader (PerkinElmer, Waltham, USA). In this assay, inhibition of FRET correlates with the concentration of ADP generated by ATPase activity of RIG-I. ADP concentrations were calculated from an ADP/ATP titration curve according to the manufacturers protocol.

AlphaScreen RIG-I-Binding Assay

The binding affinity of RNA for (His$_6$)FLAG-tagged RIG-I (HF-RIG-I) was determined as described[31, 32] by an amplified luminescent proximity homogenous assay (AlphaScreen; Perkin Elmer). In this assay purified HF-RIG-I was incubated with increasing concentrations of biotinylated RNA for 1 hour at 37° C. in buffer (50 mM Tris/pH7.4, 100 mM NaCl, 0.01% Tween20, 0.1% BSA) and subsequently incubated for 30 min at 25° C. with HF-RIG-I-binding Nickel Chelate acceptor beads (Perkin-Elmer) and biotin-RNA-binding Streptavidine donor beads (Perkin Elmer). The donor bead contains the photosensitizer phtalocyanine, which converts ambient oxygen into a 'singlet' oxygen after illumination with a 680-nm laser light. During the 4-s lifetime, the 'singlet' oxygen can diffuse up to 200 nm and activate a thioxane derivative on the acceptor bead that is brought into proximity by interaction of the test molecules bound to the beads. The resulting chemiluminescence with subsequent activation of a fluorochrome (contained within the same bead) emitting in the range of 520-620 nm correlates with the number and proximity of associated beads which is inversely correlated with the dissociation constant of donor (biotin-RNA) and acceptor (HF-RIG-I). The assay was performed in wells of 384-well plates (Proxiplate; Perkin-Elmer). Plates were analyzed for emitted fluorescence with a multilabel reader (Envision; Perkin Elmer).

Results

Figure 9:
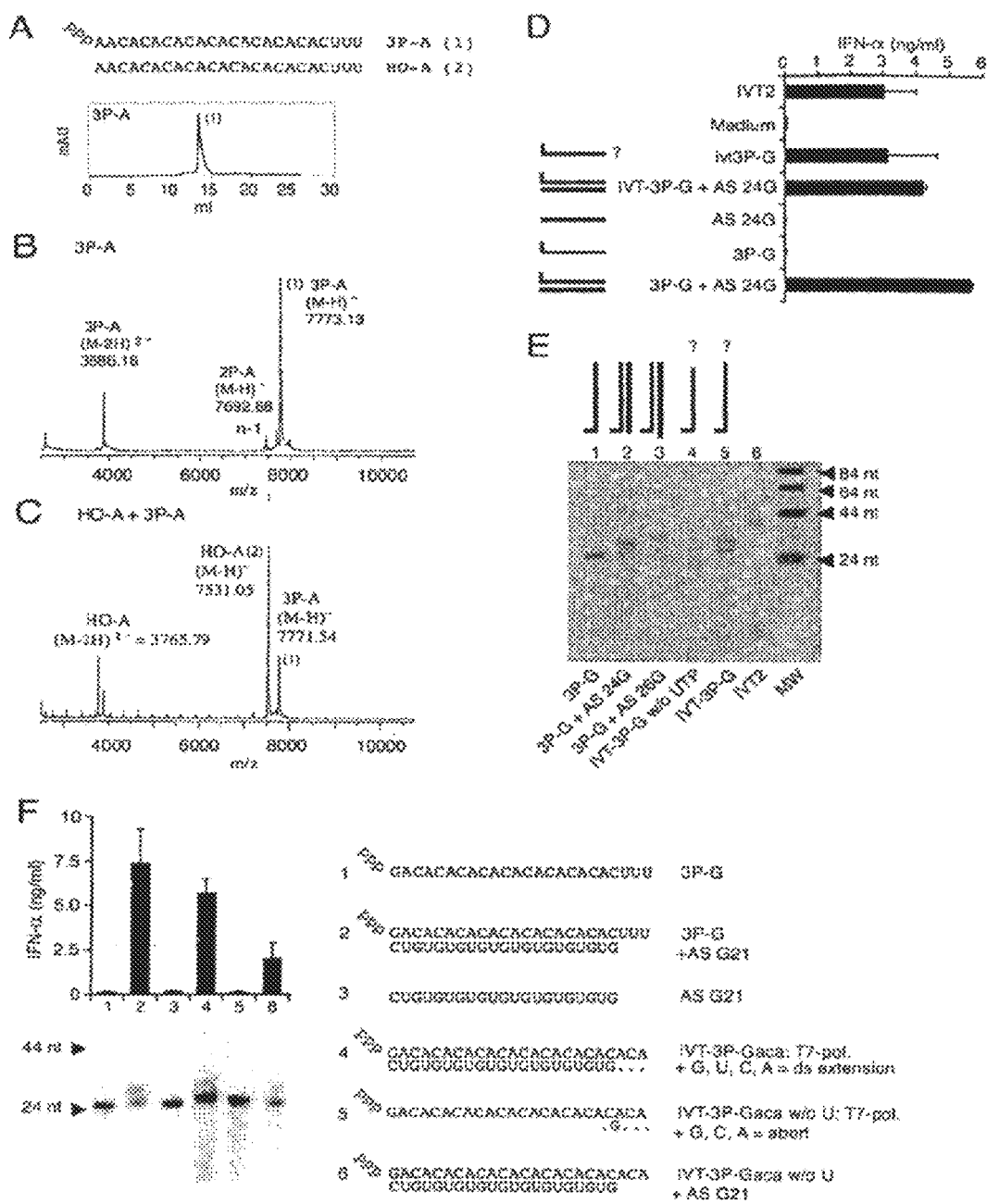
FIG. 9. Fully synthetic 5'triphosphate single strand RNA is not sufficient to activate RIG-I. (A) Reverse Phase HPLC analysis of 3P-A=pppAAC ACA CAC ACA CAC ACA CAC UUU (1) after deprotection under standard ACE deprotection conditions (pH=3.8, 60° C. in 30 min). (B) MALDI-ToF analysis of 3P-A: calculated molecular weight of 3P-A is 7770; the peak at 3886 represents the double charged anion peak (z=2). (C) MALDI-ToF analysis of 3P-A mixed with HO-A. The difference between the molecular weight of the product 3P-A (1) and the educt HO-A (2) is 240 which corresponds to the molecular weight of an additional triphosphate group ($H_3P_3O_9$). (D) Purified monocytes were stimulated with the indicated single strand or double strand synthetic or in vitro transcribed RNA oligonucleotide. The question mark indicates that the 3'end of this in vitro transcribed RNA is not molecularly defined. IFN-α production was analysed 24 hours after stimulation. Data from four independent donors are depicted as mean values±SEM. (E) Indicated RNA stimuli (see Table 5) were analysed on a denaturing 12% polyacrylamide gel (containing 50% urea w/v) and stained with methylene blue detecting single strand and double strand RNA. Ivt3P-G w/o U was generated by in vitro transcription in the absence of the nucleotide UTP. (F) Monocytes were stimulated with single and double strand RNA as indicated. RNAs were analysed on a denaturing 12% polyacrylamide gel (containing 50% urea w/v) and stained with methylene blue.

A 24mer RNA oligonucleotide with 5'-G (3P-G) was designed for which self-complementarity and thus secondary structure formation (intra- or intermolecular double strand formation) was predicted to be absent (see Table 5). A triphosphate group was covalently attached to the 5'end of the corresponding synthetic oligonucleotide by using a previously established method[27]. Purity of RNA oligonucleotides was confirmed using HPLC and MALDI-ToF (FIG. 9A-C). The same sequence (ivt3P-G) as well as a positive control oligonucleotide (IVT2, 30mer, Table 5) were generated by in vitro transcription. The RIG-I activity of RNA oligonucleotides was examined in primary human monocytes, a well-established assay for RIG-I activation[15].

TABLE 5

Oligonucleotide Sequences (5'->3')

| Name | Sequence | 5' end | Type | SEQ ID NO: |
|---|---|---|---|---|
| 3P-A | AACACACACACACACACACUUU | 3P | RNA, syn | 8 |
| ivt3P-G | GACACACACACACACACACUUU | 3P | RNA, ivt | 9 |
| ivt3P-Gaca | GACACACACACACACACACACA | 3P | RNA, ivt | 44 |
| 3P-G | GACACACACACACACACACUUU | 3P | RNA, syn | 9 |
| 3P-C | CACACACACACACACACACUUU | 3P | RNA, syn | 10 |
| 3P-U | UACACACACACACACACACUUU | 3P | RNA, syn | 11 |
| HO-A | AACACACACACACACACACUUU | OH | RNA, syn | 8 |
| P-A | AACACACACACACACACACUUU | P | RNA, syn | 8 |
| AS A34 | AAAGUGUGUGUGUGUGUGUGUUGUGUGUGU | OH | RNA, syn | 45 |
| AS A26 | AAAGUGUGUGUGUGUGUGUGUUGU | OH | RNA, syn | 12 |
| AS A25 | AAAGUGUGUGUGUGUGUGUGUUG | OH | RNA, syn | 13 |
| AS A24+2A | AAAAAGUGUGUGUGUGUGUGUGUU | OH | RNA, syn | 14 |
| AS A24+A | AAAAGUGUGUGUGUGUGUGUGUU | OH | RNA, syn | 15 |
| AS A24 | AAAGUGUGUGUGUGUGUGUGUU | OH* | RNA, syn | 16 |
| AS A24P | AAAGUGUGUGUGUGUGUGUGUU | OH** | RNA, syn | 16 |
| AS A23 | AAGUGUGUGUGUGUGUGUGUU | OH | RNA, syn | 17 |
| AS A21 | GUGUGUGUGUGUGUGUGUU | OH | RNA, syn | 18 |

TABLE 5-continued

Oligonucleotide Sequences (5'->3')

| Name | Sequence | 5' end | Type | SEQ ID NO: |
|---|---|---|---|---|
| AS A20 | UGUGUGUGUGUGUGUGUGUU | OH* | RNA, syn | 19 |
| AS A19 | GUGUGUGUGUGUGUGUGUU | OH | RNA, syn | 20 |
| AS G26 | AAAGUGUGUGUGUGUGUGUGUCGU | OH | RNA, syn | 24 |
| AS G25 | AAAGUGUGUGUGUGUGUGUGUCG | OH | RNA, syn | 25 |
| AS G24+2A | AAAAGUGUGUGUGUGUGUGUGUC | OH | RNA, syn | 26 |
| AS G24+A | AAAGUGUGUGUGUGUGUGUGUC | OH | RNA, syn | 27 |
| AS G24 | AAGUGUGUGUGUGUGUGUGUC | OH | RNA, syn | 28 |
| AS G23 | AGUGUGUGUGUGUGUGUGUC | OH | RNA, syn | 29 |
| AS G21 | GUGUGUGUGUGUGUGUGUC | OH | RNA, syn | 30 |
| AS G20 | UGUGUGUGUGUGUGUGUC | OH | RNA, syn | 31 |
| AS G19 | GUGUGUGUGUGUGUGUC | OH | RNA, syn | 32 |
| AS G17 | GUGUGUGUGUGUGUC | OH | RNA, syn | 33 |
| AS G15 | GUGUGUGUGUGUC | OH | RNA, syn | 34 |
| AS G13 | GUGUGUGUGUC | OH | RNA, syn | 35 |
| AS C26 | AAAGUGUGUGUGUGUGUGUGUGGU | OH | RNA, syn | 36 |
| AS C24 | AAAGUGUGUGUGUGUGUGUGUG | OH | RNA, syn | 37 |
| AS U26 | AAAGUGUGUGUGUGUGUGUGUAGU | OH | RNA, syn | 38 |
| AS U24 | AAAGUGUGUGUGUGUGUGUGUA | OH | RNA, syn | 39 |
| AS23 | AAAGUGUGUGUGUGUGUGUGU | OH* | RNA, syn | 40 |
| AS21 | AAAGUGUGUGUGUGUGUGU | OH | RNA, syn | 41 |
| AS19 | AAAGUGUGUGUGUGUGU | OH | RNA, syn | 42 |
| IVT2 | GACGACGACGACGACGACGACGACGAC | 3P | RNA, ivt | 43 |
| dAdT | (AT)$_{200-4000}$ | P | DNA | |
| ASGFP2 | AAGAUGAACUUCAGGGUCAGCGUC | OH | RNA, syn | 46 |
| ASGFP2 3'23 | AAGAUGAACUUCAGGGUCAGCGU | OH | RNA, syn | 47 |
| ASGFP2 3'21 | AAGAUGAACUUCAGGGUCAGC | OH | RNA, syn | 48 |
| ASGFP2 3'19 | AAGAUGAACUUCAGGGUCA | OH | RNA, syn | 49 |
| ASGFP2 5'21 | AUGAACUUCAGGGUCAGCGUC | OH | RNA, syn | 50 |
| ASGFP2 5'19 | GAACUUCAGGGUCAGCGUC | OH | RNA, syn | 51 |
| 3P-GFP1 | GGGGCUGACCCUGAAGUUCAUCUU | 3P | RNA, syn | 52 |
| 3P-GFP2 | GACGCUGACCCUGAAGUUCAUCUU | 3P | RNA, syn | 53 |
| 3P-GFP3 | GGGGCGCUGACGCCCUGAAGUUCA | 3P | RNA, syn | 54 |
| TAK P25 | AAACUGAAAGGGAGAAGUGAAAGUG | P | RNA, syn | 55 |
| TAK 25P | AAACUGAAAGGGAGAAGUGAAAGUGAG | OH** | RNA, syn | 56 |
| TAK 25 | AAACUGAAAGGGAGAAGUGAAAGUG | OH | RNA, syn | 57 |
| TAK 25c | CACUUUCACUUCUCCCUUUCAGUUU | OH | RNA, syn | 58 |

3P = triphosphate, P = monophosphate, ivt = in vitro transcription; syn = synthetic
*Oligos used for alpha screen were labelled with biotin at the 5' end.
**AS A24P and TAK 25P were monophosphorylated at the 3' end.

As expected, the in vitro transcribed form of 3P-G and the positive control sequence IVT2 induced IFN-α in monocytes. Unexpectedly, synthetic 3P-G showed no IFN-α induction (FIG. 9D). Polyacrylamide gel analysis revealed that ivt3P-G presented as two major bands one of which ran slower than the single band of synthetic 3P-G (FIG. 9E, lane 5 versus lane 1). Since synthetic 3P-G is molecularly defined, ivt3P-G forms slower running bands either due to self complementarity or due to higher molecular weight. Self complementarity is unlikely to be present given the sequence that we used. However, the higher molecular weight could result from RNA template dependent RNA transcription that leads to complementary side products and to double-stranded RNA products from IVT reactions which where originally designed to be single stranded. Indeed, the addition of a fully synthetic complementary single strand (not containing a triphosphate group, AS G24) to 3P-G (3P-G+AS G24) led to full RIG-I ligand activity (FIG. 9D).

We then changed the sequence of 3P-G to 3P-Gaca by replacing the three 3'UUU to 3'ACA (see FIG. 9F right panel). The in vitro transcription of 3P-Gaca requires only three nucleotides G, C and A but not U in the in vitro reaction mix. Therefore, double strand formation can only occur in the presence of U. Consistent with the results obtained by using defined synthetic RNAs, we found that ivt3P-Gaca strongly induced IFN-α, while ivt3P-Gaca w/o U (absence of U in reaction mix, no double strand expected) showed no IFN-α induction (FIG. 9F). The addition of the 21mer complementary strand (AS G21) restored IFN-α inducing activity. The lack of double strand formation of ivt3P-Gaca w/o U was confirmed using gel analysis (FIG. 9F)

Figure 10:
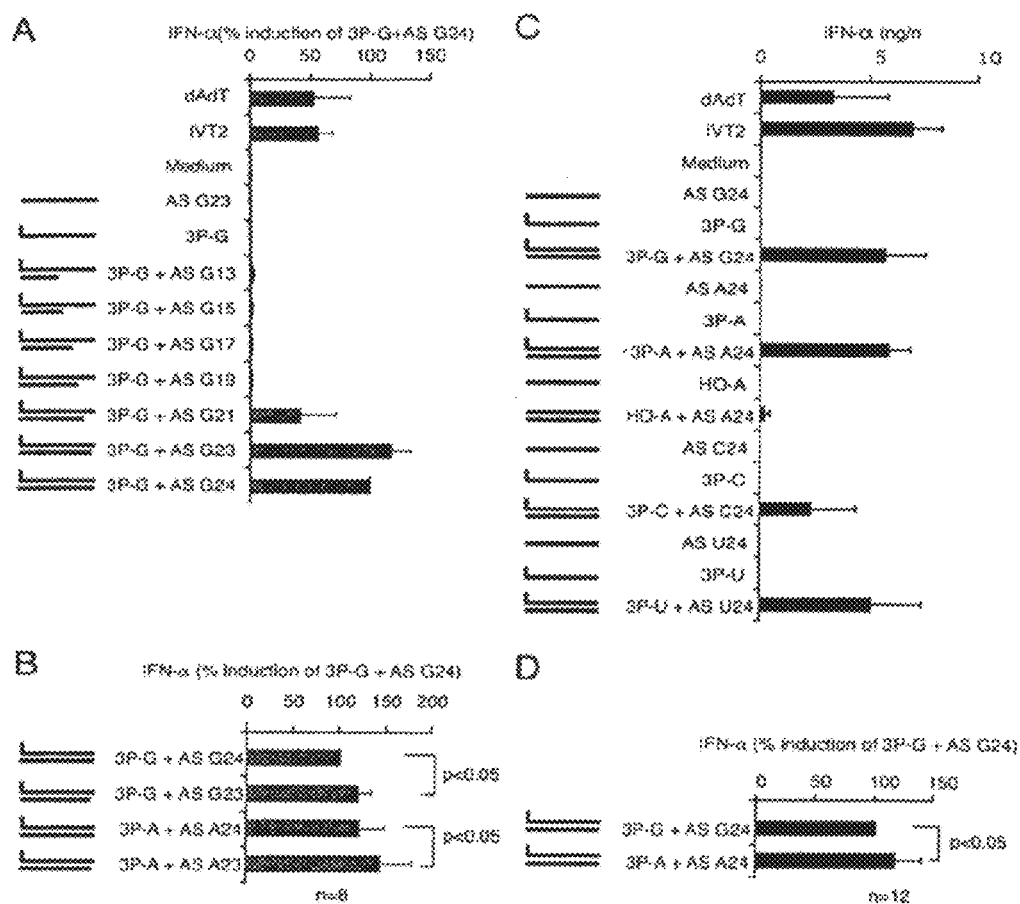
FIG. 10. RIG-I activation requires a short double strand of at least 21 base pairs and prefers 5'-adenine. Purified monocytes were stimulated with the indicated single strand or double strand synthetic RNA oligonucleotide. IFN-α production was analysed 24 hours after stimulation. Data from three or four (NC), eight (B) or twelve (C) independent donors are depicted as mean values±SEM. (A) 3P-A was hybridized with synthetic antisense single strand RNA with different lengths generating double strand RNA with blunt end carrying the triphosphate group. (B) 23mer (AS G23 and AS A23) with a blunt triphosphate end and a 3' overhang at the non-triphosphate end. (C) Comparison of RIG-I ligand activity of 3P-G to the other three synthetic variants (3P-A, 3P-C, 3P-U) which were hybridized with the corresponding synthetic 24mer (AS-A24, AS-C24, AS-U24) or used as single strands. (D) IFN-α inducing activity of 3P-A+AS A24 and 3P-G+AS G24.

Next the length of the strand complementary to 3P-G (AS G24) was decreased from 24 down to 13 nucleotides (3P-G with complementary AS G24 to AS G13, see FIG. 10A, and Table 5). We found that with the sequence 3P-G, AS G21 was the minimal tolerated length of a complementary strand (FIG. 10A). AS G23 together with 3P-G (one nucleotide 3' overhang at the non-triphosphate end) consistently showed higher activity than AS G24 (no overhang at the non-triphosphate end); the same was seen for AS A23 and AS A24 with 3P-A (FIG. 10B), suggesting that blunt end formation at the non-triphosphate end is not preferred.

To analyse the contribution of the 5'-nucleoside we compared the RIG-I ligand activity of 3P-G to the other three synthetic variants (3P-A, 3P-C, 3P-U). A preference for a 5'-adenosine compared to 5'-guanosine was observed (FIGS. 10C and 10D). Furthermore, elongation of the complementary strand at the non-triphosphate end for both 3P-G and 3P-A did not reduce but rather increased the IFN-α inducing activity (FIG. 11A).

Figure 11:
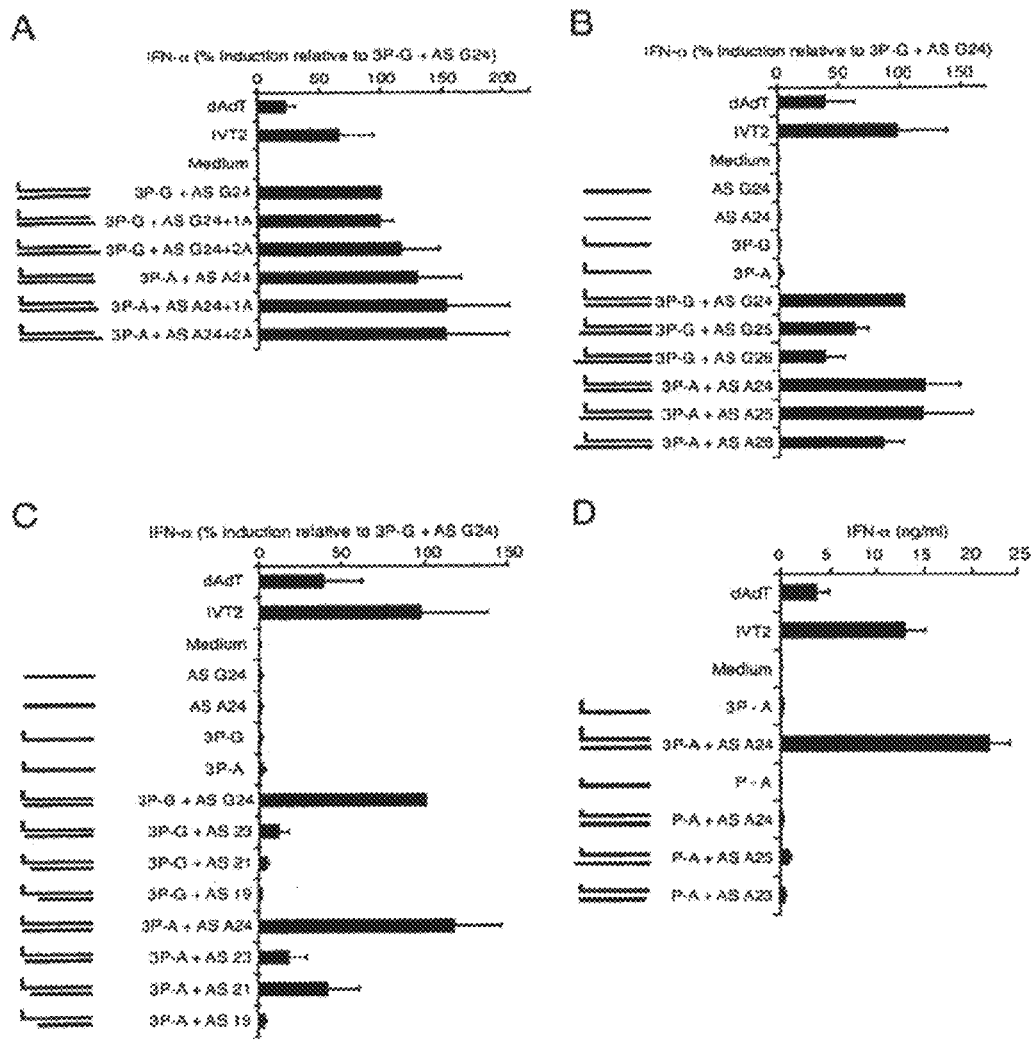
FIG. 11. Blunt end at the triphosphate end but not at the non-triphosphate end contributes to RIG-I ligand activity, and 5' monophosphate does not substitute for 5' triphosphate. Purified monocytes were stimulated with the indicated single strand or double strand synthetic RNA oligonucleotides. IFN-α production was analysed 24 hours after stimulation. Data from four independent donors are depicted as mean values±SEM. 3P-G and 3P-A were hybridized with corresponding antisense strands with different lengths and positions. (A) The use of 25mer (AS G24+A and AS A24+A) and 26mer (AS G24+2A and AS A24+2A) results in a mononucleotide or dinucleotide 5' overhang at the non-triphosphorylated end. (B) The use of 25mer (AS G25 and AS A25) and 26mer (AS G26 and AS A26) results in a mononucleotide or dinucleotide 3' overhang at the triphosphate end. (C) The use of 19mer, 21mer and 23mer single strand antisense RNA (AS19, AS21, AS23) results in a 5' overhang at the triphosphate end (−5 nt, −3 nt, −1 nt). (D) IFN-α-inducing activity of 5'monophosphate single strand RNA (P-A) and synthetic 5' triphosphate single strand RNA (3P-A) and combinations with complementary strands of different lengths are compared.
Figure 13:
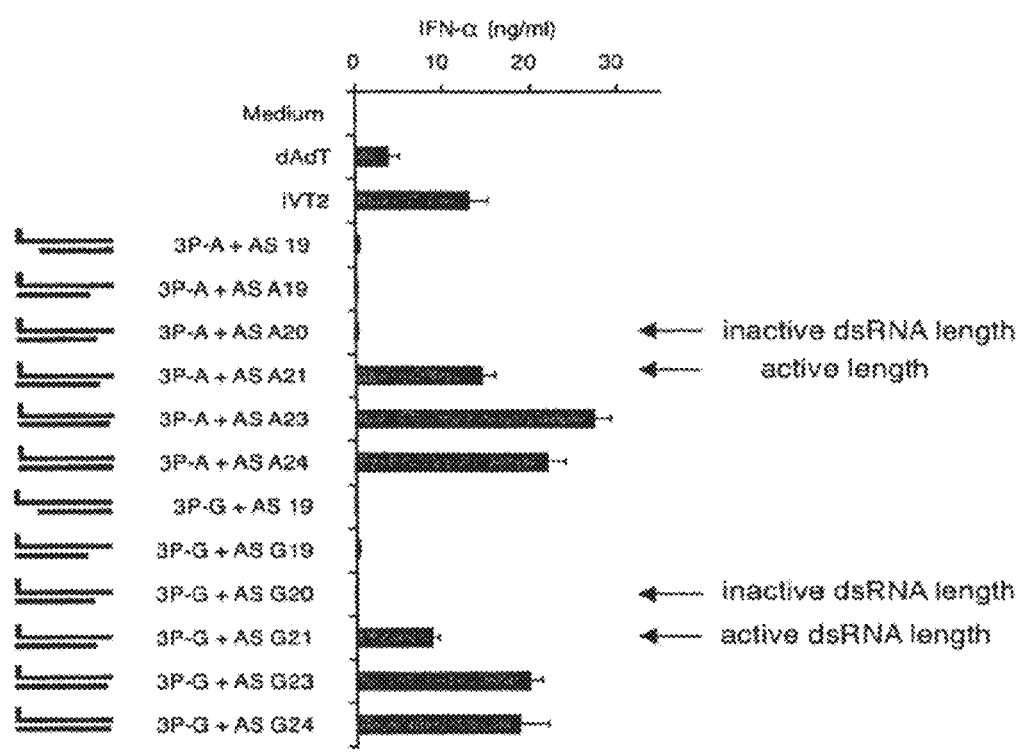
FIG. 13. Length and 5' and 3' overhang impact on IFN-α stimulating activity of short double strand RNA. Purified monocytes were stimulated with the indicated single strand or double strand synthetic RNA oligonucleotides. IFN-α production was analyzed 24 hours after stimulation. (A) 3P-G and 3P-A hybridized with antisense strands of different lengths and binding positions are compared. (B) 3P-A hybridized with an antisense strand resulting in a double strand RNA with a 10 base long 3 overhang at the triphosphate end.
Figure 13:
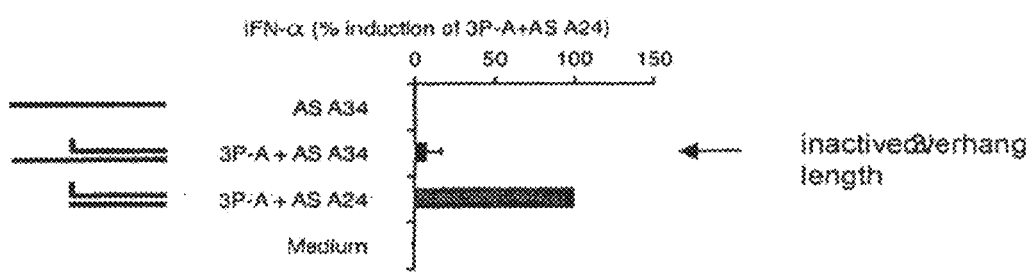
Figure 14:
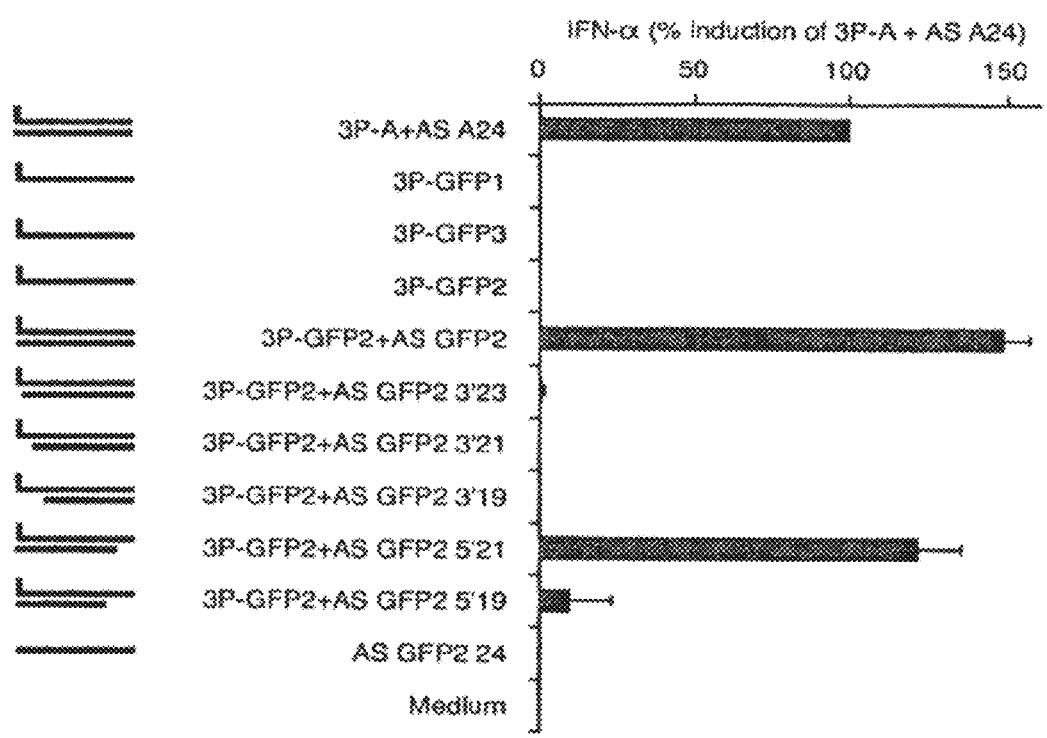
FIG. 14. Confirmation of structural requirements for RIG-I activation using an independent RNA sequence (GFP). Purified monocytes were stimulated with the indicated single strand or double strand synthetic RNA oligonucleotides (3P-GFP1, and variations thereof). IFN-α production was analyzed 24 hours after stimulation.

Unlike the non-triphosphate end, elongation at the triphosphate end reduced RIG-I ligand activity (FIGS. 11B and 13). RIG-I ligand activity was specifically sensitive to shortening of the complementary strand resulting in a 5' overhang at the triphosphate end (3P-G+AS 23, 3P-G+AS 21, 3P-G+AS 19, FIG. 11C). Identical results were seen with an unrelated RNA sequence (GFP2, see FIG. 14). The comparison of three related sequences, 3P-GFP1, 3P-GFP2 and 3P-GFP3, suggested that stem-loop secondary structure formation in a single strand RNA oligonucleotide is not sufficient for RIG-I activation (FIG. 14, sequences see Table 5).

Figure 15:
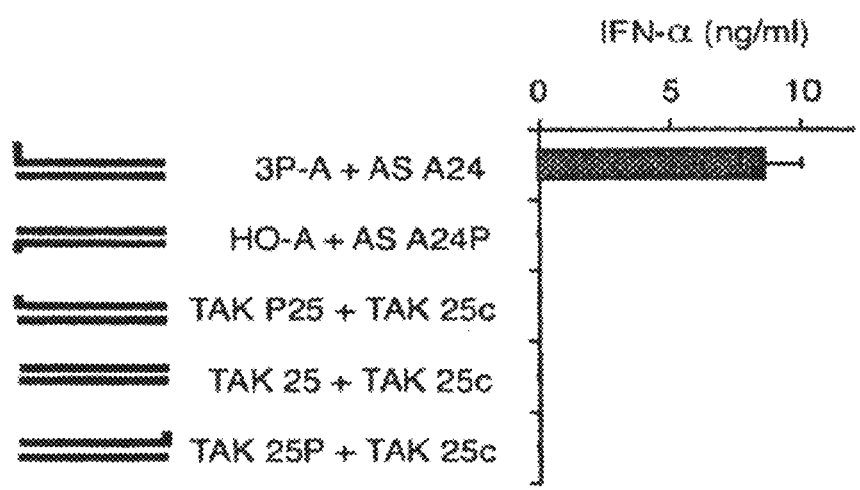
FIG. 15. 5'- and 3' monophosphate double strand RNA is not sufficient for IFN-α induction in human monocytes. Purified monocytes were stimulated for 24 hours with the indicated single-stranded or double-stranded synthetic RNA oligonucleotide, and IFN-α was analysed in the supernatants. Sequences are from Takahasi and colleagues[24].

Next we compared synthetic 5'monophosphate single strand RNA (P-A) to synthetic 5'riphosphate single strand RNA (3P-A) and varied the length of the complementary strand in order to study the contribution of blunt end and the length of the double strand portion (FIG. 11D). Compared to the 5'riphosphate version of the same sequence we found no considerable IFN-α induction by 5' monophosphate blunt end double strand RNA (P-A+AS A24). A one nucleotide 3' overhang at the monophosphate end (P-A+AS A25) or a one nucleotide 3' overhang of the monophosphate strand (P-A+AS A23) (FIG. 11D), or shortening the complementary strand down to 21 nucleotides (P-A+AS A21) did not increase RIG-I activity (data not shown). The same was seen for the RNA sequences of Takahasi and colleagues (FIG. 15)[24].

Figure 12:
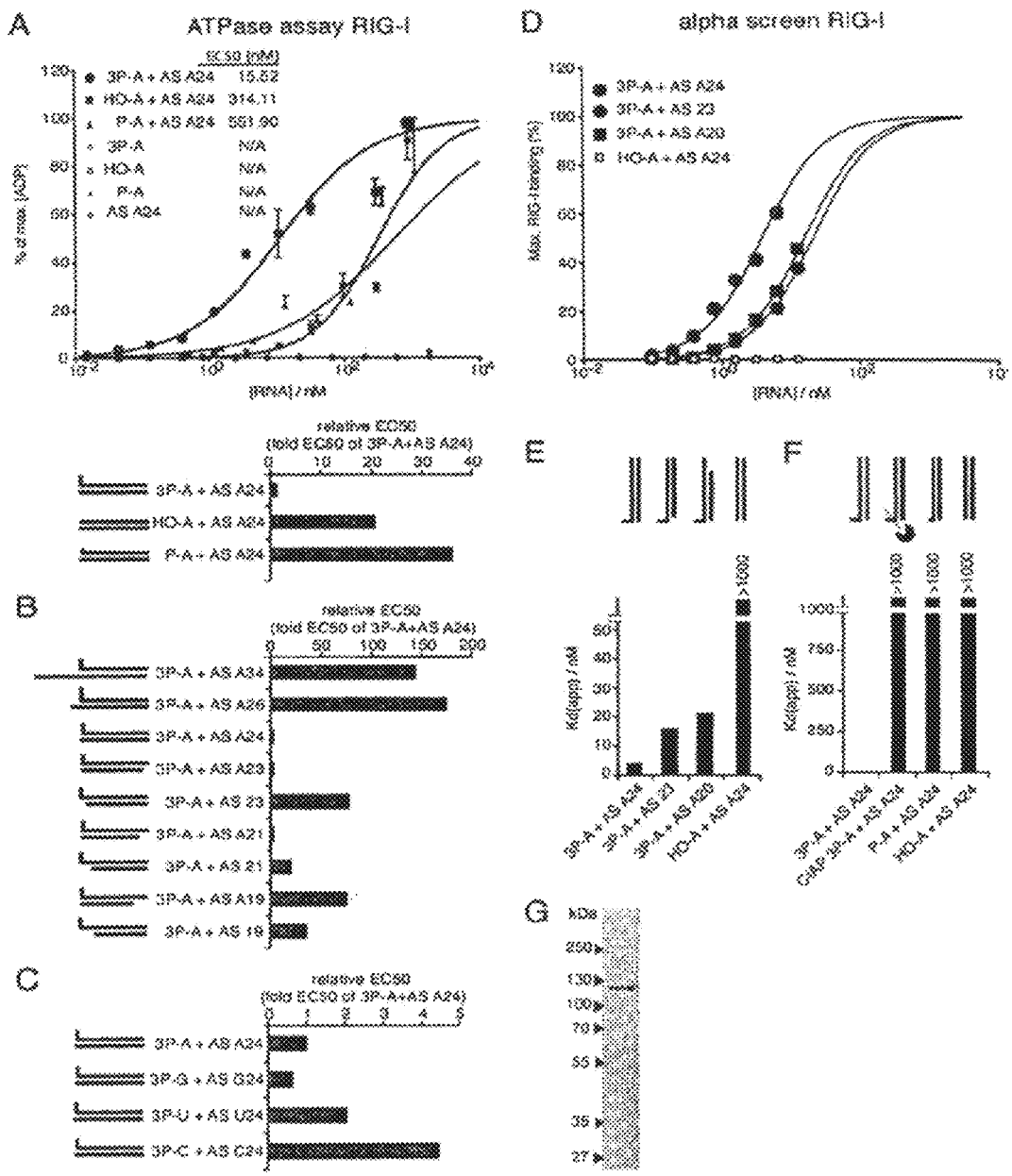
FIG. 12. IFN-α inducing activity of RIG-I RNA ligands correlates with RIG-I ATPase activity and with RIG-I binding affinity. (A) For the ATPase assay purified RIG-I protein was incubated with increasing amounts of indicated RNA molecules (from $10^{-9}$ nM to 1800 nM) and the release of ADP was analysed after 30 min at 37° C. by a FRET-based competitive immunoassay. The percentage of ADP release is plotted against the decadic logarithm of the concentration of indicated RNAs. Half effective concentration (EC50) was determined by statistical analysis (non-linear regression). Low EC50 represents high RIG-I ATPase activity. (B) The EC50 of the synthetic 3P-A hybridized with the indicated antisense RNAs are compared. (C) The EC50 of 5'triphosphate double strand RNA with different 5' bases (A, G, U, C) are compared. (D) Purified (His6)-tagged RIG-I was incubated with different RNA molecules bearing a biotin on the 5'end of the antisense strand (at the non-triphosphate end of the double strand RNA). (His6)-tagged RIG-I protein was bound to Ni-chelate beads (donor); biotinylated RNA was bound to streptavidine beads (acceptor). The resulting fluorescence correlates with the number and proximity of interacting donor-acceptor pairs. Concentration of indicated RNAs is plotted against the percentage of maximum binding to RIG-I. The dissociation constant Kd(app) is calculated by statistical analysis (non-linear regression). (E) and (F) Kd(app) of non-modified, monophosphate and triphosphate RNAs hybridized to indicated antisense RNAs of different lengths are compared. (F) CIAP 3P-A+AS A24 was incubated with active alkaline phosphatase; the other stimuli were incubated with heat-inactivated active alkaline phosphatase. (G) Purified (His6)-tagged RIG-I protein was analysed by SDS-PAGE and Coomassie Blue staining.

We analysed the direct interaction of purified human RIG-I protein isolated from HEK293T cells with different single strand and double strand RNA ligands. Single strand RNA (all open symbols) irrespectively of 5' triphosphate or 5' monophosphate did not induce ATPase activity (FIG. 12A). Double strand RNA molecules (all black symbols) showed an EC50 in the range of 15 nM to 600 nM depending on the composition of the double strand and the configuration of the 5'end (FIG. 12A). Double strand RNA with 5' monophosphate and without 5' phosphate (P–A+AS A24, HO–A+AS A24) showed a 35- and 20-fold higher EC50 (lower ATPase activity) than double strand RNA with a 5' triphosphate (FIG. 12A). The 5' riphosphate double strand RNA molecules which induced substantial amounts of IFN-α in monocytes (3P–A+AS A24, 3P–A+AS A23, 3P–A+AS A21, see FIG. 13) reached their EC50 at 20- to 150-fold lower concentrations than dsRNA ligands that weakly induced IFN-α (3P–A+AS A34, 3P–A+AS23, 3P–A+AS21, 3P–A+AS19, 3P–A+ASA19) (FIG. 12B, compare to FIGS. 13A and 13B). The ATPase activities of different 5' triphosphate RNAs with different 5' bases (3P–A+AS A24, 3P–G+AS G24, 3P–U+AS U24, 3P–C+AS C24, FIG. 12C) reflected the observed IFN-α inducing activity (A=G=U>C, compare FIG. 10A). These data demonstrate that the IFN-α inducing activity of RNA RIG-I ligands correlates with ATPase activity.

Using a homogenous ligand interaction assay we analysed the affinity of different RNA molecules to RIG-I, we found that binding of RNA to RIG-I strictly depended on the presence of a triphosphate at the 5' end (FIGS. 12D and 12E). The dissociation constant of 5'-triphosphate RNA (3P–A+AS A24) was approximately 4 nM. The Kd(app) of corresponding non-modified, 5'monophosphate RNA or dephosphorylated 3P-RNA (HO–A+AS A24, P–A+AS A24, 3P–A+AS A24 CIAP) was above the detection limit of this assay but at least 1000-fold higher than the Kd(app) of 5' triphosphate double strand RNA (FIGS. 12D, E & F). Consistent with IFN-α inducing activity in monocytes, the magnitude of binding of IFN-α inducing (3P–A+AS A24) and of non-IFN-α-inducing (3P–A+AS23, 3P–A+AS A20, compare FIG. 12C and FIG. 13) 5'-triphosphate RNA to RIG-I differed 4- to 5-fold (FIG. 12E).

Together these results demonstrate that i) 5'triphosphate single strand RNA is not sufficient for RIG-I activation, ii) the recognition of 5' triphosphate requires a double strand spanning at least 21 nucleotides encompassing the 5' nucleotide carrying the triphosphate, iii) a 3' overhang at the 5' triphosphate end decreases and any 5' overhang at the 5'triphosphate end abolishes the activity, and iv) adenosine is the preferred nucleoside carrying the triphosphate. Furthermore, the replacement of 5' triphosphate by 5'monophosphate without results in a substantial loss of IFN-α inducing activity.

It was reported that double strand RNA is not only present in double strand RNA viruses but substantial amounts of cytosolic double strand RNA are also produced during the replicative life cycle of positive single strand RNA viruses[33]. In agreement with the requirement of double strand RNA for RIG-I recognition, double strand and positive single strand RNA viruses indeed present ligands for RIG-I[10, 34]. However, at first sight, this seemed less clear for RIG-I-mediated detection of negative single strand RNA viruses[1, 34] for which no double strand RNA can be detected[25, 33] but still viral genomic single strand RNA activates RIG-I[15, 25]. However, the antibody used to demonstrate the absence of double strand RNA[25, 33] is limited to the detection of double strand RNA longer than 40 bases[35]. Performing a careful analysis of sequence data we noted that genomes of negative strand viruses known to activate RIG-I contain 5' and 3' sequences that form a short double strand with a perfect blunt end and a 5' adenosine carrying the triphosphate group (FIG. 16). Such panhandle structures[36] serve as a RNA transcription initiation site for the viral RNA polymerase complex and were extensively studied for the influenza virus[37].

Example 7. Bcl-2 Silencing and Anti-Tumor Activity

Material and Methods
1. Cell Lines

Murine B16 melanoma cells ($H-2^b$), C26 adenocarcinoma cells ($H-2^d$), NIH-3T3 fibroblasts and primary murine embryonal fibroblasts (MEF) were cultivated in Dulbecco's modified Eagle's medium (Biochrom, Berlin, Germany) supplemented with 10% heat-inactivated fetal calf serum (FCS, Invitrogen Life Technologies), 2 mM L-glutamine, 100 U ml$^{-1}$ penicillin, 100 µg ml$^{-1}$ streptomycin and 10 mM β-mercaptoethanol (all from Sigma-Aldrich). The human melanoma cell line 1205 Lu (M. Herlyn, Wistar Institute, Philadelphia, Pa., USA) was cultured in MCDB153 (Sigma) with 20% Leibovitz's L-15 (PAA Laboratories), 2% FCS (PAA Laboratories), 1.68 mM $CaCl_2$ (Sigma) and 5 µg ml$^{-1}$ insulin (Sigma).

2. Culture of Primary Cells

Murine primary cells were cultivated in VLE RPMI 1640 (Biochrom) supplemented with 10% FCS, 3 mM L-Glutamine, 100 µg streptomycin, 100 U/ml penicillin and 10 mM β-mercaptoethanol. Plasmacytoid DC (pDC) from Flt3-ligand-induced (Flt3-L) bone marrow cultures were sorted with B220 microbeads (Miltenyi Biotec). Conventional dendritic cells (cDC) were generated as described[15]. For some experiments B cells were isolated from spleens of wild-type mice by MACS using CD19 microbeads (Milteny Biotec). Untouched NK cells and T cells were sorted from spleens using the NK cell isolation and the CD4 T Cell Isolation Kit (Milteny Biotec). Viability of all cells was above 95%, as determined by trypan blue exclusion and purity was >90% as analyzed by FACS.

3. RNAs

Chemically synthesized RNA oligonucleotides were purchased from Eurogentec (Leiden, Belgium) or MWG-BIOTECH AG (Ebersberg, Germany). For a detailed list of all chemically synthesized RNA oligonucleotides used for this experiment see Table 7. In some experiments single-stranded polyriboadenosinic acid (PolyA) or non-silencing control siRNAs were used as control-RNAs (indicated in Table 7). In vitro transcribed RNAs were synthesized as described[15]. For a detailed list of all in vitro transcription templates see Table 8.

TABLE 7

Figure 17:
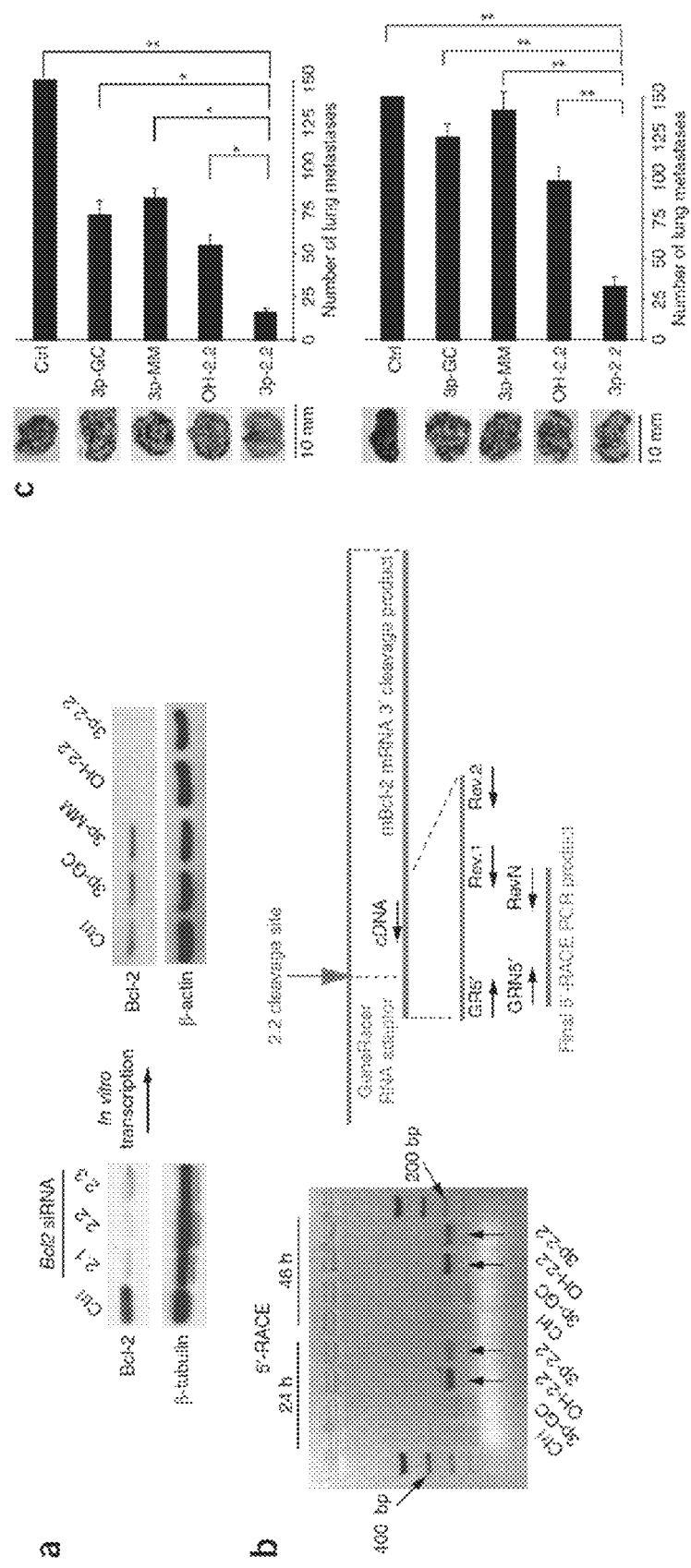
FIG. 17. 3p-2.2 siRNA potently silences Bcl-2 expression and reduces metastatic growth of B16 melanoma cells in the lungs.
(a) Left panel: Western blot analysis of Bcl-2 protein expression in B16 cells 48 h after transfection with the chemically synthesized siRNAs anti-Bcl-2 2.1, anti-Bcl-2 2.2 and anti-Bcl-2 2.3. A non-silencing siRNA (control RNA=Ctrl.) served as negative control. Right panel: Western blot analysis of Bcl-2 protein expression in B16 cells 48 h after transfection with the indicated in vitro transcribed anti-Bcl-2 3p-siRNA-2.2 (3p-2.2), The 3p-siRNAs 3p-GC and mismatch 3p-MM served as negative controls. One representative experiment of four is shown. (b) Left panel: In vitro 5'-RACE analysis of RNA extracted from B16 cells 24 h after treatment with the indicated RNAs. Black arrows mark the 5'-RACE-PCR amplification product showing the predicted product of RNA-interference (334 nt expected size). Right panel: schematic diagram showing the position of the predicted siBcl-2 cleavage site relative to nested primers used for PCR amplification of the cleavage fragment. (c) Intravenous challenge of C57BL/6 mice with B16 melanoma cells and treatment with 50 μg of the indicated siRNAs intravenously on days 3, 6, and 9. The mean number of macroscopically visible melanoma metastases on the lung surfaces of each group (±SEM) are shown after 12 (left panel) or 17 days (right panel) are shown. ($P^*<0.05$ or $P^{**}<0.01$; Mann-Whitney U test).
Figure 18:
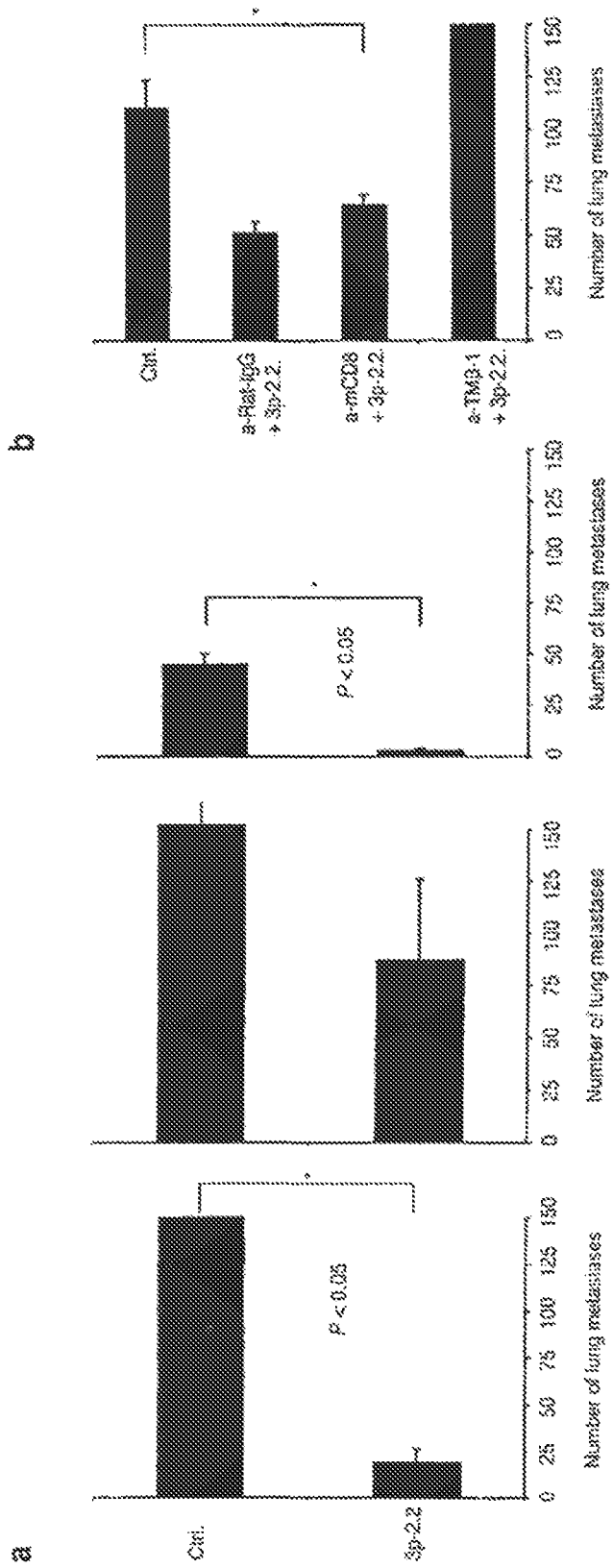
FIG. 18. Activation of type I IFNs and NK cells are necessary for the anti-tumor activity of Bcl-2-specific immunostimulatory 3p-siRNA in vivo
(a) Intravenous challenge of wild-type (WT), IFN-α-receptor 1-deficient (IFNAR$^{-/-}$) or toll-like receptor 7-deficient (TLR7$^{-/-}$) C57BL/6 mice with B16 melanoma cells and treatment with 50 μg of the indicated siRNAs intravenously on days 3, 6, and 9. The mean number of macroscopically visible melanoma metastases on the lung surfaces of each group (±SEM) are shown. Left panel: $P^*<0.05$ between 3p-2.2 and control RNA-treated in WT mice; n=4; Mann-Whitney U test; Middle panel: $P^*>0.05$ between 3p-2.2 and control RNA-treated IFNAR$^{-/-}$ mice (n=4); Right panel: $P^*<0.05$ between 3p-2.2 and control RNA-treated TLR7$^{-/-}$ mice (n=4) (b) Effect of antibody-based depletion of CD8 T cells (anti-mCD8), NK cells (anti-TMβ1) or control antibody (anti-Rat-IgG) on the therapeutic anti-tumor efficacy of 3p-2.2 in C57BL/6 wildtype mice ($P^*<0.05$; n=5).
Figure 19:
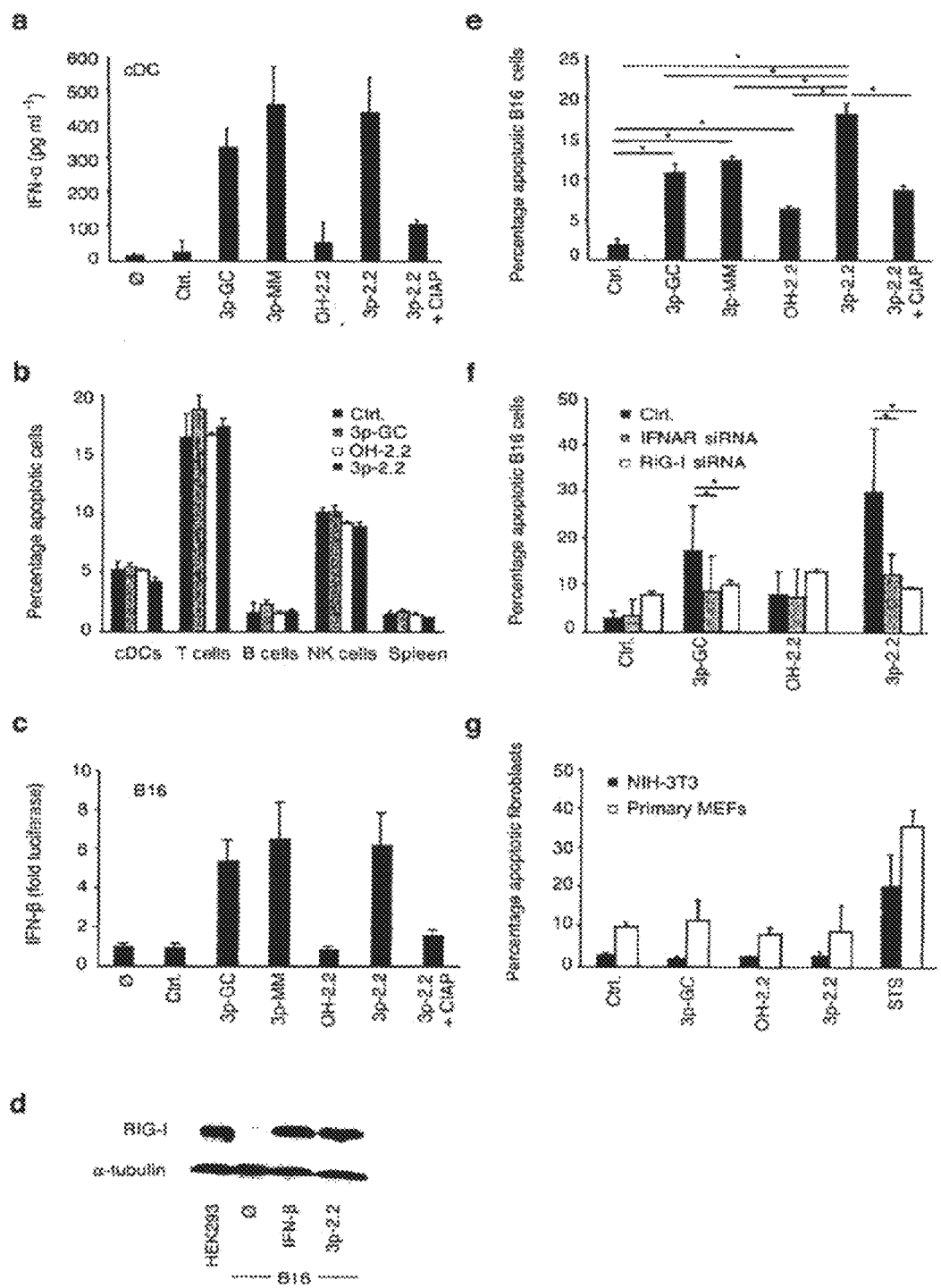
FIG. 19. Bcl-2-specific immunostimulatory 3p-siRNA induces cell-type specific innate immune responses and apoptosis in vitro
(a) Levels of IFN-α in the culture supernatant of conventional dendritic cells (cDC) measured by ELISA 24 h after transfection with the indicated RNAs. Data are shown as means±SEM of two independent experiments. (b) Flow cytometric analysis of apoptosis induction in cultured cDCs and freshly isolated B cells, T cells, NK cells and whole spleen cells 48 h after transfection with the indicated RNAs. Results are shown as mean±SEM of two independent experiments. (c) Analysis of IFN-β promoter activation in B16 cells 24 h after transfection with the indicated RNAs. Results of luciferase measurements are shown as mean±SEM. (d) Western blot analysis of RIG-I expression in B16 cells 8 h after treatment with 3p-2.2 (1 μg/ml) or murine IFN-β (1,000 U ml$^{-1}$). HEK293 cells overexpressing RIG-I served as positive control. (e) Flow cytometric analysis of apoptosis induction in B16 cells 48 h after transfection with the indicated RNAs. Results are shown as mean±SEM of four independent experiments ($P^*<0.05$; t-test) (f) Flow cytometric analysis of apoptosis induction in B16 cells 48 h after cotransfection with the indicated RNAs in combination with siRNA for IFNAR or RIG-I. Data are shown as mean±SEM of three independent experiments ($P^*<0.05$; t-test). (g) Flow cytometric analysis of apoptosis induction in primary murine embryonal fibroblasts (MEFs) and immortalized murine fibroblasts (NIH-3T3) treated as indicated. Exposure to staurosporine served as a positive control.
Figure 20:
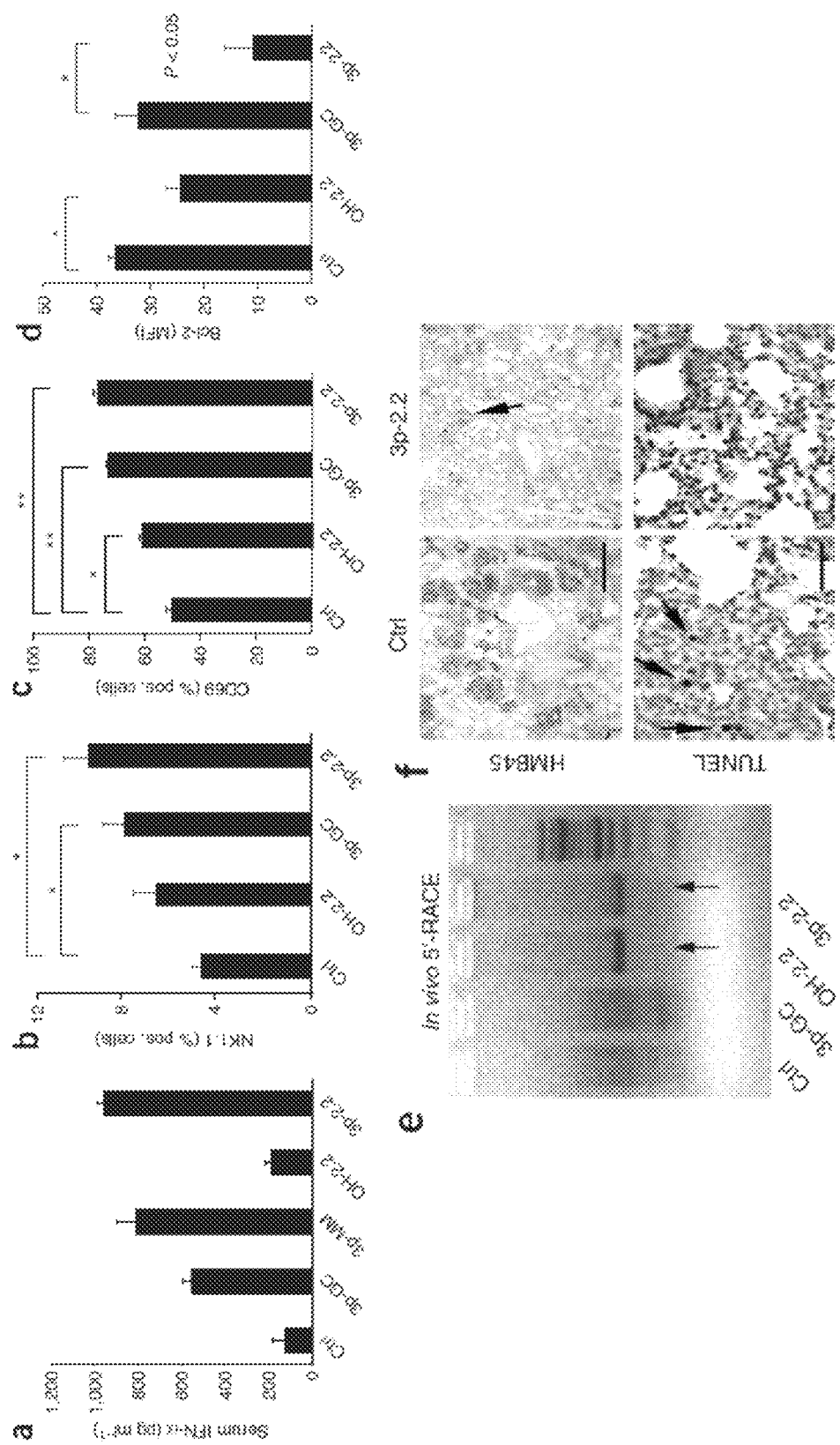
FIG. 20. Bcl-2-specific gene silencing and activation of the innate immune system synergistically promotes tumor cell apoptosis in vivo
(a) Serum IFN-α levels in mice measured by ELISA 6 h after injection of tumor-bearing mice with the indicated siRNAs. Data are shown as mean±SEM of four mice per group. (b) Flow cytometric analysis of NK cells in single cell suspensions of metastatic lungs. Results are presented as mean numbers of NK-1.1 positive cells±SEM ($P^*<0.05$ between 3p-2.2 and control RNA-treated mice; $P^*<0.05$ between 3p-GC and control RNA-treated mice; n=4). (c) Flow cytometric analysis of NK cell activation in single cell suspensions of metastatic lungs. Results are presented as mean percentage of CD69+ of NK1.1+ cells±SEM ($P^*<0.05$ between OH-2.2 and control RNA-treated mice; $P^{**}<0.01$ between 3p-2.2, 3p-GC and control RNA treated mice; n=4; t-test). (d) Quantification of Bcl-2 protein expression in HMB45+B16 tumor cells derived from single cell suspensions of metastatic lungs. Depicted is the mean fluorescence intensity (MFI)±SEM ($P^*<0.05$ between 3p-2.2 and 3p-GC-treated mice; $P^*<0.05$ between OH-2.2 and control RNA-treated mice; n=4; t-test). (e) In vivo 5'-RACE analysis of RNA extracted from metastatic lungs. (f) Upper panel: Immunohistochemical visualization of melanoma cells in lung tissue sections of tumor-bearing mice (black arrows). Lower panel: Detection of apoptotic cells within metastases by TUNEL staining (black arrows). Representative sections of one experiment with five mice/group are shown.

| Chemically synthesized siRNA sequences | | |
|---|---|---|
| Name | Type | Sequence 5'->3 |
| Murine Bcl-2 2.1 sense | RNA | AUGCCUUUGUGGAACUAUA |
| Murine Bcl-2 2.1 anti-sense | RNA | UAUAGUUCCACAAAGGCAU |
| Murine Bcl-2 2.2 sense | RNA | GCAUGCGACCUCUGUUUGA |
| Murine Bcl-2 2.2 anti-sense | RNA | UCAAACAGAGGUCGCAUGC |
| Murine Bcl-2 2.3 sense | RNA | GGAUGACUGAGUACCUGAA |
| Murine Bcl-2 2.3 anti-sense | RNA | UUCAGGUACUCAGUCAUCC |
| PolyA (used in FIG. 18a-d; FIG. 20b-d; FIG. 20f) | RNA | AAAAAAAAAAAAAAAAAAA |
| Murine RIG-I sense | RNA | GAAGCGUCUUCUAAUAAUU |
| Murine RIG-I anti-sense | RNA | AAUUAUUAGAAGACGCUUC |
| Control siRNAsense (used in FIG. 17 a, b, c; FIG. 19 a-c and FIG. 19 e-g, FIG. 20a and 20e; FIG. 21a-e; FIG. 22a-e) | RNA | UUCUCCGAACGUGUCACGU |
| Control siRNA anti-sense (see above) | RNA | ACGUGACACGUUCGGAGAA |
| Murine Bcl-2 2.4 sense | RNA | GGAGAACAGGGUAUGAUAA |
| Murine Bcl-2 2.4 anti-sense | RNA | CCUCUUGUCCCAUACUAUU |
| Human Bcl-2 h2.2 sense | RNA | GCAUGCGGCCUCUGUUUGA |
| Human Bcl-2 h2.2 anti-sense | RNA | CGUACGCCGGAGACAAACU |

TABLE 7-continued

Chemically synthesized siRNA sequences

| Name | Type | Sequence 5'->3 |
|---|---|---|
| IFNAR sense | RNA | TGGAAGCCGTTCAGATAAA |
| IFNAR anti-sense | RNA | TTTATCTGAACGGCTTCCA |

TABLE 8

DNA-oligonucleotides (templates) for in vitro transcription

| Name | Type | Sequence 5'->3 |
|---|---|---|
| Murine Bcl-2 2.2 sense | DNA | TCAAACAGAGGTCGCATGCCTATAGTGAGTCG |
| Murine Bcl-2 2.2 anti-sense | DNA | GCATGCGACCTCTGTTTGACTATAGTGAGTCG |
| GC sense | DNA | GGCGCCCCGCCGCGCCCCGCTATAGTGAGTCG |
| GC anti-sense | DNA | GCGGGGCGCGGCGGGGCGCCTATAGTGAGTCG |
| Murine Bcl-2 2.4 sense | DNA | TTATCATACCCTGTTCTCCCTATAGTGAGTCG |
| Murine Bcl-2 2.4 anti-sense | DNA | GGAGAACAGGGTATGATAACTATAGTGAGTCG |
| Human Bcl-2 h2.2 sense | DNA | TCAAACAGAGGCCGCATGCCTATAGTGAGTCG |
| Human Bcl-2 h2.2 anti-sense | DNA | GCATGCGGCCTCTGTTTGACTATAGTGAGTCG |
| Murine Bcl-2 mismatch sense (3p-MM) | DNA | TCAAACAGTCCTCGCATGCCTATAGTGAGTCG |
| Murine Bcl-2 mismatch (3p-MM) anti-sense | DNA | GCATGCGAGGACTGTTTGACTATAGTGAGTCG |

4. Transfection of RNA In Vitro

We transfected melanoma cells at a conflueny of 50-70% for 24 h with RNAs (1 μg ml$^{-1}$), using Lipofectamine 2000 or Lipofectamine RNAiMAX (both Invitrogen) according to the manufacturer's protocol. We transfected DC and immune cell subsets with 200 ng of nucleic acid with 0.5 μl of Lipofectamine in a volume of 200 μl.

5. Plasmids

IFN-β-Luc reporter plasmids, wild-type pPME-myc NS3-4A (NS3-4A), pPME-myc MutNS3-4A (NS3-4A*; containing an inactivating Serin 139 to Ala mutation) were kindly provided by T. Maniatis and J. Chen. RIG-I and the empty control vector were kindly provided by T. Fujita[11]. The renilla-luciferase transfection efficiency vector (phRLTK) was purchased from Promega. cDNA encoding WT murine Bcl-2 (mBcl-2/pcDNA) was provided by Christoph Borner (Institute of Molecular Medicine and Cell Research, Albert-Ludwigs-University of Freiburg, Germany)

6. In Vitro and In Vivo RACE

We purified total RNA of B16 cells (in vitro) or from pooled metastatic lung tissue using Tryzol reagent (Invitrogen) and the RNeasy purification procedure (QIAGEN). 5 μg of RNA from pooled samples was directly ligated to GeneRacer adaptor[AP1] (Invitrogen; 5'-CGACUGGAG-CACGAGGACACUGACAUGGACUGAAGGAGUA-GAAA). Ligated RNA was reverse transcribed using a gene-specific primer (Table 9). To detect cleavage product, we performed 2 rounds of consecutive PCR using primers complementary to the RNA adaptor and mBcl2 mRNA (GR5' and Rev 1 or Rev 2 for the 1$^{st}$ PCR round; GRN5' and RevN—for the nested PCR). For a detailed list of all the primers used for 5'-RACE see Table 9. We confirmed the identity of specific cleavage products by cloning of the PCR product and sequencing of individual clones.

TABLE 9

Primers used for 5'-RACE

| Name | Application | Sequence 5'-3' |
|---|---|---|
| cDNA | cDNA synthesis | GTTCATCTGAAGTTTCCAGCCTTTG |
| GR 5' | 5'RACE product forward per primer, 1st round | CGACTGGAGCACGAGGACACTGA |
| GRN 5' | 5'RACE product forward per primer, nested round | GGACACTGACATGGACTGAAGGAGTA |

TABLE 9-continued

Primers used for 5'-RACE

| Name | Application | Sequence 5'-3' |
|---|---|---|
| Rev.1 | 5'RACE product reverse per primer, 1st round, in vivo samples assay | TCCCTTTGGCAGTAAATAGCTGATTCGACCAT |
| Rev.2 | 5'RACE product reverse per primer, 1st round, in vitro samples assay | AAGTCCCTTCTCCAGTCCATGGAAGACCAG |
| RevN | 5'RACE product reverse per primer, nested round | CTTTGGCAGTAAATAGCTGATTCGACCATTTGC |

7. Western Blotting

We lysed cells in a buffer containing 50 mM Tris; pH 7.4, 0.25M NaCl, 1 mM EDTA, 0.1% Triton X-100, 0.1 mM EGTA, 5 mM $Na_3VO_4$, 50 mM NaF and protease inhibitors (Complete, Mini, EDTA-free, Roche), separated samples by SDS-PAGE and transferred them to a nitrocellulose membrane (Amersham-Biosciences) by semi-dry electroblotting. Antibodies specific for RIG-I, Bcl-2 (Santa Cruz, sc-7382), Mcl-1, Bcl-xL, Bim and Puma (all Cell Signaling Technology) were incubated at 4° C. over night and detected via a peroxidase-conjugated anti-rat or anti-rabbit secondary antibody (Amersham-Biosciences). Bands were visualized by chemiluminescence (ECL Kit; Amersham-Biosciences).

8. Mice and In Vivo Treatment with RNAs

RIG-I-, MDA-5-, TLR7-, IFNAR-deficient mice and CD11c-DTR mice were established as described[3,10,55,56]. The TLR7- and IFNAR-deficient mice used for tumor challenge experiments were crossed into the C57BL/6 genetic background for at least 10 generations. HGF/CDK4$^{R24C}$ mice were bred as described[57]. Mice were treated intravenously with RNAs after complexation with jetPEI according to the manufacturer's protocol. Briefly, for each mouse we mixed 10 µl of in vivo jetPEI with 50 µg of nucleic acids (N:P ratio of 10/1) in a volume of 200 µl 5% glucose solution and incubated for 15 min. We collected serum for cytokine measurements was after 6 h. For systemic DC depletion, we injected CD11c-DTR transgenic mice intraperitoneally with 100 ng of diphtheria-toxin (DT) in PBS (Sigma D-0564). We treated mice with jePEI-complexed RNAs 24 hr after DT-injection. We confirmed CD11c+ depletion by flow cytometry.

9. Induction of B16 Melanoma Lung Metastases and Lymphocyte Depletion

We experimental induced lung metastases by injection of $4 \times 10^5$ B16 melanoma cells into the tail vein. For tumor treatment we adminstered 50 µg of RNA complexed with jetPEI in a volume of 200µl on day 3, 6 and 9 after tumor cell challenge by retro-orbital or tail vein injection. 14 days after challenge we counted the number of macroscopically visible melanoma metastases on the surface of the lungs. Depletion of NK cells and CD8 T cells was performed as described[54].

10. Serial transplantation of primary cutaneous melanomas derived from HGF×CDK4$^{R24C/R24C}$ mice.

We dissociated primary melanomas derived from carcinogen-treated HGF×CDK4$^{R24C/R24C}$ mice[23, 30], passed them through a nylon mesh filter (70 µl) and reinjected them in the flank of CDK4$^{R24C/R24C}$ mice. We performed treatment experiments with groups of 5 mice intracutaneously injected with $10^5$ viable transplanted HGF×CDK4$^{R24C/R24C}$ melanoma cells derived from one transplanted melanoma in the fourth to sixth passage. We monitored tumor growth weekly by measuring the maximal two bisecting diameters (L=length and W=width) using a vernier sliding jaw caliper. We calculated tumor size according to the formula Volume= $(L \times W^2) \times 0.5$ and expressed it in $mm^3$. We sacrificed mice with tumors greater than 4000 $mm^3$.

11. Statistical Analyses

We determined the statistical significance of differences by the two-tailed Student's t-test. For the analysis of the tumor experiments we used the non-parametric Mann-Whitney U test to compare the means between two groups. Statistical analysis was performed using SPSS software (SPSS, Chicago, Ill.). P values<0.05 were considered significant.

Figure 23:
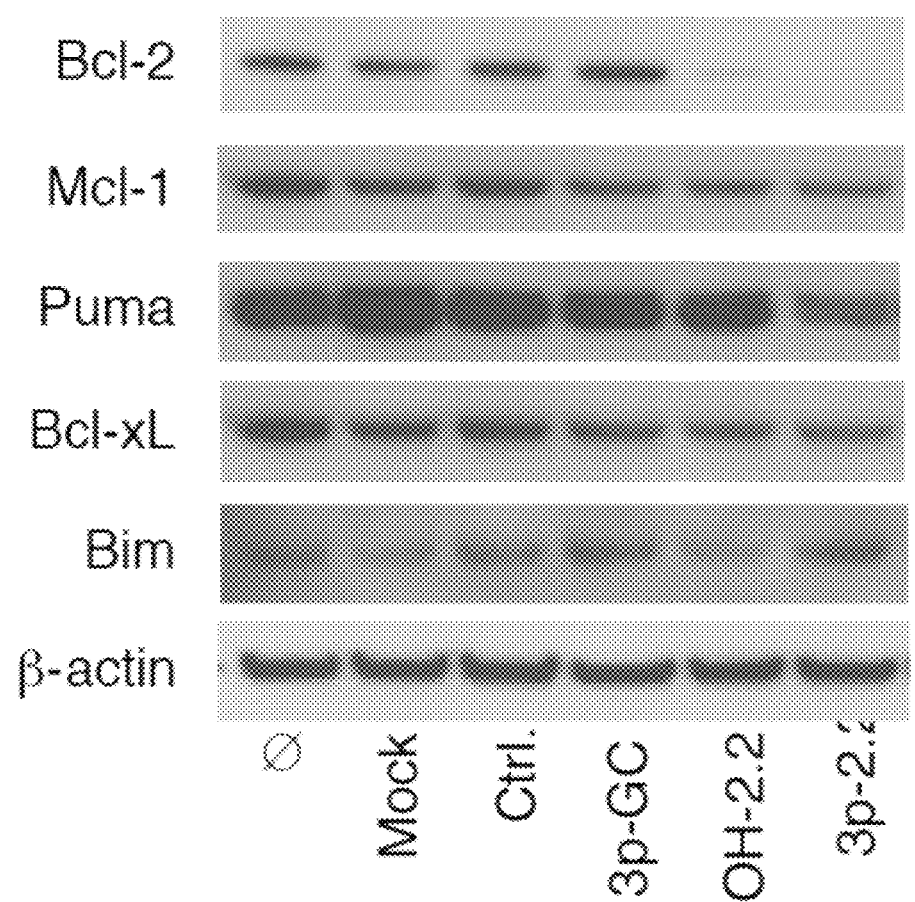
FIG. 23. Gene-silencing of Bcl-2 by 5'-triphosphate siRNA is specific

Anti-Bcl-2 siRNA with 5'-Triphosphate Ends Reduces Formation of Lung Metastases in B16 Melanoma In order to test the feasibility of the 3p-siRNA approach for tumor therapy, we tested three synthetic siRNAs (anti-bcl-2.1, anti-bcl-2.2, anti-bcl-2.3) targeting different regions of murine Bcl-2 mRNA for their ability to downregulate Bcl-2 protein in B16 melanoma cells (FIG. 17a left panel and Table 7, below). The activity and the specificity of Bcl-2 downregulation was maintained when anti-Bcl-siRNA contained a 5'-triphosphate (FIG. 17a right panel and Table 8, OH-2.2 and 3p-2.2 compared to 3p-GC and mismatch 3p-MM). Silencing of Bcl-2 by 3p-2.2 was specific since expression of the pro-survival Bcl-2 family members Mcl-1 and Bcl-xL and of the pro-apoptotic BH3-only Bcl-2 family members Puma and Bim was not inhibited (FIG. 23). Using RACE (Rapid Amplification of cDNA Ends) technology and sequencing revealed that Bcl-2 silencing generated specific cleavage products confirming RNA interference (FIG. 17b).

Next we examined the anti-tumor activity of 3p-2.2 in the B16 melanoma lung metastasis model in vivo. Mice were treated with RNA on days 3, 6 and 9 after tumor cell inoculation and growth of lung metastases was assessed on day 12 or 17. As shown in FIG. 17c, OH-2.2 (gene silencing activity but no RIG-I ligand activity expected) and the 3p-RNA oligonucleotides 3p-MM and 3p-GC (RIG-I ligand activity but no gene silencing activity expected) inhibited the growth of melanoma metastases to a certain degree. However, 3p-2.2, which combines Bcl-2-specific gene-silencing and immunostimulatory properties, displayed significantly enhanced therapeutic anti-tumor activity.

Type I IFN and NK Cells are Required for the Anti-Tumor Activity

Since 5'-triphosphate RNA is known to stimulate type I interferon by activating RIG-I we sought to evaluate the contribution of type I IFN to the anti-tumor effect. Experiments in type I IFN receptor knockout mice (IFNAR−/−) confirmed that the observed anti-tumor activity of 3p-2.2 in vivo depended on intact type I IFN signaling (FIG. 18a, compare left and middle panel). We found that the number of metastases was strongly reduced upon treatment with 3p-2.2 in TLR7-deficient mice suggesting that TLR7 was not required for the anti-tumor activity of 3p-2.2 (FIG. 18a, right panel). This indicated that not TLR7- but rather RIG-I-mediated 3p-2.2 recognition and type I IFN induction plays a dominant role. Depletion studies demonstrated that the anti-tumor activity of 3p-2.2 in the B16 melanoma model depended on NK cells but not CD8 T cells (FIG. 18b). Together these results confirm that both gene silencing (since the 3p control 3p-GC is significantly less active) and RIG-I (but not TLR7) dependent immunity contribute to anti-tumor activity of 3p-2-2 in the B16 melanoma model in vivo.

Innate Response and Apoptosis in Immune Cell Subsets and Tumor Cells In Vitro

Next we studied stimulation of specific immune cell subsets in vitro. While in plasmacytoid dendritic cells TLR7 activation is sufficient to induce the production of IFN-α, conventional dendritic cells (cDC) produce IFN-α in response to viral infection but not to TLR7 activation. 3p-MM, 3p-GC and 3p-2.2 induced similar amounts of IFN-α in cDC, while OH-2.2 was inactive (FIG. 19a). 3p-RNA did not induce IFN-α in B cells, NK cells and T cells. Studies with dendritic cells isolated from mice genetically deficient for TLR7 or the cytosolic helicases MDA-5 or RIG-I confirmed that the induction of IFN-α in cDC by 3p-2.2 and 3p-GC depended on RIG-I but not MDA-5 or TLR7 (FIG. 24). No induction of apoptosis was observed in cDC or other lymphocyte subsets exposed to 3p-2.2 (FIG. 19b).

Since RIG-I is broadly expressed in many cell types, we examined direct induction of type I IFNs in B16 melanoma cells. 3p-2.2, 3p-MM or 3p-GC stimulated similar levels of IFN-β promoter reporter gene activity in B16 cells but did not respond to OH-2.2 or to phosphatase-treated 3p-2.2 (FIG. 19c). Resting B16 melanoma cells expressed little RIG-I; however RIG-I expression was strongly upregulated in the presence of exogenous IFN-β or 3p-2.2 (FIG. 19d). B16 cells treated with 3p-2.2 or 3p-GC but not OH-2.2 secreted the chemokine IP-10 and upregulated MHC class I. (FIGS. 25a, and 25b). Type I IFN induction in B16 tumor cells was RIG-I dependent, since inhibition of RIG-I expression by RIG-I-specific siRNA or overexpression of NS3-4A (encoding a serine protease of hepatitis C virus cleaving IPS-1[57,53], also known as Cardif, MAVS or VISA, a key signaling molecule of RIG-I) both eliminated the type I IFN response (FIG. 25c, d). These data indicated that 3p-RNA is able to activate type I IFN through Rig-I directly in tumor cells.

3p-2.2 siRNA was designed to promote the induction of apoptosis via silencing of the anti-apoptotic protein Bcl-2. Indeed, 3p-2.2 strongly induced apoptosis in B16 melanoma cells (FIG. 19e). Apoptosis induction with 3p-2.2 was substantially higher than with OH-2.2 alone and anti-bcl-2-siRNA reduced apoptosis induction by 3p-2.2 suggesting that RIG-I contributed to apoptosis induction by 3p-2.2 (FIGS. 19e and 19f). Furthermore, apoptosis induction by 3p-GC and 3p-2.2 was reduced in the absence of IFNAR (FIG. 19f; FIG. 25e) suggesting that type I IFN signaling is involved in sensitizing tumor cells to RIG-I. Unlike B16 tumor cells, fibroblasts were not sensitive towards apoptosis induction by silencing of Bcl-2 (OH-2.2) or activation of RIG-I (3p-GC) or the combination of both (3p-2.2) (FIG. 19g). Together with the lack of apoptosis induction in immune cell subsets (FIG. 19b) these results indicate that downregulation of Bcl-2 and activation of RIG-I preferentially lead to apoptosis of melanoma cells and suggest a relative tumor selectivity of this approach.

Analysis of Innate Immune Activation In Vivo

Next we studied 3p-2.2-induced innate immune responses in vivo. 3p-2.2 induced systemic levels of IFN-α, IL-12p40 and IFN-γ (FIG. 20a, FIG. 26). IFN-α was largely derived from CD11c+ dendritic cells as evidenced by removal of this cell type in CD11c-DTR mice. The Th1 cytokine induction by 3p-2.2 in vivo was dominated by RIG-I, with minor contribution of TLR7 (FIG. 26). Cytokine production was dose-dependent and transient. Mice showed reduced counts of lymphocytes and thrombocytes but not erythrocytes, presumably due to systemic interferons, but no other obvious toxicities (FIG. 27). The ex vivo analysis of spleen cells demonstrated potent activation of myeloid and plasmacytoid dendritic cells, NK cells, CD4 and CD8 T cells (FIG. 28). Activation of splenic NK cells was observed in wild-type and TLR7-deficient mice and required the presence of the type I IFN receptor; NK cells showed ex vivo tumoricidal activity against B16 melanoma cells (FIG. 29). Treatment with 3p-2.2 was associated with enhanced recruitment and activation of NK cells in the lungs (FIG. 20b,c).

Contribution of Bcl-2-Silencing to Anti-Tumor Activity In Vivo

Confocal microscopy confirmed that fluorescently-labeled siRNA reached healthy lung tissue as well as metastases (FIG. 30a). Bcl-2 was silenced in tumor cells (FIG. 20d) of tumor-bearing mice treated with 3p-2.2 and OH-2.2 (FIG. 20d and FIG. 30b). Downregulation of Bcl-2 was associated with RNAi in vivo, as only the bcl-2 specific siRNAs generated a specific cleavage product via 5'-RACE (FIG. 20e). Tunnel staining revealed massive apoptosis in mice treated with 3p-2.2 compared to mice treated with control RNA, although the number of HMB45 positive tumor cells was much higher in the control-treated animals (FIG. 20f). No Bcl-2 silencing or induction of apoptosis was seen in immune cell subsets in vivo (FIG. 30c) further supporting relative tumor cell selectivity.

Next, rescue experiments were performed to confirm that silencing of bcl-2 contributes to the therapeutic activity of 3p-bcl-2-siRNA in vivo. B16 melanoma cells were stably transduced with a mutated bcl-2 cDNA specifically designed to disrupt the target cleavage site of the siRNA anti-Bcl-2.2 without affecting the amino acid sequence of the bcl-2 protein (FIG. 31). Expression of the mutated bcl-2 cDNA in B16 melanoma cells (mut-B16) prevented bcl-2 silencing and apoptosis induction by 3p-2.2 but not by 3p-2.4 targeting bcl-2 mRNA at a different non-mutated site (FIGS. 21a and 21b, Table 7).

Figure 21:
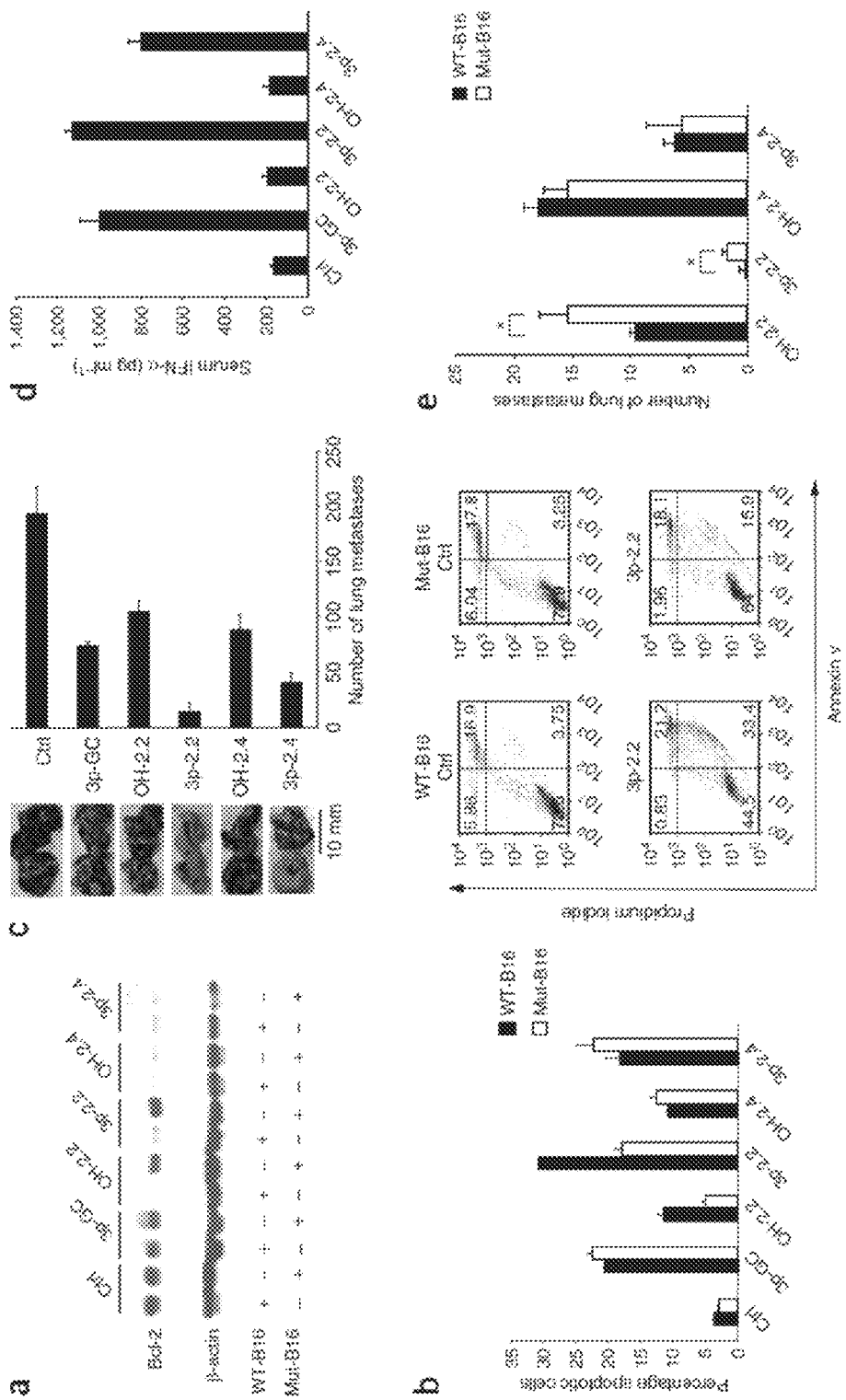
FIG. 21. Bcl-2-specific gene silencing contributes to 3p-siRNA induced inhibition of tumor growth and apoptosis
(a) Western blot analysis of Bcl-2 protein expression in B16 cells stably transfected with wilde-type Bcl-2 (WT-B16) or a specifically mutated Bcl-2 cDNA (Mut-B16) after treatment with the indicated siRNAs. (b) Left panel: Flow cytometric analysis of apoptosis induction in WT-B16 or Mut-B16 cells 48 h after transfection with the indicated RNAs. Results are shown as mean percent of apoptotic cells±SEM of three independent experiments. Right panel: one representative dot plot of three independent experiments is shown. (c) Intravenous challenge of C57BL/6 mice with B16 melanoma cells and treatment with the indicated siR-NAs. The mean number of macroscopically visible melanoma metastases on the lung surfaces of each group (±SEM) are shown. (d) Serum IFN-α levels 6 h after treatment of tumor-bearing mice with the indicated RNA. Data are shown as mean±SEM of four mice/group (e) Intravenous challenge of C57BL/6 mice with WT-B16 or Mut-B16 melanoma cells and treatment with the indicated siRNAs. The mean number of macroscopically visible melanoma metastases on the lung surfaces of each group (±SEM) are shown. *P<0.01, Mann-Whitney U test).

In vivo, 3p-2.4 and 3p-2.2 showed similar anti-tumor efficacy against B16 melanoma lung metastases (FIG. 21c) and induced similar systemic levels of IFN-α (FIG. 21d). In vivo rescue experiments with WT-B16 and Mut-B16 confirmed that the therapeutic effect of OH-2.2 and 3p-2.2 depended in part on bcl-2 gene silencing in tumor cells (FIG. 21e). Taken together, these results provide evidence that both gene silencing and RIG-I-dependent activation of innate immunity contribute to the anti-tumor activity of 3p-2.2 in the B16 melanoma model in vivo.

Figure 22:
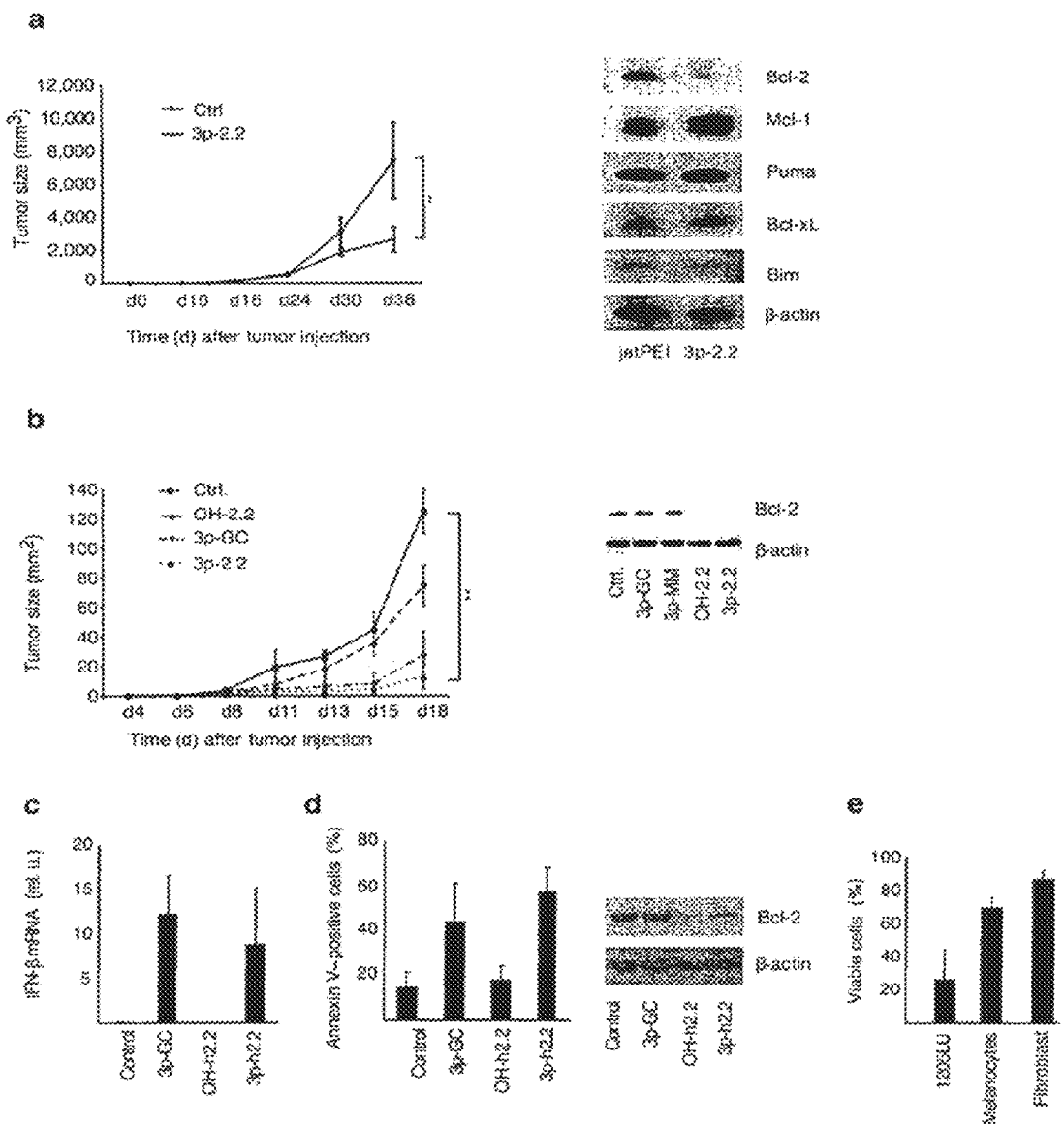
FIG. 22. Bcl-2-specific 3p-siRNA is effective in other models of tumorigenesis and in human melanoma (a) Left panel: Treatment of CDK4$^{R24C}$ mice with transplanted HGF×CDK4$^{R24C}$ melanomas in the skin by intra- and peritumoral injections of 3p-2.2 or jetPEI on days 10, 16, 24 and 30. Shown is the mean tumor volume of each group in mm$^3$±SEM (P<0.01). Right panel: Analysis of tumor lysates from transplanted HGF×CDK4$^{R24C}$ melanomas for Bcl-2, Bim, Mcl-1, Puma and Bcl-xL protein expression by Western blot 24 h after treatment. (b) Left panel: Treatment of Balb/c mice with C26 tumors in the skin by intravenous injections with the indicated siRNAs on days 6, 9, 12 and 15. Shown is the mean tumor area in mm$^2$±SEM of each group (P<0.01). Right panel: Analysis of Bcl-2 protein expression 48 hours after transfection of C26 cells with the indicated RNAs. (c) Activation of IFN-β RNA expression following treatment of 1205Lu cells with the indicated siRNAs using quantitative RT-PCR. The mean±SD of three independent experiments is shown. (d). Left panel: Flow cytometric analysis of apoptosis induction in 1205Lu cells treated with the siRNAs as described in (c). The mean±SD of three independent experiments is shown. Right panel: Assessment of Bcl-2-silencing activity by immunoblotting. Representative results of three independent experiments are depicted. (e) Cell viability of 1205Lu (three independent experiments mean±SD), of human primary melanocytes and human primary fibroblasts (both isolated from three different donors, means±SD) 24 h after transfection of 3p-h2.2.

Next we confirmed the anti-tumor activity of 3p-siRNA in a new genetic melanoma model which is based on important events in the molecular pathogenesis of human melanoma and much more closely mimics the clinical setting[57]. Primary melanomas derived from the skin of HGF/CDK4$^{R24C}$ mice were serially transplanted to groups of CDK4$^{R24C}$ mice. Repetitive peritumoral injections with 3p-2.2 led to a significant delay in tumor growth (FIG. 22a, left panel) associated with downregulation of Bcl-2 but not Mcl-1, Bcl-xL, Puma or Bim in melanoma cells in vivo (FIG. 22a, right panel). In addition, 3p-2.2 also showed significant anti-tumor efficacy in a colon carcinoma model in Balb/C mice (FIG. 22b, left panel), associated with systemic production of IFN-α and downregulation of Bcl-2 expression (FIG. 22b, right panel, FIG. 32).

Finally we designed human anti-Bcl-2 siRNA (OH-h2.2 and 3p-h2.2) and tested them in a human melanoma cell line (1205 Lu). Treatment of 1205 Lu with 3p-h2.2 and 3p-GC, but not with OH-h2.2 or the control RNA was able to induce IFN-β (FIG. 22c). Both OH-h2.2 and 3p-h2.2 strongly reduced Bcl-2 protein levels (FIG. 22d). Similar to 3p-2.2 in murine B16 melanoma cells, 3p-h2.2 strongly promoted apoptosis (FIG. 22d) and decreased viability of human melanoma cells, while the pro-apoptotic activity was less pronounced in primary human melanocytes and primary human fibroblasts both isolated from skin of healthy donors (FIG. 22e).

Results

The results of this study demonstrate that systemic administration of a siRNA deliberately designed to silence Bcl-2 and to activate RIG-I (3p-2.2) strongly inhibits tumor growth reflected by massive tumor apoptosis on a histological level. This response requires type I IFN and NK cells, and is associated with the induction of systemic Th1 cytokines (IFN-α, IL-12p40, IFN-γ), direct and indirect activation of immune cell subsets and with recruitment and activation of NK cells in lung tissue. Furthermore, sequence-specific silencing of Bcl-2 contributes to anti-tumor efficacy of 3p-2.2. This is evidenced by site-specific cleavage of Bcl-2 mRNA, sequence-dependent rescue studies in vitro and in vivo, and downregulation of Bcl-2 protein on a single cell level in lung tumor cells.

Due to its molecular design, siRNA 3p-2.2 contains two distinct functional properties: a) gene silencing and b) RIG-I activation. A number of biological effects caused by these two properties may cooperate to provoke the beneficial anti-tumor response in vivo: a) silencing of Bcl-2 may induce apoptosis in cells that depend on Bcl-2 overexpression (such as tumor cells), and via the same mechanism may as well sensitize tumor cells towards innate effector cells[47]: b) RIG-I activation: RIG-I is expressed in immune cells as well as in non-immune cells including tumor cells. Consequently, activation of RIG-I leads to direct and indirect activation of immune cell subsets, but also provokes innate responses directly in tumor cells such as the production of type I IFNs or chemokines, and directly promotes apoptosis. These activities act in concert to elicit the potent anti-tumor effect seen (for a schematic overview of the potential anti-tumor mechanism elicited by 3p-siRNA see FIG. 33).

In fact, our data provide experimental evidence that B16 melanoma cells express RIG-I and that 3p-2.2 not only silences Bcl-2 but also stimulates type I IFN, IP-10, MHC I, and induces apoptosis directly in tumor cells. Furthermore, we demonstrate that silencing of Bcl-2 in tumor cells does not require RIG-I ligand activity (OH-2.2, same sequence as 3p-2.2 but no triphosphate), and that RIG-I effects are independent of Bcl-2 silencing activity (3p-MM and 3p-GC, triphosphate but no silencing). Importantly, compared to the respective single activities, our data demonstrate synergistic induction of tumor cell apoptosis in vitro and synergistic inhibition of Bcl-2 and induction of apoptosis in tumor cells in vivo when both silencing and RIG-I activity are in place (3p-2.2 compared to OH-2.2, 3p-MM or 3p-GC alone).

The lower anti-tumor response of 3p-MM and 3p-GC compared to 3p-2.2 in vivo, the lack of Bcl-2 inhibition in tumor cells in vivo by the RIG-I ligand (3p-GC) alone, and the sequence-specific rescue experiments confirm that gene silencing is a key functional property of 3p-2.2. Likewise, the lower overall anti-tumor response to anti-Bcl-2 siRNA (OH-2.2) despite strong inhibition of Bcl-2 in tumor cells in vivo highlights the importance of the innate contribution. Each mechanism by itself is not as potent to suppress tumor growth in vivo as the combination. This is supported by the rescue experiments which showed that apoptosis induced by OH-2.2 depended completely on Bcl-2 while apoptosis induced by 3p-2.2 depended only in part on Bcl-2 gene silencing.

A key question is how systemic administration of the combinatorial RNA molecule 3p-2.2 can result in the tumor specificity observed. Following intravenous injection, fluorescently-labeled RNA complexed with polyethylenimine (PEI) was enriched in lungs but also liver, spleen and kidney (data not shown). Thus, in our study RNA delivery is not targeted to the tumor. Nevertheless, tumor specific apoptosis induction is seen which may be explained by a cooperation of the following three mechanisms: first, melanoma cells express high levels of Bcl-2 to prevent spontaneous tumor cell apoptosis[50,52], while in normal cells all checkpoints of apoptosis are intact and inhibition of Bcl-2 alone is not sufficient for apoptosis induction. This is supported by our data comparing B16 tumor cells and fibroblasts as well as human melanoma cells and primary human melanocytes. Second, in our hands RIG-I activation is sufficient to induce apoptosis in B16 tumor cells and human melanoma cells but not in normal cells such as fibroblasts, human fibroblasts or human melanocytes. Third, B16 melanoma cells are much more sensitive to killing by activated NK cells, strongly upregulate MHC I expression and secrete high amounts of IP-10 only after transfection with 3p-siRNA. We therefore hypothesize that RIG-I-mediated activation of the type I IFN system in tumor cells leads to changes on the cell surface that predisposes these cells for NK cell attack and destruction, similar to what was proposed by Stetson and Medzhitov[53].

Our studies show that treatment with 3p-siRNA can be extended to other models of tumorigenesis. We found anti-tumor activity against melanomas derived from primary cutaneous tumors in HGF×CDK4$^{R24C}$ mice. The HGF×CDK4$^{R24C}$ mouse melanoma model resembles the expected clinical situation in melanoma patients much more closely, first because melanomas arise as a consequence of genetic alterations similar to those observed in patients and second because melanomagenesis can be promoted by UV irradiation. Repeated administration of 3p-2.2 resulted in a significant delay in tumor growth in this model. We also observed anti-tumor efficacy of 3p-siRNA in a syngeneic colon carcinoma model in Balb/c mice. Furthermore, we provide evidence that the approach can be adapted to the human system. A Bcl-2-specific 3p-siRNA mediated both gene silencing and RIG-I activation in human melanoma cells leading to apoptosis, whereas melanocytes and fibroblasts were resistant to apoptosis induction. Based on these observations, the principles of this approach show promise for clinical translation.

The gene silencing activity of such combinatorial 3p-siRNA molecules can be directed to any given molecularly defined genetic event that governs tumor cell survival. A combination of siRNA sequences selected for different tumor-related genes is feasible. New targets identified by functional screening in tumor cells can directly be imported into this combinatorial RNA system. This will advance our ability to attack the tumor from different biological angles which we think is required to effectively counteract tumor cell survival, plasticity, and immune escape. Despite the relative tumor specificity seen in our study, this strategy will be further improved by targeted delivery of the RNA to tumor tissue.

REFERENCES

1. Kawai T, Akira S. Nat Immunol 2006; 7(2):131-7.
2. Alexopoulou L et al. Nature 2001; 413(6857):732-8.
3. Diebold S S et al. Science 2004; 303(5663):1529-31.
4. Heil F et al. Science 2004; 303(5663):1526-9.
5. Hornung V et al. Nat Med 2005; 11(3):263-70.
6. Hemmi H et al. Nature 2000; 408(6813):740-5.
7. Matsumoto M et al. J Immunol 2003; 171(6):3154-62.
8. Nishiya T, DeFranco A L. J Biol Chem 2004; 279(18): 19008-17.
9. Latz E et al. Nat Immunol 2004; 5(2):190-8.
10. Kato H et al. Nature 2006; 441(7089):101-5.
11. Yoneyama M et al. Nat Immunol 2004; 5(7):730-7.
12. Kato H et al. Immunity 2005; 23(1):19-28.
13. Lau C M et al. J Exp Med 2005; 202(9):1171-7.
14. Gitlin L et al. Proc Natl Acad Sci USA 2006; 103(22): 8459-64.
15. Hornung V et al. Science 2006; 314(5801):994-7.
16. Marques J T et al. Nat Biotechnol 2006; 24(5):559-65.
17. Judge A D et al. Nat Biotechnol 2005; 23(4):457-62.
18. Sioud M. Eur J Immunol 2006; 36(5):1222-30.
19. WO 2008/017473
20. Kim D H et al. Nat Biotechnol 2004; 22:321-5.
21. US 2006/0178334
22. WO 2003/086280
23. Reynold et al. Nat Biotechnol 2004; 22:326-30.
24. Takahasi K et al. Molecular Cell 2008; 29:1-13.
25. Pichlm air A et al. Science 2006; 314:997-1001.
26. Cui S et al. Molecular Cell 2008; 29:169-179.
27. Ludwig J & Eckstein F J Org Chem 1989; 54:631-635.
28. WO 2007/031319
29. WO 2007/031322
30. Gondai T et al. Nucleic Acids Res 36(3):e18.
31. Haas T et al. (2008) Immunity 28:315-323.
32. Latz E et al. (2007) Nat Immunol 8:772-779.
33. Weber F et al. (2006) J Virol 80:5059-5064.
34. Loo Y M et al. (2008) J Virol 82:335-345.
35. Bonin M et al. (2000) RNA 6:563-570.
36. Hofacker I L et al. (2004) Bioinformatics 20:1495-1499.
37. Portela A & Digard P (2992) J Gen Virol 83:723-734.
38. Hanahan, D. & Weinberg, R. A. (2000) *Cell* 100, 57-70
39. Bui, J. D. & Schreiber, R. D. (2007) *Curr Opin Immunol* 19, 203-8.
40. Rubin, B. P., Heinrich, M. C. & Corless, C. L. (2007) *Lancet* 369, 1731-41
41. Curiel, T. J. (2007) *J Clin Invest* 117, 1167-74
42. Uno, T. et al. (2006) *Nat Med* 12, 693-8
43. Obeid, M. et al. (2007) *Nat Med* 13, 54-61
44. Schlee, M., Hornung, V. & Hartmann, G. (2006) *Mol Ther* 14, 463-70
45. Pei, Y. & Tuschl, T. (2006) *Nat Methods* 3, 670-6
46. de Fougerolles, A., Vornlocher, H. P., Maraganore, J. & Lieberman, (2007) *J. Nat Rev Drug Discov* 6, 443-53
47. Pichlmair, A. et al. (2006) *Science* 314, 997-1001.
48. Yoneyama, M. & Fujita, T. (2007), *J Biol Chem* 282, 15315-8
49. Yoneyama, M. & Fujita, T. (2007) *J Biol Chem* 282, 15315-8
50. Miller, A. J. & Mihm, M. C., Jr. (2006) *N Engl J Med* 355, 51-65
51. Daniel, N. N. & Korsmeyer, S. J. (2004) *Cell* 116, 205-19
52. McGill, G. G. et al. (2002) *Cell* 109, 707-18
53. Stetson, D. B. & Medzhitov, R. (2006) *J Exp Med* 203, 1837-41.
54. Mocikat, R. et at (2003). *Immunity* 19, 561-9
55. Muller, U. et al. (1994), *Science* 264, 1918-21
56. Kamphuis, E. et at (2006), *Blood* 108, 3253-61.
57. Tormo, D. et al. (2006), *Cancer Res* 66, 5427-35.

The invention claimed is:

1. An oligonucleotide preparation comprising an essentially homogenous population of an oligonucleotide, wherein the oligonucleotide has one blunt end, wherein the oligonucleotide comprises at least 1 ribonucleotide at the 5' end at the blunt end, wherein the blunt end bears a 5' triphosphate attached to the most 5' ribonucleotide, wherein the 5' triphosphate is free of any cap structure, wherein the blunt end is an end of a double-stranded section, and wherein the double-stranded section is at least 19 base pairs in length, and (a) wherein the oligonucleotide is double-stranded and the other end of the oligonucleotide comprises a 5' or 3' overhang; or (b) wherein the double-stranded section is the stem of the stem-and-loop structure.

2. The oligonucleotide preparation of claim 1, wherein the double-stranded section is a fully double-stranded section.

3. The oligonucleotide preparation of claim 1, wherein the double-stranded section is at least 21 base pairs in length.

4. The oligonucleotide preparation of claim 1, wherein the oligonucleotide comprises at least one inosine.

5. The oligonucleotide preparation of claim 1, wherein the most 5' ribonucleotide with the triphosphate attached to is selected from the group consisting of A, G and U.

6. The oligonucleotide preparation of claim 1, wherein the sequence of the first 4 ribonucleotides at the 5' end bearing the 5'-triphosphate is selected from the group consisting of: AAGU, AAAG, AUGG, AUUA, AACG, AUGA, AGUU, AUUG, AACA, AGAA, AGCA, AACU, AUCG, AGGA, AUCA, AUGC, AGUA, AAGC, AACC, AGGU, AAAC, AUGU, ACUG, ACGA, ACAG, AAGG, ACAU, ACGC, AAAU, ACGG, AUUC, AGUG, ACAA, AUCC, AGUC, wherein the sequence is in the 5'→3' direction.

7. The oligonucleotide preparation of claim 1, wherein the oligonucleotide is free of modifications selected from the group consisting of pseudouridine, 2-triouridine, 2'-fluorine-dNTP.

8. The oligonucleotide preparation of claim 1, wherein the most 3' nucleotide which base pairs with the most 5' ribonucleotide bearing the 5' triphosphate at the blunt end is 2'-O-methylated.

9. The oligonucleotide preparation of claim 1, wherein the oligonucleotide comprises at least one structural motif recognized by at least one of TLR3, TLR7, TLR8 and TLR9.

10. The oligonucleotide preparation of claim 1, wherein the oligonucleotide has target gene-silencing activity.

11. The oligonucleotide preparation of claim 10, wherein the oligonucleotide has both target gene-silencing activity and the ability of RIG-I activation.

12. The oligonucleotide preparation of claim 10, wherein the target gene is Bcl-2.

13. The oligonucleotide preparation of claim 1, wherein the oligonucleotide contains a synthetic or modified internucleoside linkage, or a mixture thereof, provided the linkage(s) do not compromise the type I IFN-inducing activity of the oligonucleotide.

14. The oligonucleotide preparation of claim 1, wherein the oligonucleotide comprises phosphorothioate linkage(s) and/or pyrophosphate linkage(s).

15. A pharmaceutical composition comprising at least one oligonucleotide preparation of claim 1 and a pharmaceutically acceptable carrier.

16. The pharmaceutical composition of claim 15, further comprising an immunostimulatory agent, an antigen, an anti-viral agent, an anti-bacterial agent, an anti-tumor agent, retinoic acid, IFN-α, IFN-β, or any combination thereof.

17. A method for preventing or treating a disease selected from a tumor, an infection, and an immune disorder in a subject, the method comprising the step of administering a pharmaceutical composition as defined in claim 14 to said subject.

18. The method of claim 17, wherein the pharmaceutical composition is administered in combination with a prophylactic or therapeutic treatment of a tumor, an infection or an immune disorder.

19. The method of claim 17, wherein the oligonucleotide preparation is administered in combination with an immunostimulatory agent, an antigen, an anti-viral agent, an anti-bacterial agent, an anti-tumor agent, retinoic acid, IFN-α, IFN-β, or any combination thereof.

20. An in vitro method for inducing type I IFN production in a cell, comprising the steps of:

(a) mixing at least one oligonucleotide preparation of claim 1 with a complexation agent; and (b) contacting a cell with the mixture of (a), wherein the cell expresses RIG-I.

* * * * *